US012201354B1

(12) United States Patent
Mahmoudi et al.

(10) Patent No.: US 12,201,354 B1
(45) Date of Patent: Jan. 21, 2025

(54) EXPANDABLE ABLATION MECHANISMS FOR SHUNTING CATHETERS

(71) Applicant: THERAHEART INC., Irvine, CA (US)

(72) Inventors: Rani Abdullah Mahmoudi, Huntington Beach, CA (US); Wei Gan, Irvine, CA (US); Ajay Dass, Costa Mesa, CA (US)

(73) Assignee: Theraheart Inc., Irvine, CA (US)

( * ) Notice: Subject to any disclaimer, the term of this patent is extended or adjusted under 35 U.S.C. 154(b) by 0 days.

(21) Appl. No.: 18/624,014

(22) Filed: Apr. 1, 2024

(51) Int. Cl.
| | |
|---|---|
| *A61B 18/18* | (2006.01) |
| *A61B 18/14* | (2006.01) |
| *A61B 17/00* | (2006.01) |
| *A61B 18/00* | (2006.01) |

(52) U.S. Cl.
CPC .............. *A61B 18/1492* (2013.01); *A61B 2017/00247* (2013.01); *A61B 2017/00336* (2013.01); *A61B 2018/00083* (2013.01); *A61B 2018/00267* (2013.01); *A61B 2018/00375* (2013.01); *A61B 2018/00577* (2013.01); *A61B 2018/00791* (2013.01)

(58) Field of Classification Search
CPC ...... A61B 18/1492; A61B 2018/00577; A61B 2018/00267; A61B 17/221; A61B 5/6858; A61B 2018/00214; A61B 5/6859; A61B 17/320725

See application file for complete search history.

(56) References Cited

U.S. PATENT DOCUMENTS

| | | | |
|---|---|---|---|
| 4,861,336 A | 8/1989 | Helzel | |
| 5,255,679 A * | 10/1993 | Imran | A61N 1/056 600/375 |
| 5,328,472 A | 7/1994 | Rupp et al. | |
| 5,800,450 A | 9/1998 | Lary et al. | |
| 6,179,832 B1 | 1/2001 | Tartaglia et al. | |
| 6,726,677 B1 | 4/2004 | Flaherty et al. | |
| 7,018,400 B2 | 3/2006 | Haarstad et al. | |

(Continued)

FOREIGN PATENT DOCUMENTS

| | | |
|---|---|---|
| CA | 2472701 C | 11/2012 |
| CN | 108784896 A | 11/2018 |

(Continued)

OTHER PUBLICATIONS

Patent Cooperative Treaty, International Search Report, mailed Jul. 17, 2024, in PCT/US2024/022547.

(Continued)

*Primary Examiner* — Michael F Peffley
*Assistant Examiner* — Amanda L Zink
(74) *Attorney, Agent, or Firm* — Faegre Drinker Biddle & Reath LLP

(57) ABSTRACT

Some embodiments of the present disclosure are directed to systems, apparatus, and methods for creating a shunt in a patient. In some embodiments, a shunting catheter includes an expandable ablation mechanism having a plurality of expandable struts and a plurality of positioning elements coupled to the plurality of expandable struts. The positioning elements are configured to be disposed radially outwardly from the expandable struts. The ablation mechanism is configured to receive energy from an energy source and deliver ablation energy to a target location of a patient.

30 Claims, 33 Drawing Sheets

(56) References Cited

U.S. PATENT DOCUMENTS

| | | | |
|---|---|---|---|
| 7,150,745 B2 | 12/2006 | Stern et al. |
| 7,655,005 B2 | 2/2010 | Bhola |
| 7,674,256 B2 | 3/2010 | Marrouche et al. |
| 7,966,057 B2 | 6/2011 | Macaulay et al. |
| 8,021,359 B2 | 9/2011 | Auth et al. |
| 8,043,360 B2 | 10/2011 | McNamara et al. |
| 8,157,860 B2 | 4/2012 | McNamara et al. |
| 8,172,896 B2 | 5/2012 | McNamara et al. |
| 8,214,015 B2 | 7/2012 | Macaulay et al. |
| 8,226,619 B2 | 7/2012 | Smith et al. |
| 8,252,042 B2 | 8/2012 | McNamara et al. |
| 8,374,680 B2 | 2/2013 | Thompson |
| 8,585,596 B1 | 11/2013 | Flaherty et al. |
| 8,617,152 B2 | 12/2013 | Flaherty et al. |
| 8,728,073 B2 | 5/2014 | McDaniel |
| 8,758,363 B2 | 6/2014 | Nishtala et al. |
| 8,874,237 B2 | 10/2014 | Schilling |
| 8,882,697 B2 | 11/2014 | McNamara et al. |
| 8,900,250 B2 | 12/2014 | Fritscher-Ravens et al. |
| 8,926,602 B2 | 1/2015 | Pageard |
| 8,968,233 B2 | 3/2015 | Duffy et al. |
| 9,089,314 B2 | 7/2015 | Wittenberger |
| 9,345,858 B2 | 5/2016 | Flaherty et al. |
| 9,468,744 B2 | 10/2016 | Arana et al. |
| 9,642,993 B2 | 5/2017 | McNamara et al. |
| 9,789,294 B2 | 10/2017 | Taft et al. |
| 9,808,303 B2 | 11/2017 | Gelfand et al. |
| 9,808,304 B2 | 11/2017 | Lalonde |
| 9,814,483 B2 | 11/2017 | Vardi |
| 9,918,789 B2 | 3/2018 | Bagley et al. |
| 10,016,620 B2 | 7/2018 | Aljuri et al. |
| 10,039,905 B1 | 8/2018 | Taft et al. |
| 10,154,878 B2 | 12/2018 | Greenlaw et al. |
| 10,188,375 B2 | 1/2019 | McNamara et al. |
| 10,207,126 B2 | 2/2019 | Benson |
| 10,245,352 B2 | 4/2019 | Wilson et al. |
| 10,327,791 B2 | 6/2019 | Argentine et al. |
| 10,426,497 B2 | 10/2019 | Chou et al. |
| 10,449,339 B2 | 10/2019 | Wilson et al. |
| 10,568,688 B2 | 2/2020 | Hu et al. |
| 10,568,751 B2 | 2/2020 | McNamara |
| 10,624,621 B2 | 4/2020 | Celermajer |
| 10,639,060 B2 | 5/2020 | Vardi et al. |
| 10,722,300 B2 | 7/2020 | Gupta et al. |
| 10,729,492 B2 | 8/2020 | Brown et al. |
| 10,758,714 B2 | 9/2020 | Laby et al. |
| 10,842,562 B2 | 11/2020 | Zhang et al. |
| 10,857,328 B2 | 12/2020 | Walzman |
| 10,864,041 B2 | 12/2020 | Urbanski et al. |
| 10,932,723 B2 | 3/2021 | Eliason et al. |
| 10,980,552 B2 | 4/2021 | Mustapha |
| 10,987,494 B2 | 4/2021 | Skinner et al. |
| 10,993,735 B2 | 5/2021 | Vardi et al. |
| 10,993,736 B2 | 5/2021 | Vardi et al. |
| 11,052,246 B2 | 7/2021 | Stewart et al. |
| 11,065,019 B1 | 7/2021 | Chou et al. |
| 11,071,585 B2 | 7/2021 | Zhang et al. |
| 11,083,520 B2 | 8/2021 | Ghaly et al. |
| 11,135,410 B2 | 10/2021 | Finch et al. |
| 11,224,449 B2 | 1/2022 | Chou et al. |
| 11,224,450 B2 | 1/2022 | Chou et al. |
| 11,350,990 B2 | 6/2022 | Gupta et al. |
| 11,369,346 B2 | 6/2022 | Stigall et al. |
| 11,369,405 B2 | 6/2022 | Vardi et al. |
| 11,399,852 B2 | 8/2022 | Wilson et al. |
| 11,534,239 B2 | 12/2022 | Bishara et al. |
| 11,612,432 B2 | 3/2023 | Pate et al. |
| 11,648,042 B2 | 5/2023 | Kelley |
| 11,690,609 B2 | 7/2023 | Celermajer |
| 11,717,429 B2 | 8/2023 | Schwartz et al. |
| 11,752,314 B2 | 9/2023 | Taft et al. |
| 11,793,529 B2 | 10/2023 | Chou et al. |
| 11,806,032 B2 | 11/2023 | Chou et al. |
| 11,865,282 B2 | 1/2024 | Nae et al. |
| 11,957,374 B2 | 4/2024 | Vardi et al. |
| 12,004,802 B2 | 6/2024 | Scott et al. |
| 2005/0154386 A1* | 7/2005 | West .............. A61B 18/1492 606/41 |
| 2005/0171527 A1 | 8/2005 | Bhola |
| 2006/0135961 A1 | 6/2006 | Rosenman et al. |
| 2007/0083194 A1* | 4/2007 | Kunis .............. A61B 18/1492 606/41 |
| 2009/0125097 A1 | 5/2009 | Bruszewski et al. |
| 2012/0123466 A1 | 5/2012 | Porter et al. |
| 2012/0130417 A1 | 5/2012 | Lepulu et al. |
| 2014/0277054 A1 | 9/2014 | Mcnamara et al. |
| 2015/0209526 A1 | 7/2015 | Matsubara et al. |
| 2016/0175041 A1 | 6/2016 | Govari et al. |
| 2018/0236211 A1 | 8/2018 | Henschel |
| 2019/0374254 A1 | 12/2019 | Arevalos et al. |
| 2020/0030588 A1 | 1/2020 | Heilman et al. |
| 2020/0038672 A1 | 2/2020 | Satake |
| 2020/0170662 A1 | 6/2020 | Vardi et al. |
| 2020/0238059 A1 | 7/2020 | Wang et al. |
| 2020/0261704 A1 | 8/2020 | Wang et al. |
| 2020/0367924 A1 | 11/2020 | Lenker et al. |
| 2021/0038298 A1 | 2/2021 | Scott et al. |
| 2021/0045805 A1 | 2/2021 | Govari et al. |
| 2021/0085384 A1 | 3/2021 | Morey et al. |
| 2021/0196373 A1 | 7/2021 | He et al. |
| 2021/0228227 A1 | 7/2021 | Vardi et al. |
| 2021/0315629 A1 | 10/2021 | Yang et al. |
| 2021/0369321 A1 | 12/2021 | Yang et al. |
| 2021/0393324 A1 | 12/2021 | Moriyama et al. |
| 2022/0022954 A1 | 1/2022 | Shuros et al. |
| 2022/0110679 A1 | 4/2022 | Wang et al. |
| 2022/0249160 A1 | 8/2022 | Pate et al. |
| 2022/0257318 A1 | 8/2022 | Belalcazar |
| 2022/0265346 A1 | 8/2022 | Gupta et al. |
| 2022/0273279 A1 | 9/2022 | Valdez et al. |
| 2022/0330975 A1 | 10/2022 | Rafiee et al. |
| 2023/0041021 A1 | 2/2023 | Urbanski et al. |
| 2023/0078647 A1 | 3/2023 | Sharma et al. |
| 2023/0099410 A1 | 3/2023 | Primeaux |
| 2023/0210592 A1 | 7/2023 | Agnew et al. |
| 2023/0248425 A1 | 8/2023 | Iijima |
| 2023/0270491 A1 | 8/2023 | Mori et al. |
| 2023/0293877 A1 | 9/2023 | Hoem |
| 2023/0404655 A1 | 12/2023 | Fukami et al. |
| 2024/0050717 A1 | 2/2024 | Rickerson et al. |

FOREIGN PATENT DOCUMENTS

| | | |
|---|---|---|
| CN | 109965974 A | 7/2019 |
| CN | 115475001 A | 12/2022 |
| CN | 115590605 A | 1/2023 |
| EP | 1878453 B1 | 12/2014 |
| EP | 3238646 A2 | 11/2017 |
| EP | 3705154 A1 | 9/2020 |
| JP | 5237572 B2 | 7/2013 |
| WO | 2003/049643 A1 | 6/2003 |
| WO | 2018/229768 A2 | 12/2018 |
| WO | 2018/229768 A9 | 12/2018 |
| WO | 2020/024612 A1 | 2/2020 |
| WO | 2020/232384 A1 | 11/2020 |
| WO | 2020/242491 A1 | 12/2020 |
| WO | 2021/091566 A1 | 5/2021 |
| WO | 2021/190547 A1 | 9/2021 |
| WO | 2022/113054 A1 | 6/2022 |
| WO | 2022/135375 A1 | 6/2022 |
| WO | 2022/166973 A1 | 8/2022 |
| WO | 2022/246158 A1 | 11/2022 |
| WO | 2023/282335 A1 | 1/2023 |
| WO | 2023/088572 A1 | 5/2023 |

OTHER PUBLICATIONS

Patent Cooperative Treaty, International Search Report, mailed Jul. 25, 2024, in PCT/US2024/023345.

Patent Cooperative Treaty, International Search Report, mailed Jun. 24, 2024, in PCT/US2024/018244.

Patent Cooperative Treaty, Written Opinion, mailed Jul. 17, 2024, in PCT/US2024/022547.

(56) References Cited

OTHER PUBLICATIONS

Patent Cooperative Treaty, Written Opinion, mailed Jul. 25, 2024, in PCT/US2024/023345.
Patent Cooperative Treaty, Written Opinion, mailed Jun. 24, 2024, in PCT/US2024/018244.
United States Patent and Trademark Office, Office Action mailed Jul. 12, 2024, for U.S. Appl. No. 18/593,832.
Babaliaros et al., "Emerging Applications for Transseptal Left Heart Catheterization: Old Techniques for New Procedures," J. Am. Coll.. Cardiol., 2008; 51:2116-22.
Edwards Lifesciences, "The Alt-Flow II trial for heart failure," 10 pages (undated).
Tanaka et al., "Treatment of Hepatic Encephalopathy Due to Inferior Mesenteric Vein/Inferior Vena Cava and Gonadal Vein Shunt Using Dual Balloon-Occluded Retrograde Transvenous Obliteration," Cardiovasc Intervent Radiol, 2009, 32:390-393 (published online Oct. 7, 2008).
United States Patent and Trademark Office, Office Action mailed Jun. 20, 2024, for U.S. Appl. No. 18/623,954.
Wilson et al., "Successful Tanscatheter Occlusion of an Anomalous Pulmonary Vein With Dual Drainage to the Left Atrium," Catheter Cardiovasc Interv, 2015, 85:1212-1216 (published online in Wiley Online Library, Apr. 7, 2015).
Patent Cooperative Treaty, International Search Report, mailed Oct. 18, 2024, in PCT/US2024/022551.
Patent Cooperative Treaty, Written Opinion, mailed Oct. 18, 2024, in PCT/US2024/022551.

* cited by examiner

EXPANDABLE ABLATION MECHANISMS FOR SHUNTING CATHETERS

TECHNICAL FIELD

Certain embodiments of the present disclosure relate to medical systems, apparatus, and methods for creating a shunt in a patient. More specifically, some embodiments of the present disclosure relate to medical systems, apparatus, and methods for creating a shunt on a cardiovascular system wall in a patient.

BACKGROUND

Heart failure is a serious condition that occurs when a heart cannot pump enough blood and oxygen to support other organs in the body. Heart failure is classified according to left ventricular (LV) function as "heart failure with reduced ejection fraction (EF)" (HFrEF; EF<40%), "mid-range EF" (HFmrEF; EF 40-49%), or "preserved EF" (HFpEF; EF≥50%). About half the patients with heart failure have HFpEF. HFpEF generally occurs when LV and left atrial filling pressures increase significantly during exercise, with an associated increase in pulmonary pressures leading to pulmonary congestion. Structural interventions to lower elevated either left or right atrial filling pressures are gaining attention.

Studies in heart failure show that lowering left atrial pressure may reduce cardiovascular events while improving functional capacity. The creation of an interatrial shunt has emerged as a therapy to decompress the left atrium in patients with acute and chronic left HF. As such, attention has turned toward the development of interatrial shunt devices (IASDs) as a means of reducing the detrimental increase in left-sided filling pressures with exercise in an effort to improve symptomatology. The IASDs may be used to treat various kinds of heart failure and/or other diseases that may result in too high of a pressure in the right atrium of a patient.

SUMMARY

Many IASDs reside in the interatrial septum, with risk for right-to-left shunting and systemic embolization. Moreover, preservation of the interatrial septum is important with an increasing number of left-sided transseptal transcatheter interventions. Improved IASDs for safer and better procedures are needed.

According to some embodiments of the present disclosure, a shunting catheter includes: a catheter shaft including a shaft lumen; an ablation shaft disposed in the shaft lumen at a first state and extended from the catheter shaft at a second state; and an ablation mechanism disposed on the ablation shaft and expandable at the second state, the ablation mechanism including: a plurality of expandable struts; and a plurality of positioning elements coupled to the plurality of expandable struts and disposed radially outwardly from the plurality of expandable struts at the second state; wherein the ablation mechanism is configured to receive energy from an energy source and deliver ablation energy to a target location of a patient.

According to some embodiments, a shunting catheter system includes: a shunting catheter, including: a catheter shaft including a shaft lumen; an ablation shaft disposed in the shaft lumen at a first state and extended from the catheter shaft at a second state; and an ablation mechanism disposed on the ablation shaft, the ablation mechanism including: a plurality of expandable struts defining an expandable cage; a plurality of positioning elements coupled to the plurality of expandable struts and disposed outwardly from the expandable cage at the second state; an energy source connected to the shunting catheter; and a controller connected to the energy source and including a processor; wherein the processor is configured to control the energy source to deliver ablation energy to a target location of a patient via the ablation mechanism.

According to some embodiments, a method for creating a shunt includes: deploying a shunting catheter in a first state, the shunting catheter including: a catheter shaft including a shaft lumen; an ablation shaft disposed in the shaft lumen at a first state; and an ablation mechanism disposed on the ablation shaft and including a plurality of expandable struts and a plurality of positioning elements; disposing the shunting catheter proximate to a target location of a patient; operating the shunting catheter to a second state, wherein the ablation shaft and the ablation mechanism extend from the catheter shaft; contacting at least one of the plurality of positioning elements against tissue at the target location of the patient; expanding an opening at the target location of the patient by expanding the plurality of expandable struts; and delivering ablation energy via the ablation mechanism to the target location of the patient.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
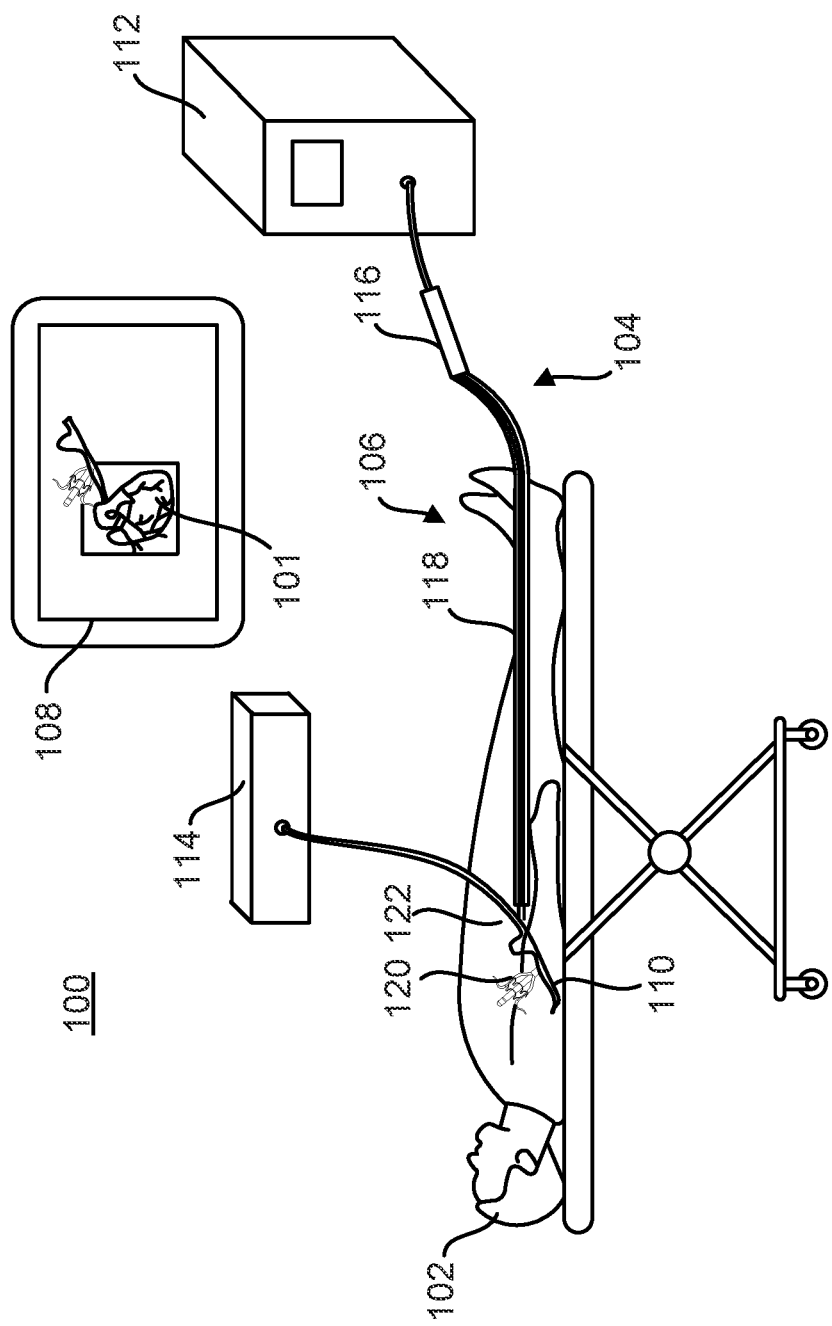
FIG. 1 is a diagram illustrating an exemplary clinical setting for treating a heart of the patient using a shunting catheter system, in accordance with embodiments of the present disclosure.

While the present disclosure is amenable to various modifications and alternative forms, specific embodiments have been shown by way of example in the drawings and are described in detail below. The present disclosure, however, is not to limit the present disclosure to the particular embodiments described. On the contrary, the present disclosure is intended to cover all modifications, equivalents, and alternatives falling within the scope of the present disclosure as defined by the appended claims.

DETAILED DESCRIPTION

The following detailed description is exemplary in nature and is not intended to limit the scope, applicability, or configuration of the present disclosure in any way. Rather, the following description provides some practical illustrations for implementing exemplary embodiments of the present disclosure. Examples of constructions, materials, and/or dimensions are provided for selected elements. Those skilled in the art will recognize that many of the noted examples have a variety of suitable alternatives.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (for example, 1 to 5 includes 1, 1.5, 2, 2.75, 3, 3.80, 4, and 5) and any number within that range.

Although illustrative methods may be represented by one or more drawings (for example, flow diagrams, communication flows, etc.), the drawings should not be interpreted as implying any requirement of, or particular order among or between, various steps disclosed herein. However, some embodiments may require certain steps and/or certain orders between certain steps, as may be explicitly described herein and/or as may be understood from the nature of the steps themselves (for example, the performance of some steps may depend on the outcome of a previous step). Additionally, a "set," "subset," or "group" of items (for example, inputs, algorithms, data values, etc.) may include one or more items and, similarly, a subset or subgroup of items may include one or more items. A "plurality" means more than one.

As used herein, the term "based on" is not meant to be restrictive, but rather indicates that a determination, identification, prediction, calculation, and/or the like, is performed by using, at least, the term following "based on" as an input. For example, predicting an outcome based on a particular piece of information may additionally, or alternatively, base the same determination on another piece of information. In some embodiments, the term "receive" or "receiving" means obtaining from a data repository (for example, database), from another system or service, from another software, or from another software component in a same software. In certain embodiments, the term "access" or "accessing" means retrieving data or information, and/or generating data or information.

There are various approaches for creating an interatrial shunt, which is a connection or gateway between the left and right atria of a patient's heart for blood to flow through. In some embodiments, examples of interatrial shunt devices (IASDs) include implants or shunting catheters. For example, devices reside in the interatrial septum, with risk for right-to-left shunting and systemic embolization. In some examples, preservation of the interatrial septum is important with an increasing number of left-sided transseptal transcatheter interventions. Improved IASDs for safer and better procedures are needed. At least some embodiments of the present disclosure are directed to a shunting catheter for deployment through a patient's coronary sinus (CS) for creating a shunt between the CS and the patient's left atrium (LA). At least some embodiments of the present disclosure are directed to a shunting catheter for deployment through a patient's atrial septum (AS) for creating a shunt between the patient's right atrium (RA) and LA.

A patient's CS ostium may have a diameter of from about 10 mm to about 20 mm. As the CS is a relatively small vessel, at least some embodiments of the present disclosure include features of a shunting catheter that helps protect a patient's vessels during deployment and/or elements for stabilizing the catheter during the procedure. In embodiments, the shunting catheter includes a catheter shaft and an ablation assembly, the ablation assembly including an ablation shaft and an ablation mechanism. The shunting catheter further includes a puncture mechanism disposed proximate to a distal end of the ablation mechanism. In some embodiments, the catheter shaft is made of flexible materials that bends according to the anatomy of the CS to conform to the shape of the patient's CS. In some embodiments, the catheter shaft includes a stabilizing element such as distal tip that has a curve (for example, a pre-existing curve) conforming to the shape of a patient's CS to help stabilize the catheter and minimize potential damage to the vessel wall of a patient's CS.

In certain embodiments, the ablation assembly is disposed in a shaft lumen of the catheter shaft at a first state, and is extended from the catheter shaft at a second state. In some embodiments, a shunt is formed by creating an opening between the patient's CS and LA. In some embodiments, a shunt is formed by creating an opening between the patient's RA and LA. In certain embodiments, the shunting catheter is inserted through the patient's superior vena cava (SVC) via a transjugular approach. In certain embodiments, the shunting catheter is inserted through the patient's inferior vena cava (IVC) via a transfemoral approach.

FIG. 1 is a diagram illustrating an exemplary clinical setting 100 for treating a heart 101 of a patient 102 using a shunting catheter system 104, in accordance with embodiments of the present disclosure. In certain embodiments, the shunting catheter system 104 includes a shunting device 106. As will be appreciated by the skilled artisan, the clinical setting 100 may have other components and arrangements of components that are not shown in FIG. 1. In some embodiments, the shunting catheter system 104 includes or is coupled to an imaging system (for example, an X-ray system), which may include one or more visualization elements and a display 108. In some embodiments, one or more visualization elements may be disposed on the shunting device 106. In certain embodiments, the imaging system can help guide a physician's operation of the shunting device 106 during a procedure.

According to certain embodiments, the shunting device 106 includes a shunting catheter 110, a controller 112, and an energy source 114 (for example, a generator). In some embodiments, the controller 112 is configured to control functional aspects of the shunting device 106. In some embodiments, the controller 112 is configured to control the energy source 114 to deliver energy to the shunting catheter 110. In certain embodiments, the controller 112 may be connected to the one or more visualization elements to facilitate positioning of the shunting catheter 110 in a patient's heart during procedure. In some embodiments, the energy source 114 is connected to the controller 112. In some embodiments, the energy source 114 may be integrated with the controller 112.

According to some embodiments, the shunting device 106 includes a handle 116, a catheter shaft 118, and an ablation assembly 120. In certain embodiments, the handle 116 is configured to be operated by a user to position the ablation assembly 120 at a target shunting location. In certain embodiments, the ablation assembly 120 includes a puncture element (for example, a puncture needle) configured to puncture through a vessel wall. In certain embodiments, the ablation assembly 120 is connected to the energy source 114 to provide shunting. For example, the ablation assembly 120 receives energy from the energy source 114 to deliver energy (for example, ablation energy, such as radiofrequency (RF) energy, phased RF energy, cryogenic energy, thermal energy, pulse energy, laser energy, microwave energy, ultrasound energy, and/or the like) to the target location (for example, a target tissue) at a cardiovascular system (for example, a circulatory system) wall. In certain embodiments, the energy source 114 provides energy in a first form (for example, electrical energy) to the ablation assembly 120, and the ablation assembly 120 delivers the ablation energy to the target location in a second form (for example, radiofrequency (RF) energy, phased RF energy, cryogenic energy, thermal energy, pulse energy, laser energy, microwave energy, ultrasound energy, and/or the like).

According to certain embodiments, during deployment, the shunting device 106 including a portion of the catheter shaft 118 enters through a patient's CS ostium. The shunting device 106 may then be oriented through one or more mechanisms in the patient's CS, as will be discussed in more detail below. In some embodiments, in order to conform to the shape of the patient's CS, the catheter shaft 118 is made of flexible materials and/or has a structure that may bend according to the anatomy of the CS. In certain embodiments, during deployment, the puncture element creates an opening at a target tissue (for example, a vessel wall), and then the ablation assembly 120 enlarges the opening at the target tissue.

In certain embodiments, the controller 112 controls the delivery of ablation energy (for example, radiofrequency (RF) energy, phased RF energy, cryogenic energy, thermal energy, pulse energy, laser energy, microwave energy, ultrasound energy, and/or the like) via the ablation assembly 120 after and/or when the opening is generated by the puncture element and/or the ablation assembly 120.

In certain embodiments, the shunting catheter 110 includes a cage having a plurality of expandable struts. In certain embodiments, the struts are configured to receive energy from the energy source and deliver ablation energy to a target location of a patient. In certain embodiments, one or more of the struts carry an electrode, and the electrode is configured to receive energy from the energy source and deliver ablation energy to a target location of a patient. In some embodiments, the struts are self-expandable. In certain embodiments, the struts are expandable via an actuator (for example, an inflatable balloon) carried within the cage. In certain embodiments, the shunting catheter 110 further includes a plurality of positioning elements coupled to the plurality of expandable struts. In some embodiments, the plurality of positioning elements are configured to contact tissue at the target location of the patient and thereby properly position the plurality of expandable struts at the target location of the patient. In certain embodiments, the positioning elements are self-expandable.

In certain embodiments, the shunting catheter 110 includes an apposition element 122 disposed proximate to the ablation assembly 120. In some embodiments, the apposition element 122 is disposed within a shaft (for example, an outer shaft) at the first state. In some embodiments, the apposition element 122 is protruded from the catheter shaft 118 at the first state and/or at the second state. In certain embodiments, the apposition element 122 can appose to a cardiovascular system wall (for example, the front wall or back wall of the CS, a left atrium wall, a right atrium wall, etc.) at the second state, for example, to help position and/or stabilize the ablation assembly 120. In certain embodiments, the apposition element 122 includes a braid structure. In some embodiments, the apposition element 122 may include a nitinol braid that can be held within the catheter shaft 118. In certain embodiments, after deployment and stabilization of the catheter shaft 118, the ablation assembly 120 and the puncture element may then be deployed. In some embodiments, the ablation assembly 120 is configured to deliver ablation energy to target tissues for creating a shunt in the patient's CS or AS.

According to some embodiments, various components (for example, the controller 112) of the shunting catheter system 104 may be implemented on one or more computing devices. In certain embodiments, a computing device may include any type of computing device suitable for implementing embodiments of the disclosure. Examples of computing devices include specialized computing devices or general-purpose computing devices such as workstations, servers, laptops, portable devices, desktop, tablet computers, hand-held devices, general-purpose graphics processing units (GPGPUs), and the like, all of which are contemplated within the scope of FIG. 1 with reference to various components of the shunting catheter system 104.

In some embodiments, a computing device (for example, the controller 112) includes a bus that, directly and/or indirectly, couples the following devices: a processor, a memory, an input/output (I/O) port, an I/O component, and a power supply. Any number of additional components, different components, and/or combinations of components may also be included in the computing device. The bus represents what may be one or more busses (such as, for example, an address bus, data bus, or combination thereof). Similarly, in some embodiments, the computing device may include a number of processors, a number of memory components, a number of I/O ports, a number of I/O components, and/or a number of power supplies. Additionally, any number of these components, or combinations thereof, may be distributed and/or duplicated across a number of computing devices. In some embodiments, various components or parts of components (for example, controller 112, shunting catheter 110, etc.) can be integrated into a physical device.

In some embodiments, the shunting catheter system 104 includes one or more memories (not illustrated). The one or more memories includes computer-readable media in the form of volatile and/or nonvolatile memory, transitory and/or non-transitory storage media and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In some embodiments, the one or more memories store computer-executable instructions for causing a processor (for example, the controller 112) to implement aspects of embodiments of system components discussed herein and/or to perform aspects of embodiments of methods and procedures discussed herein.

Computer-executable instructions may include, for example, computer code, machine-useable instructions, and the like such as, for example, program components capable of being executed by one or more processors associated with a computing device. Program components may be programmed using any number of different programming environments, including various languages, development kits, frameworks, and/or the like. Some or all of the functionality contemplated herein may also, or alternatively, be implemented in hardware and/or firmware.

In some embodiments, the memory may include a data repository that may be implemented using any one of the configurations described below. A data repository may include random access memories, flat files, XML files, and/or one or more database management systems (DBMS) executing on one or more database servers or a data center. A database management system may be a relational DBMS (RDBMS), hierarchical DBMS (HDBMS), multidimensional DBMS (MDBMS), object oriented DBMS (ODBMS or OODBMS) or object relational DBMS (ORDBMS), and/or the like. The data repository may be, for example, a single relational database. In some cases, the data repository may include a plurality of databases that can exchange and aggregate data by a data integration process or software application. In an exemplary embodiment, at least part of the data repository may be hosted in a cloud data center. In some cases, a data repository may be hosted on a single computer, a server, a storage device, a cloud server, or the like. In some other cases, a data repository may be hosted on a series of networked computers, servers, or devices. In some cases, a data repository may be hosted on tiers of data storage devices including local, regional, and central.

Various components of the shunting catheter system 104 can communicate via or be coupled to via a communication interface, for example, a wired or wireless interface. The communication interface includes, but is not limited to, any wired or wireless short-range and long-range communication interfaces. The wired interface can use cables, umbilicals, and the like. The short-range communication interfaces may be, for example, local area network (LAN), interfaces conforming to known communications standards, such as Bluetooth™ standard, IEEE 802 standards (for example, IEEE 802.11), a ZigBee™ or similar specification, such as those based on the IEEE 802.15.4 standard, or other public or proprietary wireless protocol. The long-range communication interfaces may be, for example, wide area network (WAN), cellular network interfaces, satellite communication interfaces, etc. The communication interface may be either within a private computer network, such as intranet, or on a public computer network, such as the internet. Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

Figure 2:
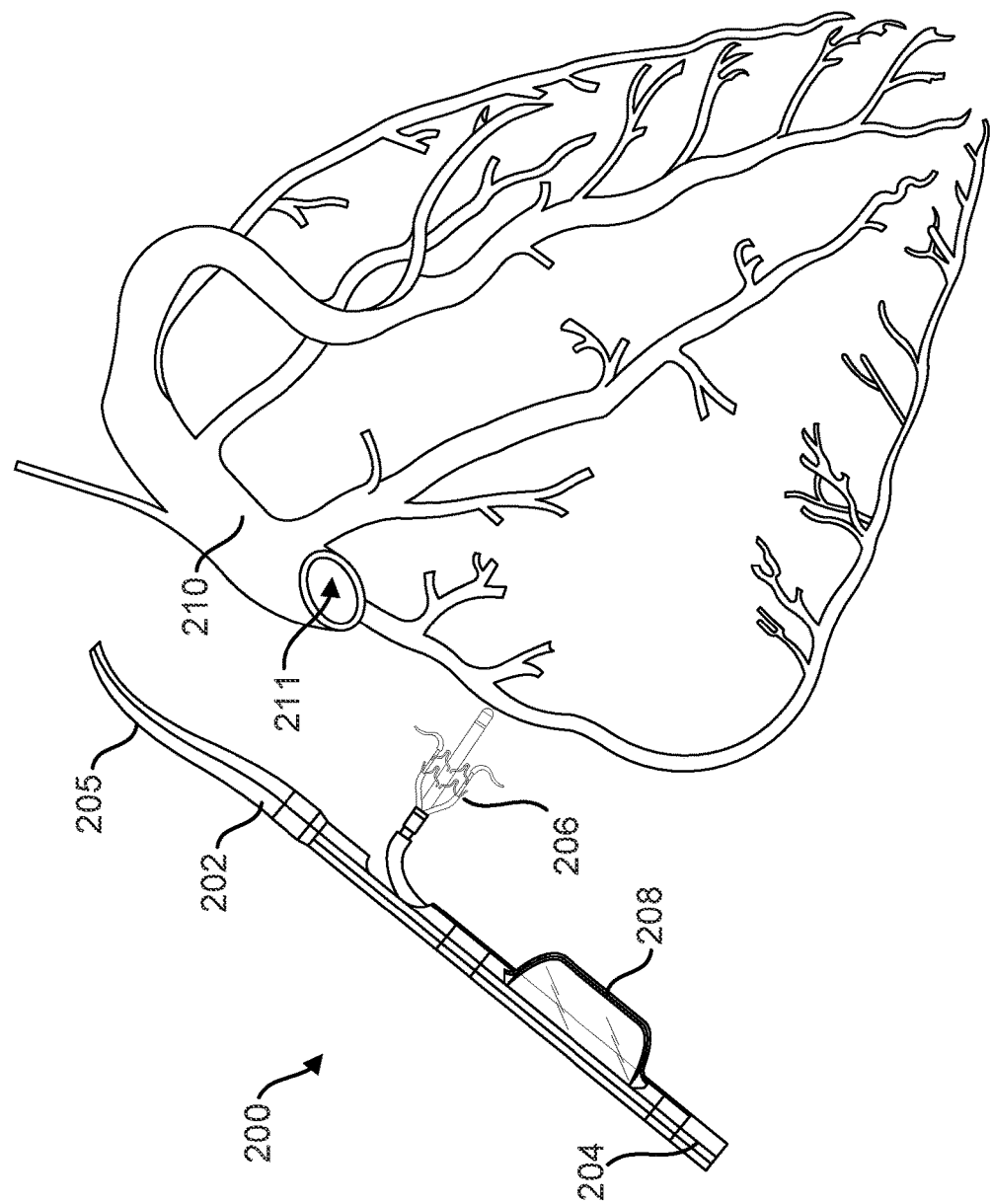
FIG. 2 is a schematic diagram illustrating an example of a shunting catheter to be deployed in a heart of a patient, in accordance with embodiments of the present disclosure.

FIG. 2 is a schematic diagram illustrating an example of a shunting device 200 to be deployed in a heart of a patient, in accordance with embodiments of the present disclosure. FIG. 2 is merely an example. One of the ordinary skilled in the art would recognize many variations, alternatives, and modifications. As shown, the shunting device 200 includes a shunting catheter 202 to be deployed to a patient's coronary sinus (CS) 210 via the CS ostium 211. In certain embodiments, the shunting catheter 202 is deployed to a patients right atrium (RA) via the inferior vena cava (IVC). In some embodiments, the shunting catheter 202 includes a catheter shaft 204, an ablation assembly 206, and an apposition element 208. In certain embodiments, the catheter shaft 204 has a curve at its distal end 205. In some embodiments, as illustrated, the ablation assembly 206 is extended from the catheter shaft 204 at a state to provide shunting (for example, a second state different from a first state to deploy the catheter 202). In certain examples, the ablation assembly 206 forms an angle greater than 10 degrees from the distal end 205 of the catheter shaft 204. In some examples, the ablation assembly 206 forms an angle greater than 30 degrees from the distal end 205 of the catheter shaft 204. In some embodiments, the ablation assembly 206 forms an angle proximate to 90 degrees from the catheter shaft 204. In some embodiments, the ablation assembly 206 forms an angle in the range of 10 degrees to 120 degrees from the catheter shaft 204.

In some embodiments, the ablation assembly 206 includes a cage having a plurality of expandable struts. In certain embodiments, the struts are configured to receive energy from the energy source and deliver ablation energy to a target location of a patient. In certain embodiments, one or more of the struts carry an electrode, and the electrode is configured to receive energy from the energy source and deliver ablation energy to a target location of a patient. In some embodiments, the struts are self-expandable. In certain embodiments, the struts are expandable via an actuator (for example, an inflatable balloon) carried within the cage. In certain embodiments, the ablation assembly 206 further includes a plurality of positioning elements coupled to the plurality of expandable struts. In some embodiments, the plurality of positioning elements are configured to contact tissue at the target location of the patient and thereby properly position the plurality of expandable struts at the target location of the patient. In certain embodiments, the positioning elements are self-expandable.

In some embodiments, the catheter shaft 204 is made of flexible material that may curve with the anatomy of the patient's CS 210. In certain embodiments, for example, the catheter shaft 204 may include polyether block amide, nylon, silicone, or a combination thereof. In some embodiments, the catheter shaft 204 may be a multi-layered and multi-material component. In some examples, the catheter shaft 204 is reinforced with a braid and/or can have an etched or casted liner. In certain embodiments, the braid for reinforcing the catheter shaft 204 may be made of nitinol. In some embodiments, the liner may be made from polyetheretherketone (PEEK), polytetrafluoroethylene (PTFE), copolymers of polyamide and polyether, or a combination thereof. In some embodiments, the catheter shaft 204 is coated for lubricity with a hydrophilic coating, or other types of coating suitable for coating a catheter shaft as known by a skilled person in the art.

In some embodiments, the shunting catheter 202 has a diameter of from about 2 mm to about 5 mm. In certain embodiments, the shunting catheter 202 has a diameter from about 2.5 mm to about 4.5 mm. In some embodiments, the shunting catheter 202 has a diameter from about 3 mm to about 4 mm. In certain embodiments, the shunting catheter 202 may have a diameter allowing it to pass through vessels and parts of the cardiovascular system to reach a target location.

Figure 3:
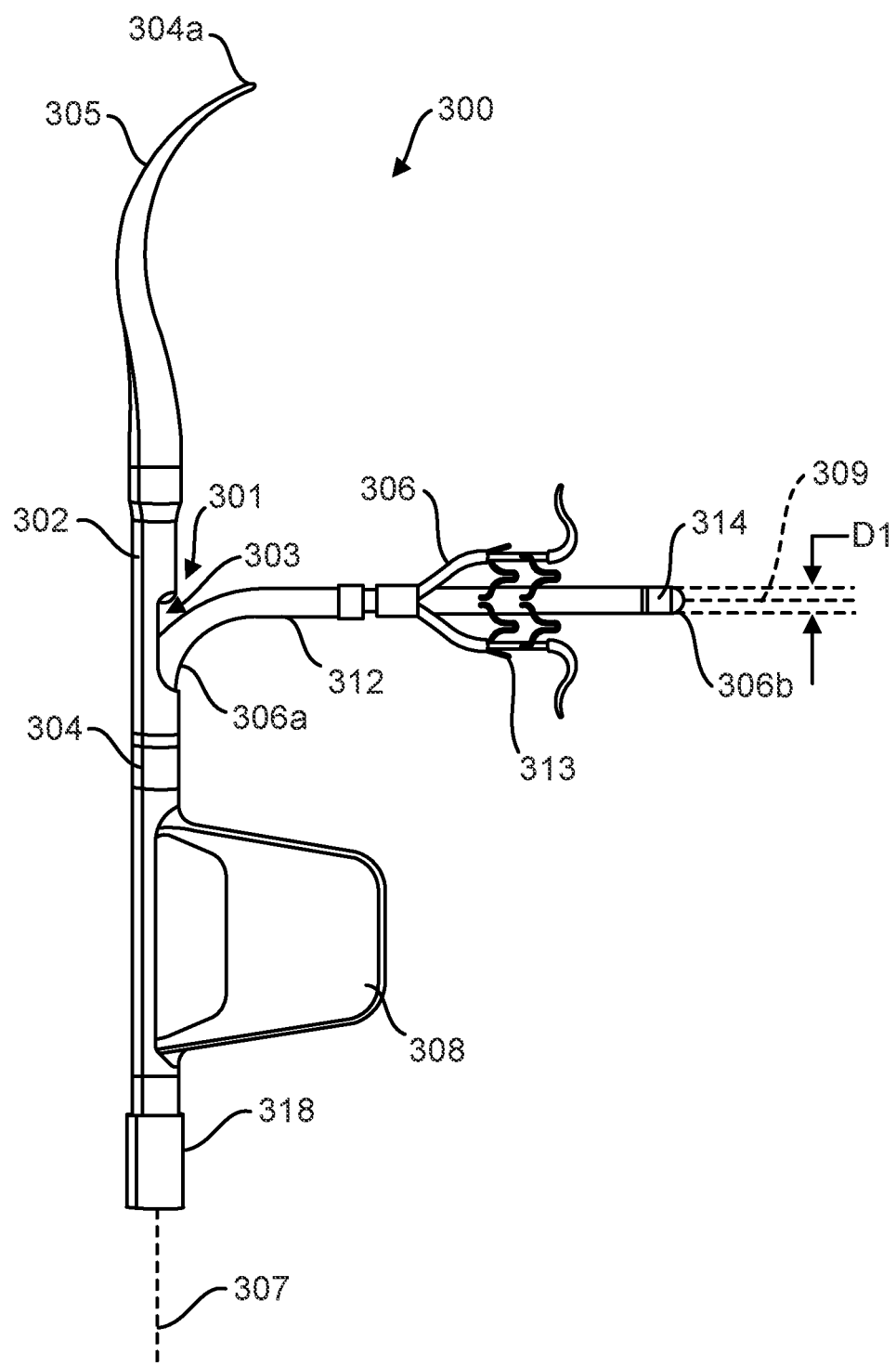
FIG. 3 is a schematic diagram of a side view of an example of a shunting catheter, in accordance with embodiments of the present disclosure.

FIG. 3 is a schematic diagram of a side view of an example of a shunting device 300, in accordance with embodiments of the present disclosure. FIG. 3 is merely an example. One of the ordinary skilled in the art would recognize many variations, alternatives, and modifications. As shown, the shunting device 300 includes a shunting catheter 302. In some embodiments, the shunting catheter 302 is configured to be delivered through a patient's coronary sinus (CS). In some embodiments, the shunting catheter 302 includes a catheter shaft 304, an ablation assembly 306, and an apposition element 308.

According to some embodiments, the shunting catheter 302 may be inserted through a small vein in the patient's body, and then tracked to the patient's right atrium (RA). In certain embodiments, once the shunting catheter 302 is in the patient's RA, the shunting catheter 302 may be maneuvered into the CS ostium to gain alignment in the CS at a target location of on a wall between the patient's CS and LA. In other embodiments, once the shunting catheter 302 is in the patient's RA, the shunting catheter 302 may be aligned at a target location of the patient's atrial septum (AS).

According to certain embodiments, the catheter shaft 304 is made of flexible material that may curve with the anatomy of the patient's CS. In certain embodiments, the catheter shaft 304 may include polyether block amide, nylon, silicone, and/or a combination thereof. In some instances, the catheter shaft 304 may be a multi-layered and multi-material component. In some instances, the shunting catheter 302 may be made from multiple materials that are reflow soldered together. In certain instances, the shunting catheter 302 may be made from multiple materials that are bonded together with an over mold. In certain embodiments, a portion of the shunting catheter 302 houses other components of the shunting device 300 that are configured to interact with the patient's anatomy.

In some embodiments, the catheter shaft 304 is reinforced with a braid and can have an etched or casted liner. In certain embodiments, the braid for reinforcing the catheter shaft 304 may be made of nitinol. In some embodiments, the liner may be made from polyetheretherketone (PEEK), polytetrafluoroethylene (PTFE), copolymers of polyamide and polyether, or a combination thereof. In certain embodiments, the catheter shaft 304 may be injection molded or extruded. In some embodiments, the catheter shaft 304 is coated for lubricity with a hydrophilic coating, or other types of coating suitable for coating a catheter shaft as known by a skilled person in the art.

In certain embodiments, the catheter shaft 304 may have multiple lumens. In embodiments, the multiple lumens may allow for the exchange and movement of various parts (for example, the ablation assembly 306, the apposition element 308) during deployment and/or shunting. In certain embodiments, the shunting catheter 302 is used to gain access into a patient's CS, the ablation assembly 306 including multiple lumens to gain access into the patient's LA.

According to some embodiments, the catheter shaft 304 has a distal end 304*a* and a proximal end (not shown). In some embodiments, the catheter shaft 304 may include a stabilizing element such as distal tip 305 at the distal end 304*a* that has a curve (for example, a pre-existing curve), for example, a curve conforming to the anatomy of a patient's CS. In some embodiments, the distal tip 305 may help with navigation when inserting the shunting catheter 302 into the patient's CS. In certain embodiments, the distal tip 305 may allow for proper positioning of the shunting catheter 302 during shunting. In some instances, the distal tip 305 may be made of a different material than other parts of the catheter shaft 304. In some instances, for example, the distal tip 305 may be made of a material more flexible than the material of other parts of the catheter shaft 304. In some embodiments, the distal tip 305 may be injection molded or machined to have a unique geometry (for example, a curve) for better stabilizing the catheter shaft 304 during deployment.

According to some embodiments, the distal tip 305 may have a length of from about 5 mm to about 85 mm. In certain embodiments, the catheter shaft 304 includes a shaft opening 303. In some embodiments, a portion of the catheter shaft 304 between the shaft opening 303 and the distal end 304*a* has a curve. In some embodiments, the catheter shaft 304 defines a first axis 307, and the ablation assembly 306 defines a second axis 309 at the second state after deployment. In certain embodiments, the second axis 309 and the first axis 307 form an angle greater than zero degrees. In certain embodiments, the second axis 309 and the first axis 307 form an angle greater than 10 degrees.

According to certain embodiments, the catheter shaft 304 includes a shaft lumen 301, and the ablation assembly 306 is disposed in the shaft lumen 301 at a first state (for example, during deployment to position of the ablation assembly 306). In certain embodiments, the ablation assembly 306 includes a proximal end 306*a* and a distal end 306*b*. In some embodiments, the ablation assembly 306 includes an ablation shaft 312, an ablation mechanism 313, and a puncture element 314. In certain embodiments, the ablation shaft 312 has a pre-determined curve. In certain embodiments, the ablation mechanism 313 is extended from the catheter shaft 304 at the proximal end 306a of the ablation assembly 306 at a second state (for example, a shunting state). In some embodiments, the ablation assembly 306 extends from the catheter shaft 304 through the shaft opening 303. In certain instances, the puncture element 314 has a diameter (D1) in the range of about 2 millimeters to about 5 millimeters. In some embodiments, once the shunting catheter 302 is in position after deployment, the puncture element 314 may be used to puncture through the wall between a patient's CS and LA.

According to certain embodiments, an energy source coupled to the shunting catheter 302 may provide energy (for example, electrical energy) to the shunting catheter 302, and the shunting catheter 302 may generate and deliver ablation energy (for example, radiofrequency (RF) energy, phased RF energy, cryogenic energy, thermal energy, pulse energy, laser energy, microwave energy, ultrasound energy, and/or the like) to a target location of the patient.

According to some embodiments, the puncture element 314 is disposed at the distal end 306b of the ablation assembly 306. In embodiments, the shaft opening 303 is not at the distal end 304a of the catheter shaft 304. In certain embodiments, the puncture element 314 has a configuration of regular trocar point, regular taper point, regular taper cutting, regular reverse cutting edge, regular diamond point, regular conventual cutting edge, regular blunt taper point, premium lancet point, premium diamond point, or premium cutting edge. In certain embodiments, the puncture element 314 is made of materials including nitinol, stainless steel, cobalt chromium, aluminum, and/or a combination thereof.

In embodiments, the ablation assembly 306 is configured to deliver ablation energy to a target tissue during shunting. In certain embodiments, the ablation energy delivered by the ablation assembly 306 may include radiofrequency (RF) energy, phased RF energy, cryogenic energy, thermal energy, pulse energy, laser energy, microwave energy, ultrasound energy, and/or the like. In certain embodiments, the energy delivered by the ablation assembly 306 punctures through tissue surrounding the target location to create an opening at the target location. In some embodiments, the energy delivered by the ablation assembly 306 ablates tissue surrounding the target location to solidify an opening at the target location. In certain embodiments, delivering energy via the ablation assembly 306 helps prevent tissue regrowth around the created shunt after the procedure.

According to some embodiments, the shunting catheter 302 further includes an outer shaft 318 disposed outside of at least a part of the catheter shaft 304 during deployment. In some embodiments, the outer shaft 318 is made of flexible material that may curve with the anatomy of the patient's CS. In certain embodiments, for example, the outer shaft 318 may include polyether block amide, nylon, silicone, or a combination thereof. In some instances, the outer shaft 318 may be a multi-layered and multi-material component.

In some examples, the outer shaft 318 is reinforced with a braid and can have an etched or casted liner. In some embodiments, the braid for reinforcing the catheter shaft 304 may be made of nitinol. In certain embodiments, the liner may be made from polyetheretherketone (PEEK), polytetrafluoroethylene (PTFE), copolymers of polyamide and polyether, or a combination thereof. In some instances, the outer shaft 318 may include a reinforcing element (for example, a laser-cut tube). In certain embodiments, the outer shaft 318 may be injection molded or extruded. In some embodiments, the catheter shaft 304 is coated for lubricity with a hydrophilic coating, or other types of coating suitable for coating a catheter shaft as known by a skilled person in the art.

In certain examples, the outer shaft 318 and/or the catheter shaft 304 may house all of the catheter components until the desired target location is reached. In some embodiments, once the shunting catheter 302 has reached the target location, the outer shaft 318 may translate towards the proximal end of the catheter shaft 304 to expose the ablation assembly 306 and other components.

According to certain embodiments, the apposition element 308 is disposed within the outer shaft 318 at a first state (for example, during deployment). In embodiments, the apposition element 308 protrudes from the catheter shaft 304 during deployment. In certain embodiments, the apposition element 308 is flexible and compressed to fit within the outer shaft 318, and configured to decompress and protrude from the catheter shaft 304 during deployment. In some embodiments, the apposition element 308 is disposed proximate to the ablation assembly 306 and/or the one or more shaft openings 303. In some instances, the apposition element 308 is a braided structure including one or more nickel titanium wires. In some instances, the apposition element 308 is made of a flexible material having a portion protruding from the catheter shaft 304. In some examples, the flexible material may be a foam. In some instances, the flexible material may be a balloon filled with a contrast solution that is visible under fluoroscopy. In some instances, the flexible material may be a polymer with a radiopaque marker added for visualization. In some embodiments, the radiopaque marker may include tantalum, platinum, gold, palladium, platinum-iridium or any radiopaque marker known by a skilled person in the art.

In certain embodiments, the apposition element 308 is configured to appose at least one wall in a patient's cardiovascular system (for example, CS, LA, etc.) such that the shunting catheter 302 is stabilized in one position once deployed. In some embodiments, the apposition element 308 is configured to appose two or more walls in a patient's cardiovascular system. According to some embodiments, the apposition element 308 has several benefits, one of which is the stabilization of catheter 302 after deployment. In some embodiments, any movement or lack thereof the protruding element (for example, a braided element) provides an estimated distance of how far the catheter 302 is away from the vessel wall of patient's CS. In addition, in instances where the apposition element 308 includes a braided element, such that when the braided element is apposing the vessel wall of a patient's CS, the openings between the braids still allow blood flow through the apposition element 308, thus reducing the risk of thrombus formation caused by any occlusion in the vessel.

The apposition element 308 may be made of nitinol, and is reflow soldered or bonded to the catheter shaft 304. In some embodiments, the apposition element 308 serves the purpose of pushing against the back wall of a patient's CS, to allow for the shunting catheter 302 to translate forward and against target location on a wall between patient's CS and LA. In certain embodiments, the apposition element 308 may include an elastic braided structure, and may thus expand and compress with force applied by the outer shaft 318, or through other mechanical means.

In some embodiments, for example as shown, the apposition element 308 is disposed on the same side of the catheter shaft 304 as the ablation assembly 306. In some embodiments, the apposition element 308 may be on an opposite side of the catheter shaft 304 from the ablation assembly 306. In certain embodiments, the apposition element 308 may be configured to appose the wall between patient's CS and LA, instead of the back of patient's CS wall. In certain embodiments, this may allow the shunting device 300 to then penetrate through the patient's CS wall to gain access into the patient's LA. In embodiments, the apposition element 308 helps stabilize and position the shunting catheter 302 in the patient's CS at a target location.

Figure 4B:
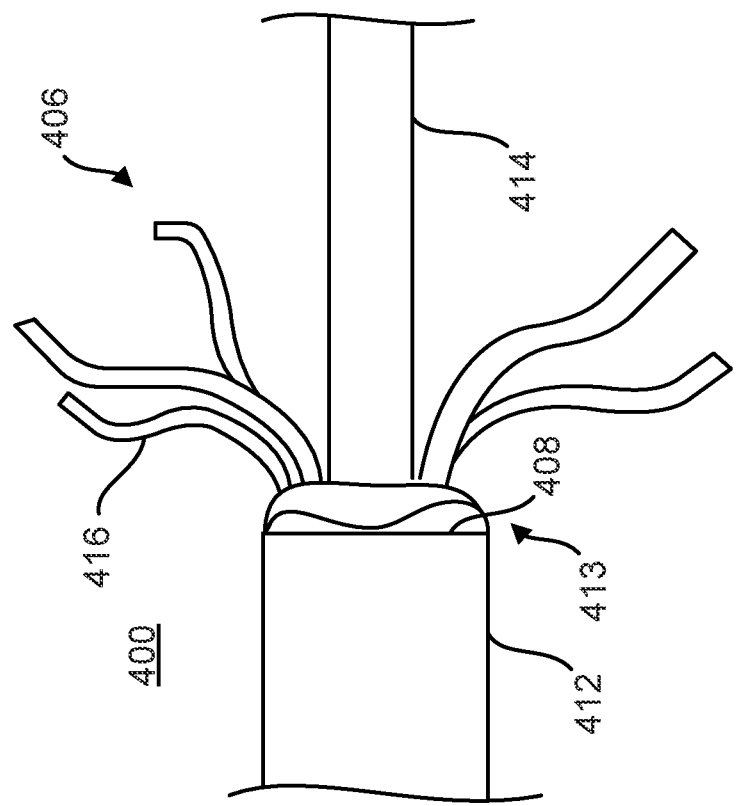
FIGS. 4A-4C are schematic diagrams of side views of an example of a shunting catheter, in accordance with embodiments of the present disclosure.
Figure 4A:
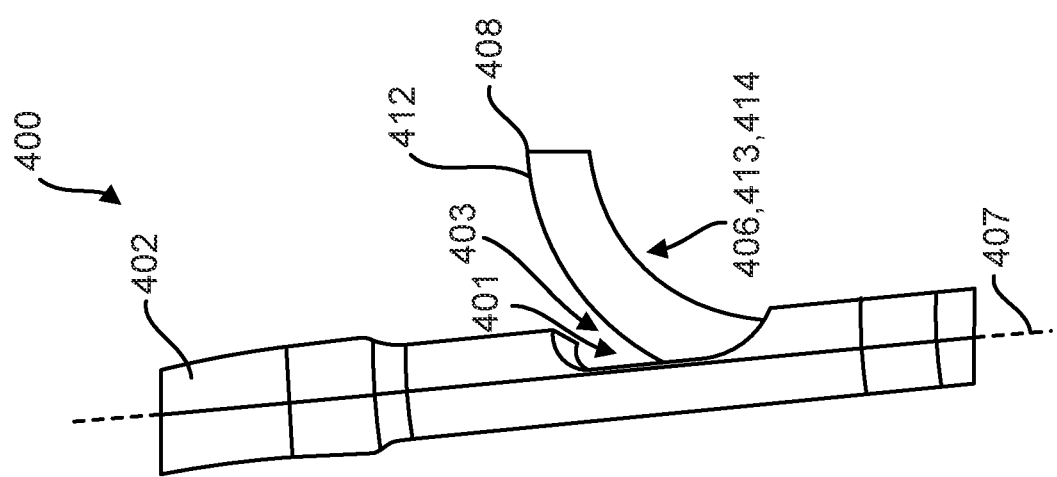
Figure 4C:
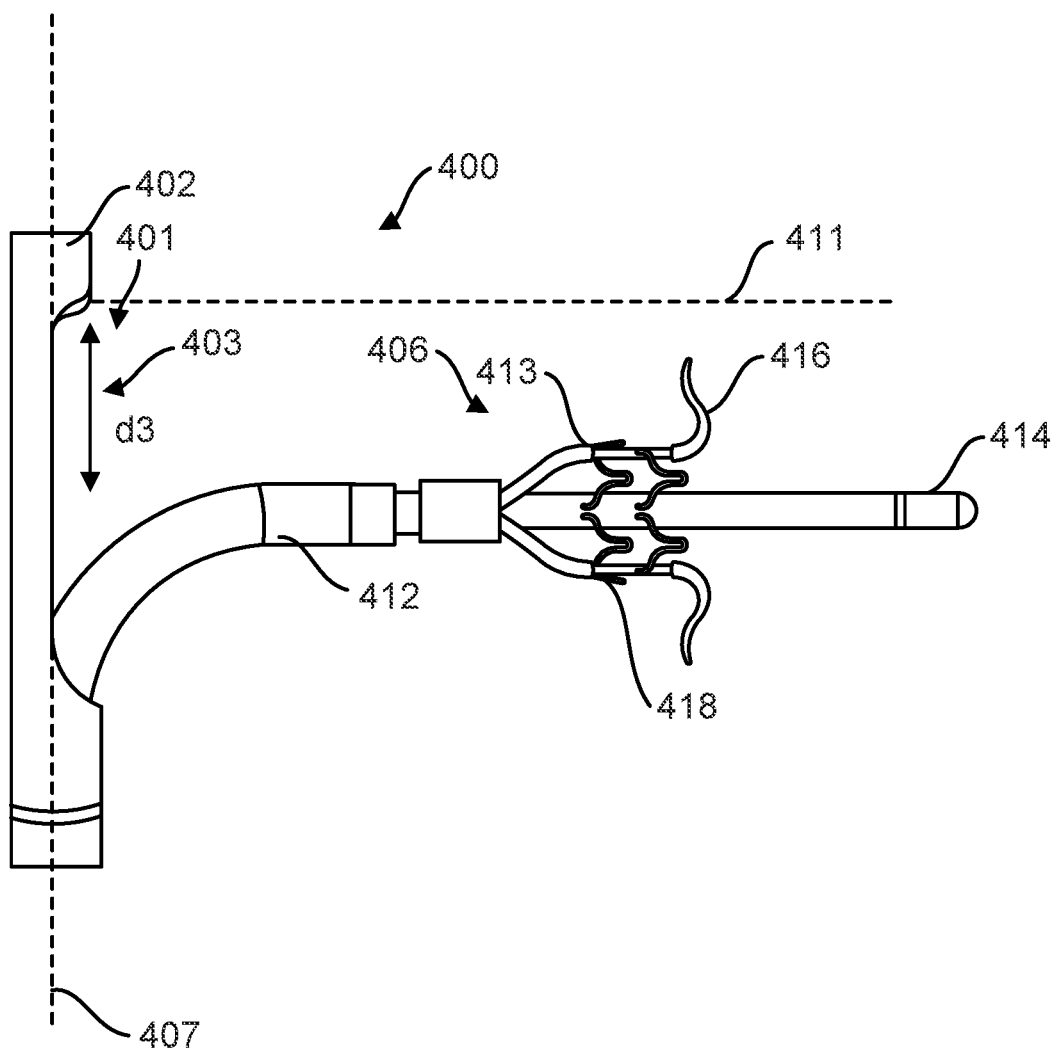

FIGS. 4A-4C are schematic diagrams of side views of an example of a shunting catheter 400, in accordance with embodiments of the present disclosure. In some embodiments and as shown in FIGS. 4A-4C, the shunting catheter 400 includes a catheter shaft 402 having a shaft lumen 401, a shaft opening 403, and an ablation assembly 406 disposed within the shaft lumen 401 at a first state (for example, during deployment to position the ablation assembly 406) and extended from the shaft lumen 401 at a second state (for example, as shown in FIGS. 4A-4C). In some embodiments, the shunting catheter 400 includes a crimping shaft 412 having a predetermined curve for an ablation mechanism 413 to deploy, and a puncture element 414.

According to some embodiments, the ablation assembly 406 may have a telescoping feature (for example, the ablation mechanism 413 and the puncture element 414 being retractable into the crimping shaft 412, as shown in FIG. 4A) to allow the blunt distal end 408 of the crimping shaft 412 to contact the wall between the patient's LA and CS, or the patient's AS, before the puncture element 414 is translated forward to make contact with the wall between the patient's LA and CS, or the patient's AS. In certain embodiments, the telescoping feature of the ablation assembly 406 allows for a safe delivery of the puncture element 414 to the target location.

According to certain embodiments, the ablation assembly 406 of the shunting catheter 400 has a first deployment state (for example, shown in FIG. 4A), a second deployment state (for example, shown in FIG. 4B), and a third deployment state (for example, shown in FIG. 4C). In some embodiments, at the first deployment state the ablation mechanism 413 and the puncture element 414 are retracted in a lumen of the crimping shaft 412. In certain embodiments, at the first deployment state a plurality of positioning elements 416 and a plurality of expandable struts 418 of the ablation mechanism 413 (shown in FIGS. 4C) and the puncture element 414 are retracted in the lumen of the crimping shaft 412. In some embodiments, at the second deployment state the ablation mechanism 413 and the puncture element 414 are partially extended from a distal end 408 of the crimping shaft 412. In certain embodiments, at the second deployment state the plurality of positioning elements 416 of the ablation mechanism 413 and the puncture element 414 are extended from the distal end 408 of the crimping shaft 412, and the plurality of expandable struts 418 of the ablation mechanism 413 are retracted in the lumen of the crimping shaft 412. In some embodiments, at the third deployment state the ablation mechanism 413 and the puncture element 414 are further extended from the distal end 408 of the crimping shaft 412. In certain embodiments, at the third deployment state the plurality of positioning elements 416 and the plurality of expandable struts 418 of the ablation mechanism 413 and the puncture element 414 are extended from the distal end 408 of the crimping shaft 412.

In certain embodiments, the shaft opening 403 includes an edge defining an opening axis 411. In some embodiments, the opening axis 411 may be generally perpendicular to a first axis 407 along the catheter shaft 402. In some embodiments, the distance (d3) between the opening axis 411 and a second axis 409 along the ablation assembly 406 may be from about 0 mm to about 20 mm.

Figure 5:
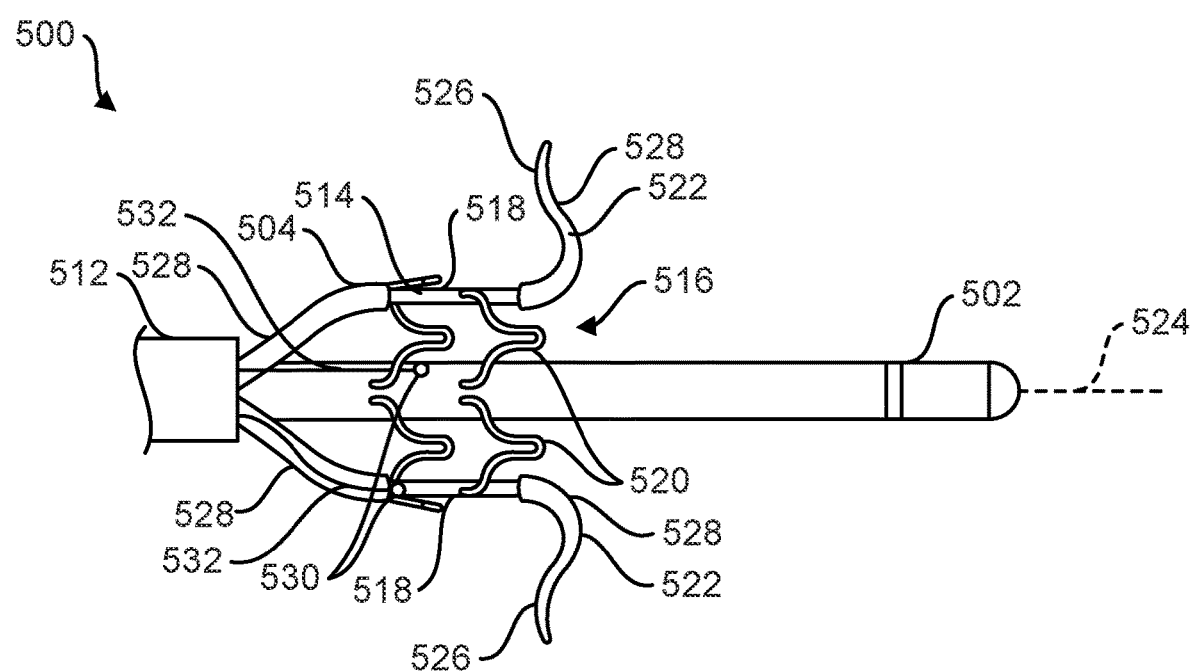
FIG. 5 is a schematic diagram of a side view of an example of an ablation assembly, in accordance with embodiments of the present disclosure.

FIG. 5 is a schematic diagram of a view of an example of an expandable ablation assembly 500, in accordance with embodiments of the present disclosure. In certain embodiments, the ablation assembly 500 may include a puncture element 502 and an ablation mechanism 504. In some embodiments, the puncture element 502 may be configured to puncture an opening at a target location in a patient, such as a vessel wall, more specifically the wall between the CS and LA of the patient, or the AS of the patient. In certain embodiments, the ablation mechanism 504 has a length in a range of 3 mm to 20 mm when fully expanded. In certain embodiments, the ablation mechanism 504 has an expanded diameter in a range of 2 mm to 12 mm at a cage 514 and 4 mm to 30 mm at positioning elements 522.

According to some embodiments, the puncture element 502 (for example, a needle) may take on many different needle configurations. Configurations for the puncture element 502 may include, but not are not limited to, regular trocar point, regular taper point, regular taper cutting, regular reverse cutting edge, regular diamond point, regular conventual cutting edge, regular blunt taper point, premium lancet point, premium diamond point, and/or premium cutting edge. In certain embodiments, the puncture element 502 is made of materials including nitinol, stainless steel, cobalt chromium, aluminum, and/or a combination thereof. In certain embodiments, the puncture element 502 physically contacts tissue to puncture an opening at the target location in the patient. In certain embodiments, the puncture element 502 receives energy from an energy source and delivers ablation energy (such as radiofrequency (RF) energy, phased RF energy, cryogenic energy, thermal energy, pulse energy, laser energy, ultrasound energy, microwave energy, and/or the like) to tissue to puncture an opening at the target location in the patient.

In certain embodiments, the ablation mechanism 504 and the puncture element 502 are together slidable into and out of a lumen of a crimping shaft 512. In certain embodiments, after the puncture element 502 forms an opening in the tissue at a target location in a patient, the ablation mechanism 504 expands to enlarge the opening in the tissue. In some embodiments, the ablation mechanism 504 then receives energy from an energy source and delivers ablation energy (such as radiofrequency (RF) energy, phased RF energy, cryogenic energy, thermal energy, pulse energy, laser energy, ultrasound energy, microwave energy, and/or the like) to ablate the tissue and thereby solidify the opening at the target location.

In some embodiments, the ablation mechanism 504 includes an expandable cage 514, and the expandable cage 514 is fixedly coupled at its proximal end to the puncture element 502. In certain embodiments, the expandable cage 514 includes an open distal end 516 (that is, being disposed apart from the puncture element 502). In certain embodiments, the expandable cage 514 is made of one or more materials that facilitate self-expansion, such as nitinol, or one or more other materials, such as stainless steel, titanium, platinum-iridium, or cobalt-chromium.

In certain embodiments and as illustrated, the expandable cage 514 includes a plurality of expandable struts 518. In some embodiments, the struts 518 are collapsed radially inwardly, or toward each other, when the ablation mechanism 504 is disposed in the crimping shaft 512 (that is, in a first state; not specifically illustrated). In certain embodiments, the struts 518 expand radially outwardly, or away from each other, when the ablation mechanism is disposed outside of the crimping shaft 512 (that is, in a second state, as illustrated in FIG. 5). In certain embodiments, the expandable cage 514 includes two, three, four, five, six, seven, eight, nine, ten, or more expandable struts 518. In certain embodiments and as illustrated, the struts 518 are self-expanding (for example, by being made of a shape memory material and set in the expanded state). In certain embodiments, the self-expansion of the struts 518 may be controlled by a constrainer, such as a plurality of sutures (for example, thin strands) coupled to the struts 518. Such a constrainer may be reconfigured from a constraining state to a release state to permit the struts 518 to expand, and the constrainer may be reconfigured from the release state to the constraining state to collapse the struts 518. In some embodiments, the constrainer may be coupled to distal ends of the struts. In certain embodiments, the struts 518 are expanded by an actuator, such as an inflatable balloon (not shown). In certain embodiments, an actuator may be disposed in a cavity of the cage 514 formed between the struts 518. In certain embodiments, one or more additional components, such as control wires coupled to the actuators, may be disposed in the cavity of the cage 514 and extend through the ablation shaft 508.

In certain embodiments and as illustrated, the expandable cage 514 includes a plurality of connector struts 520. In some embodiments, each connector strut 520 is disposed between and couples adjacent expandable struts 518. In certain embodiments, the connector struts 520 are integrally formed with the expandable struts 518.

In some embodiments, the ablation mechanism 504 further includes a plurality of positioning elements 522 coupled to and disposed distally relative to the expandable struts 518. In certain embodiments, the positioning elements 522 are disposed outwardly from the expandable cage 514, or radially outwardly from the expandable struts 518, relative to a longitudinal axis 524 defined by the puncture element 502, at a second state (for example, as shown in FIG. 5). In some embodiments, the positioning elements 522 contact tissue at a target location of a patient and thereby properly position the ablation mechanism 504 at the target location of the patient. In certain embodiments, one or more of the positioning elements 522 includes a curved shape. In some embodiments, one or more of the positioning elements 522 more specifically includes a curved distal end 526 that defines a soft landing zone configured to atraumatically contact tissue at the target location of the patient.

In certain embodiments, the expandable cage 514 includes two, three, four, five, six, seven, eight, nine, ten, or more positioning elements 522. In some embodiments, the ablation mechanism 504 includes the same number of expandable struts 518 and positioning elements 522, more specifically each expandable strut 518 couples to a single positioning element 522. In some embodiments, the ablation mechanism 504 includes fewer positioning elements 522 than expandable struts 518, more specifically one or more expandable struts 518 do not couple to a positioning element 522.

In certain embodiments, the positioning elements 522 are constructed of a flexible material. In some embodiments, the positioning elements 522 are constructed of one or more materials that facilitate self-expansion, such as nitinol, or one or more other materials, such as stainless steel, titanium, platinum-iridium, cobalt-chromium, or flexible plastics. In certain embodiments, one or more of the positioning elements 522 are each integrally formed with one of the expandable struts 518 and constructed of the same material(s) as the expandable cage 514.

In some embodiments, one or more of the expandable struts 518 contact tissue at a target location within a patient and act as electrodes to deliver ablation energy to the tissue. In certain embodiments, one or more portions of the ablation mechanism 504 may carry an insulator 528 (such as a heat shrink tube, a polytetrafluoroethylene (PTFE) coating, an expanded polytetrafluoroethylene (ePTFE) coating, a polyimide coating, or the like) to inhibit delivery of ablation energy to the blood of the patient. In some embodiments, the insulator 528 covers proximal portions of one or more of the expandable struts 518 and/or the positioning elements 522. In certain embodiments, the insulator 528 may be coupled to the expandable cage 514 and the positioning elements 522 in a dip coating process. In some embodiments, the expandable cage 514 and the positioning elements 522 may be completely coated by the insulator 528, and the insulator 528 may then be removed from portions of the expandable cage 514 intended to deliver ablation energy. In certain embodiments, portions of the expandable cage 514 intended to deliver ablation energy may first be masked, the remainder of the expandable cage 514 and the positioning elements 522 may be coated by the insulator 528, and the mask may then be removed from the expandable cage 514. In certain embodiments, the insulator 528 may have a thickness in a range of 0.0005 inches to 0.008 inches, more specifically about 0.004 inches. In alternative embodiments, the expandable cage 514 carries an electrode structure, such as a thin film electrode, including one or more electrodes (not shown) for delivering ablation energy to the tissue of the patient. In certain embodiments, one or more lead wires (not shown) couple the expandable cage 514 or the electrode structure to an energy source. In some embodiments, the lead wires may extend through the crimping shaft 512 or outside of the crimping shaft 512.

In certain embodiments and as illustrated, the ablation mechanism 504 further includes one or more temperature sensors 530. In some embodiments, the temperature sensors 530 facilitate monitoring and/or controlling ablation, for example, by notifying a user and/or automatically inhibiting delivery of ablation energy upon detecting relatively high ablation temperatures. In some embodiments, the temperature sensors 530 may be thermocouples (type K thermocouples, type T thermocouples, or the like), resistance temperature detectors (RTDs), negative temperature coefficient (NTC) thermistors, semiconductor-based sensors, other types of thermistors, or the like. In certain embodiments, one or more lead wires 532 couple the temperature sensors 530 to a controller. In some embodiments, one or more of the lead wires 532 may extend through the insulators 528 to couple the temperature sensors 530 to the expandable cage 514. In certain embodiments, the temperature sensors 530 are trapped by the insulators 528 to couple the sensors 530 to the expandable cage 514. In some embodiments, the temperature sensors 530 are coupled to the expandable cage 514 via an adhesive, for example, an epoxy or a UV light-cured adhesive. In certain embodiments, one or more of the lead wires 532 may extend through and/or the temperature sensors 530 may be positioned in structures of the expandable cage 514, for example, "loops" (not shown), to couple the temperature sensors 530 to the expandable cage 514. In some embodiments, the ablation mechanism 504 includes various numbers of temperature sensors 530, such as one, two, three, four, five, or six temperature sensors 530. In certain embodiments, one or more of the temperature sensors 530 has a size between 46 and 22 AWG.

Figure 6A:
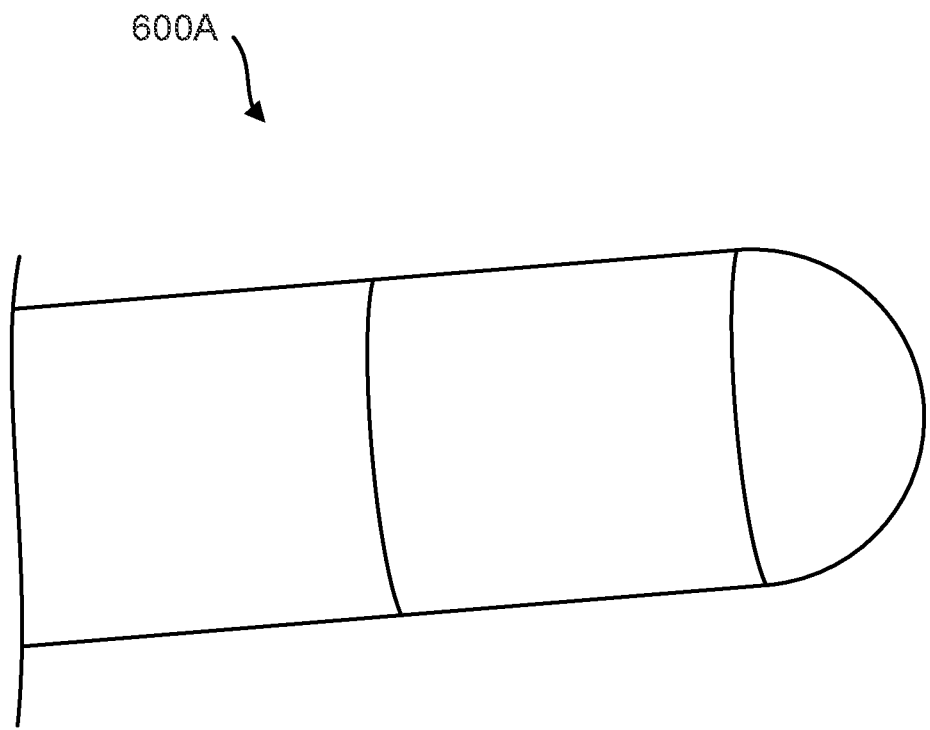
FIGS. 6A-6B are schematic diagrams of side views of examples of puncture elements, in accordance with embodiments of the present disclosure.
Figure 6B:
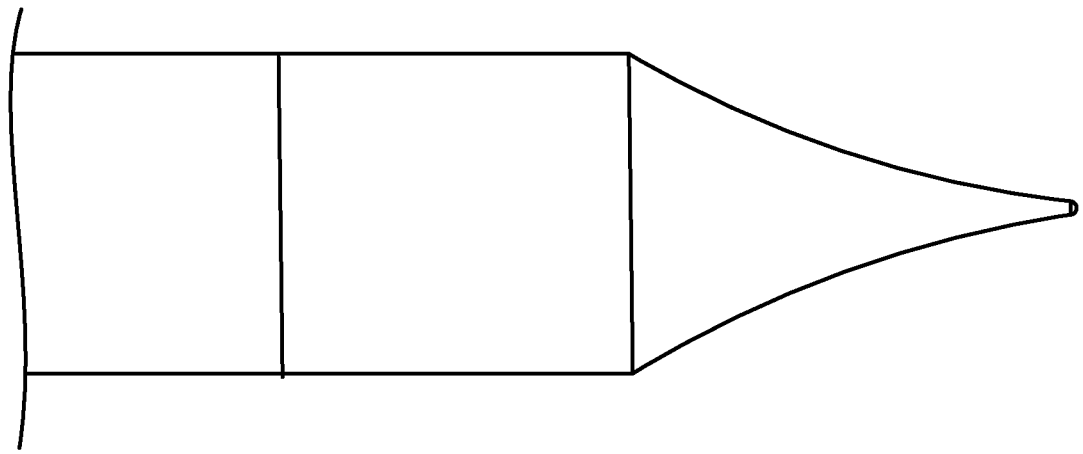

FIGS. 6A-6B are schematic diagrams of side views of examples of puncture elements 600A and 600B of ablation assemblies, in accordance with embodiments of the present disclosure. In certain embodiments, the puncture elements 600A and 600B are made of materials including nitinol, stainless steel, cobalt chromium, aluminum, and/or a combination thereof. In certain embodiments, the puncture elements 600A and 600B may have outer diameters in a range of 0.02 in. to 0.08 in., more specifically about 0.07 in. In some embodiments, the puncture elements 600A and 600B may be coupled to pull wires (not shown) to facilitate bending and steering.

According to some embodiments, for example as shown in FIG. 6A, the puncture element 600A has a rounded tip shape. In certain embodiments, the puncture element 600A has a hemispherical tip shape. Such a tip shape may facilitate delivering ablation energy (such as radiofrequency (RF) energy, phased RF energy, cryogenic energy, thermal energy, pulse energy, laser energy, ultrasound energy, microwave energy, and/or the like) to ablate tissue at a target location within a patient (for example, the wall between the patient's LA and CS, or the patient's AS).

According to some embodiments, for example as shown in FIG. 6B, the puncture element 600B has a pointed tip shape. In certain embodiments, the puncture element 600B includes a regular trocar pointed shape. Such a tip shape may facilitate physically contacting tissue to puncture an opening at a target location within a patient (for example, the wall between the patient's LA and CS, or the patient's AS).

Figure 7:
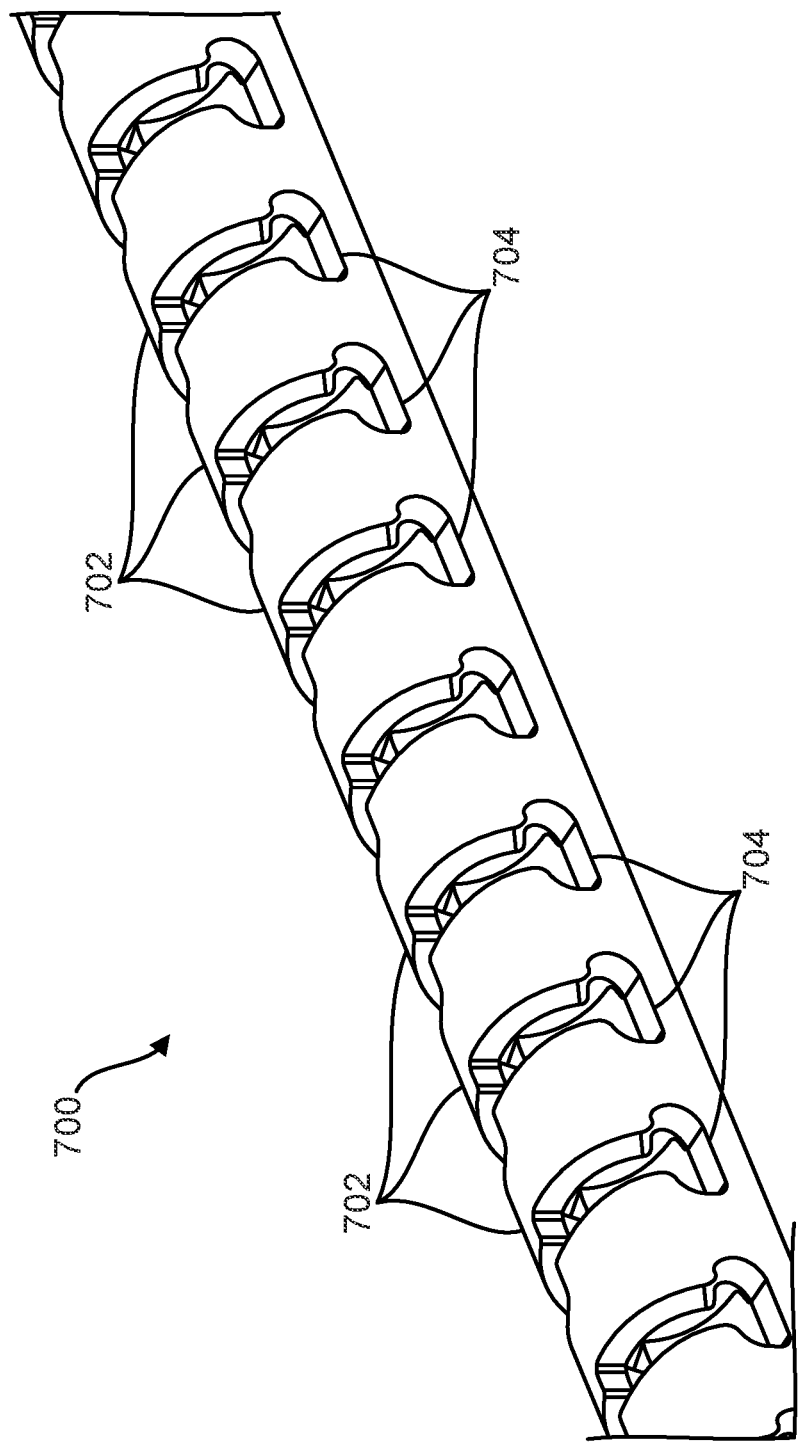
FIG. 7 is a schematic diagram of a perspective view of an example of an inner member of an ablation shaft, in accordance with embodiments of the present disclosure.

FIG. 7 is a schematic diagram of a perspective view of an example of an inner member 700 of an ablation shaft, in accordance with embodiments of the present disclosure. In some embodiments, the inner member 700 is coupled to a puncture element and/or an ablation mechanism (not shown). In certain embodiments, the inner member 700 is made of materials including nitinol, stainless steel, cobalt chromium, aluminum, and/or a combination thereof. In certain embodiments, the inner member 700 is bendable and steerable via one or more pull wires (not shown). In some embodiments, to facilitate such bending and steering, the inner member 700 may be hollow and include a plurality of ribs 702 separated by voids 704. In alternative embodiments, the inner member 700 may have a different structure.

Figure 8:
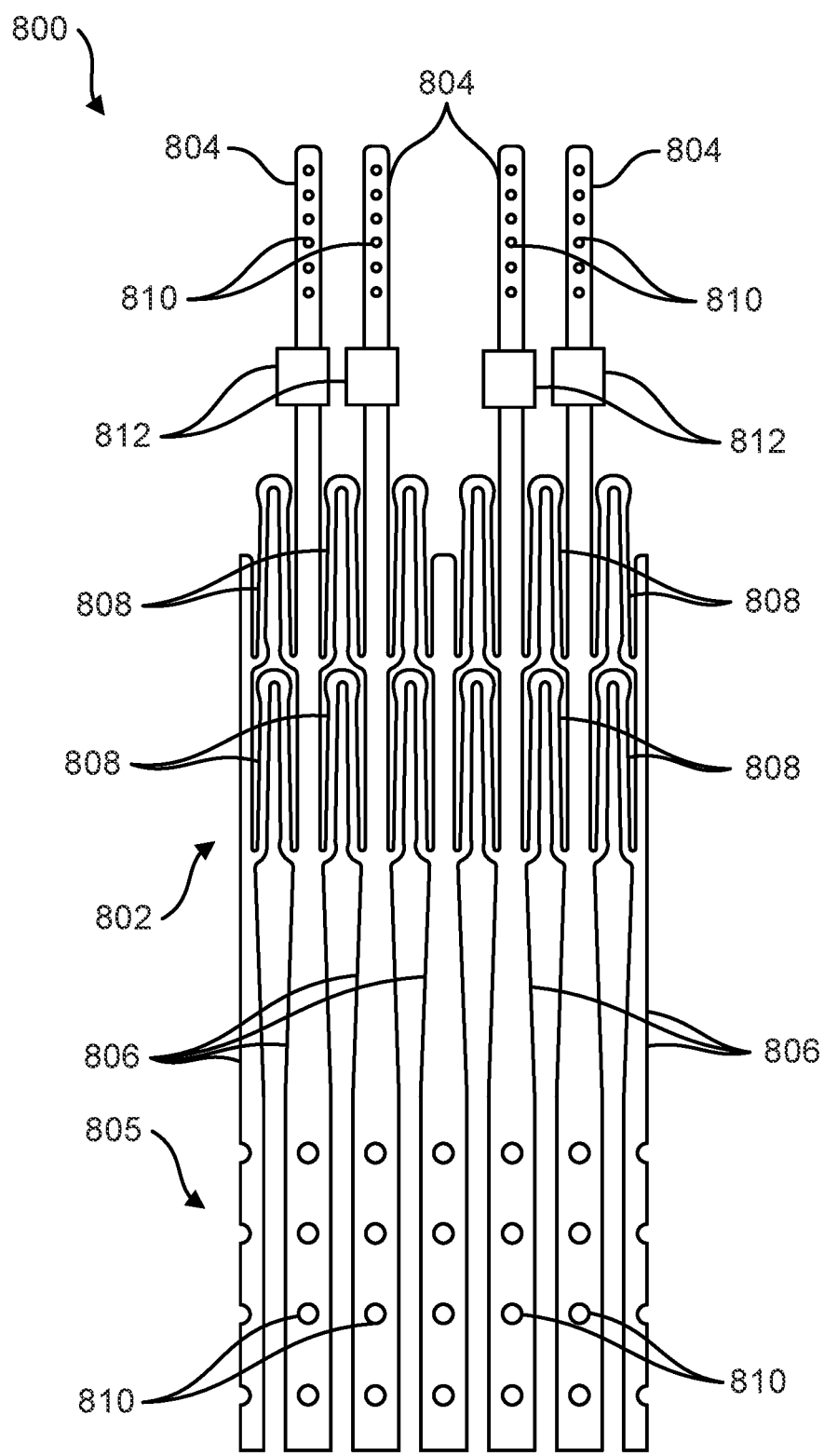
FIG. 8 is a schematic diagram of a side view of an example of an ablation mechanism pattern, in accordance with embodiments of the present disclosure.

FIG. 8 is a schematic diagram of a side view of an example of an ablation mechanism pattern 800 including an expandable cage 802 and positioning elements 804, in accordance with embodiments of the present disclosure, which may be used to program a laser to cut a tube (not shown), such as a metal tube, into an appropriate shape. In certain embodiments, the tube is constructed of one or more materials that facilitate self-expansion, such as nitinol, or one or more other materials, such as stainless steel, titanium, platinum-iridium, or cobalt-chromium. In certain embodiments, the ablation mechanism pattern 800 includes a proximal collar 805 for coupling to an ablation shaft.

According to certain embodiments, the expandable cage 802 includes a plurality of expandable struts 806. In certain embodiments and as illustrated, the expandable cage 802 includes six expandable struts 806, one of the struts 806 being divided into two halves in the pattern 800. In other embodiments, the expandable cage 802 includes a different number of expandable struts 806, such as two, three, four, five, seven, eight, nine, ten, or more expandable struts 806.

In some embodiments, the expandable struts 806 are collapsed radially inwardly, or toward each other, when the tube formed using the ablation mechanism pattern 800 is disposed in a crimping shaft (that is, in a first state; not specifically illustrated). In certain embodiments, the struts 806 expand radially outwardly, or away from each other, when the tube formed using the ablation mechanism pattern 800 is disposed outside of the crimping shaft (that is, in a second state, not specifically illustrated). In certain embodiments and as illustrated, the struts 806 are self-expanding. In certain embodiments, the self-expansion of the struts 806 may be controlled by a constrainer, such as a plurality of sutures (for example, thin strands) coupled to the struts 806. Such a constrainer may be reconfigured from a constraining state to a release state to permit the struts 806 to expand, and the constrainer may be reconfigured from the release state to the constraining state to collapse the struts 806. In some embodiments, the constrainer may be coupled to distal ends of the struts. In certain embodiments, the struts 806 are expanded by an actuator, such as an inflatable balloon (not shown). In certain embodiments, an actuator may be disposed in a cavity of the cage 802 formed between the struts 806. In certain embodiments, one or more additional components, such as control wires coupled to the actuators, may be disposed in the cavity of the cage 802.

In certain embodiments and as illustrated, the expandable cage 802 includes a plurality of connector struts 808. In some embodiments, each connector strut 808 is disposed between and couples adjacent expandable struts 806. In certain embodiments, the connector struts 808 are integrally formed with the expandable struts 806.

In some embodiments, the ablation mechanism pattern 800 further includes the positioning elements 804, which are coupled to and disposed distally relative to the expandable struts 806. In certain embodiments, the positioning elements 804 are disposed outwardly from the expandable cage 802, or radially outwardly from the expandable struts 806, relative to a longitudinal axis defined by the ablation shaft, at a second state (not specifically illustrated). In some embodiments, the positioning elements 804 contact tissue at a target location of a patient and thereby properly position the tube formed using the ablation mechanism pattern 800 at the target location of the patient.

In certain embodiments, the expandable cage 802 includes two, three, four, five, six, seven, eight, nine, ten, or more positioning elements 804. In some embodiments, the ablation mechanism pattern 800 includes the same number of expandable struts 806 and positioning elements 804, more specifically each expandable strut 806 couples to a single positioning element 804. In some embodiments, the ablation mechanism pattern 800 includes fewer positioning elements 804 than expandable struts 806, more specifically one or more expandable struts 806 do not couple to a positioning element 804.

In certain embodiments, the positioning elements 804 are constructed of a flexible material. In some embodiments, the positioning elements 804 are constructed of one or more materials that facilitate self-expansion, such as nitinol, or one or more other materials, such as stainless steel, titanium, platinum-iridium, cobalt-chromium, or flexible plastics. In certain embodiments, one or more of the positioning elements 804 are each integrally formed with one of the expandable struts 806 and constructed of the same material(s) as the expandable cage 802. In some embodiments, one or more of the positioning elements 804 are constructed of or include a radiopaque material.

In some embodiments, one or more of the expandable struts 806 contact tissue at a target location within a patient and act as electrodes to deliver ablation energy to the tissue. In certain embodiments, one or more portions of the tube formed by the ablation mechanism pattern 800 may carry an insulator (not shown; such as a heat shrink tube, a polytetrafluoroethylene (PTFE) coating, an expanded polytetrafluoroethylene (ePTFE) coating, a polyimide coating, or the like) to inhibit delivery of ablation energy to the blood of the patient. In some embodiments, the insulation is applied onto the electrode through the manufacturing method of dip coated, spray coating, electrospinning, lamination, heat shrinkage, or the like. In some embodiments, the insulator covers proximal portions of one or more of the expandable struts 806 and/or the positioning elements 804. In certain embodiments, the expandable cage 802 and/or the positioning elements 804 may include anchor structures that facilitate coupling to the insulator. In some embodiments and as illustrated, one or more of the expandable struts 806 and one or more of the positioning elements 804 include apertures 810 to facilitate coupling to the insulator. In certain embodiments and as illustrated, one or more of the positioning elements 804 include protrusions 812 to facilitate coupling to the insulator. In some embodiments, additional or alternative features couple the insulator to the ablation mechanism, such as sutures and/or adhesives. In certain embodiments, the insulator may have a thickness in a range of 0.0005 inches to 0.008 inches, more specifically about 0.004 inches. In alternative embodiments, the expandable cage 802 carries an electrode structure, such as a thin film electrode, including one or more electrodes (not shown) for delivering ablation energy to the tissue of the patient. In certain embodiments, one or more lead wires (not shown) couple the expandable cage 802 or the electrode structure to an energy source. In some embodiments, the lead wires may extend through the crimping shaft or outside of the crimping shaft.

Figure 9A:
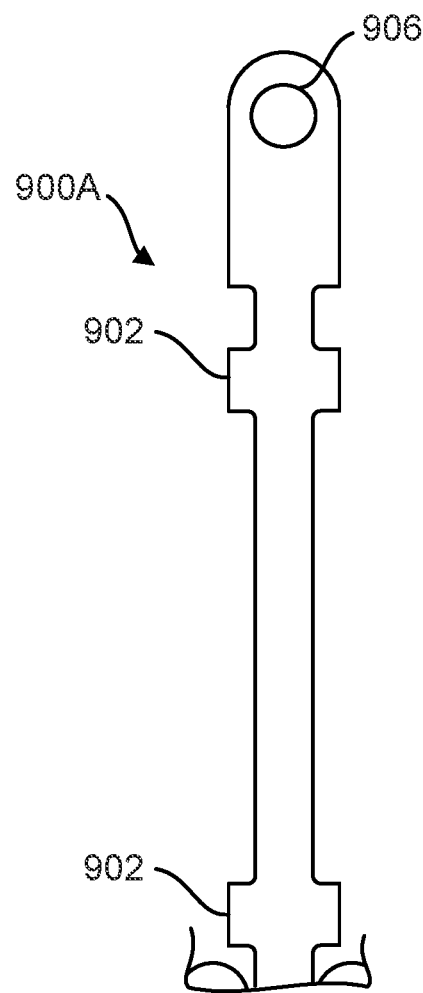
FIGS. 9A-9B are schematic diagrams of side views of examples of positioning elements, in accordance with embodiments of the present disclosure.
Figure 9B:
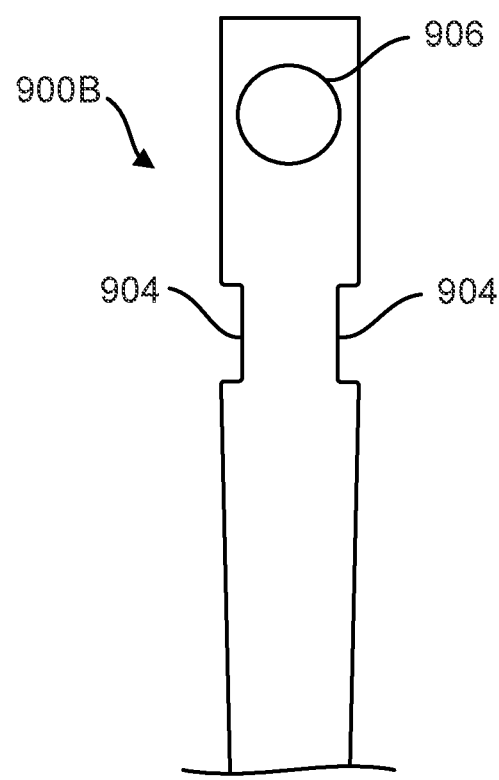

FIGS. 9A-9B are schematic diagrams of side views of examples of positioning elements 900A and 900B of ablation assemblies, in accordance with embodiments of the present disclosure. In certain embodiments, the positioning elements 900A and 900B form part of ablation mechanisms (not shown). In some embodiments, the positioning elements 900A and 900B are coupled to expandable cages (not shown) of ablation mechanisms. In certain embodiments, the positioning elements 900A and 900B are integrally formed with and constructed of the same material as expandable cages of ablation mechanisms.

In certain embodiments, one or more portions of the positioning elements 900A and 900B carry an insulator (not shown; such as a heat shrink tube, a polytetrafluoroethylene (PTFE) coating, an expanded polytetrafluoroethylene (ePTFE) coating, a polyimide coating, or the like) to inhibit delivery of ablation energy to the blood of the patient. In certain embodiments, the positioning elements 900A and 900B include anchor structures that facilitate coupling to the insulator. According to some embodiments, for example as shown in FIG. 9A, the positioning element 900A includes one or more protrusions 902 to facilitate coupling to the insulator. According to some embodiments, for example as shown in FIG. 9B, the positioning element 900B includes and one or more indentations 904 to facilitate coupling to the insulator. In certain embodiments, the positioning elements 900A and 900B carry one or more radiopaque markers (not shown) to facilitate visualization of the positioning elements 900A and 900B under fluoroscopy. In some embodiments, the one or more radiopaque markers are constructed of platinum, platinum-iridium, gold, tantalum, palladium, or the like. In certain embodiments, the one or more radiopaque markers can ball-shaped, puck-shaped, wires, ribbons, or the like. In some embodiments, the one or more radiopaque markers are coupled to the positioning elements 900A and 900B via coining/press fitting, welding, adhesives, or the like. In certain embodiments, the one or more radiopaque markers are coupled to the positioning elements 900A and 900B by being covered by the insulator. In some embodiments, the positioning elements 900A and 900B include one or more apertures 906 for receiving the radiopaque markers.

Figure 10A:
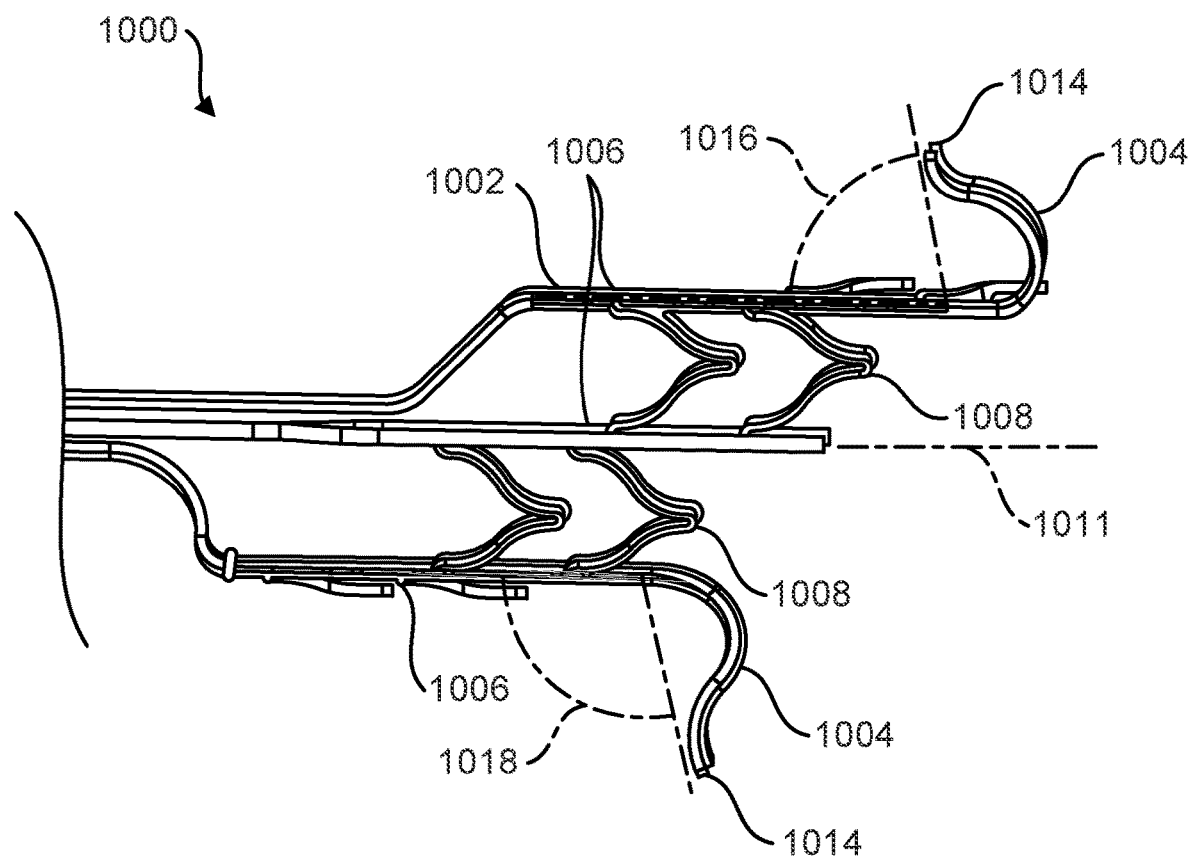
FIGS. 10A-10B are schematic diagrams of side views of another example of an ablation mechanism, in accordance with embodiments of the present disclosure.
Figure 10B:
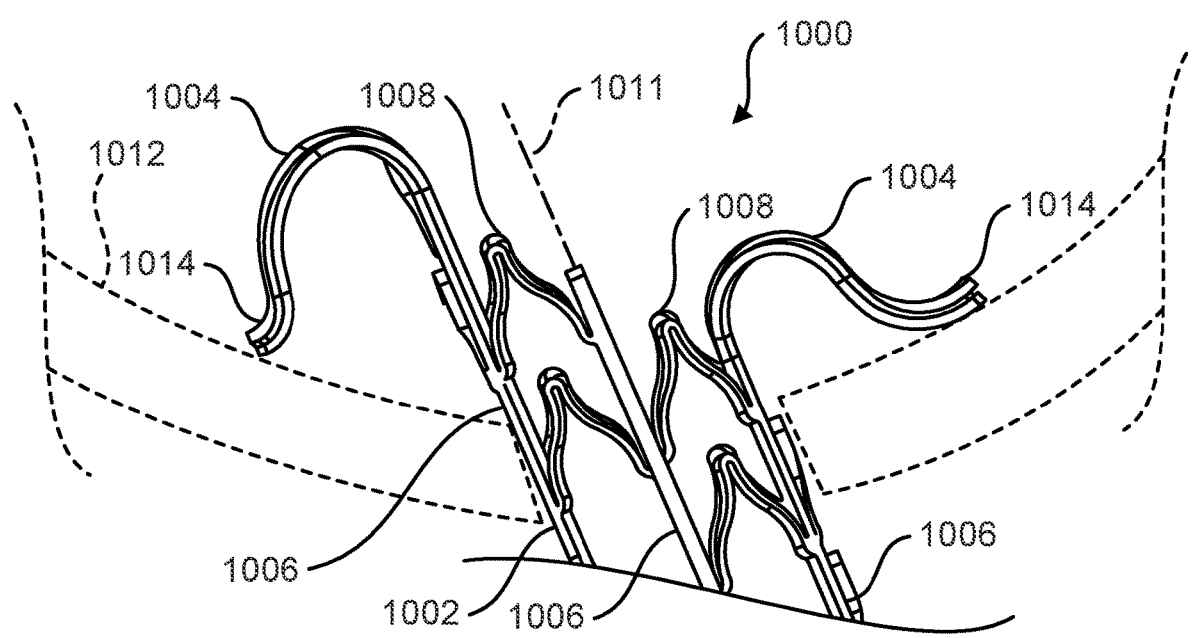

FIGS. 10A and 10B are schematic diagrams of side views of an example of an ablation mechanism 1000 including an expandable cage 1002 and positioning elements 1004, in accordance with embodiments of the present disclosure. In certain embodiments, the ablation mechanism 1000 is constructed of one or more materials that facilitate self-expansion, such as nitinol, or one or more other materials, such as stainless steel, titanium, platinum-iridium, or cobalt-chromium. In certain embodiments, the ablation mechanism 1000 includes a proximal collar (not shown) for coupling to an ablation shaft.

According to certain embodiments, the expandable cage 1002 includes a plurality of expandable struts 1006. In certain embodiments and as illustrated, the expandable cage 1002 includes six expandable struts 1006 (three of the struts 1006 being at least partially obscured in FIGS. 10A-10B). In other embodiments, the expandable cage 1002 includes a different number of expandable struts 1006, such as two, three, four, five, seven, eight, nine, ten, or more expandable struts 1006.

In some embodiments, the expandable struts 1006 are collapsed radially inwardly, or toward each other, when the ablation mechanism 1000 is disposed in a crimping shaft (that is, in a first state; not specifically illustrated). In certain embodiments, the struts 1006 expand radially outwardly, or away from each other, when the ablation mechanism 1000 is disposed outside of the crimping shaft (that is, in a second state, not specifically illustrated). In certain embodiments and as illustrated, the struts 1006 are self-expanding. In certain embodiments, the self-expansion of the struts 1006 may be controlled by a constrainer, such as a plurality of sutures (for example, thin strands) coupled to the struts 1006. Such a constrainer may be reconfigured from a constraining state to a release state to permit the struts 1006 to expand, and the constrainer may be reconfigured from the release state to the constraining state to collapse the struts 1006. In some embodiments, the constrainer may be coupled to distal ends of the struts 1006. In certain embodiments, the struts 1006 are expanded by an actuator, such as an inflatable balloon (not shown). In certain embodiments, an actuator may be disposed in a cavity of the cage 1002 formed between the struts 1006. In certain embodiments, one or more additional components, such as control wires coupled to the actuators, may be disposed in the cavity of the cage 1002.

In certain embodiments and as illustrated, the expandable cage 1002 includes a plurality of connector struts 1008. In some embodiments, each connector strut 1008 is disposed between and couples adjacent expandable struts 1006. In certain embodiments, the connector struts 1008 are integrally formed with the expandable struts 1006.

In some embodiments, the ablation mechanism 1000 further includes the positioning elements 1004, which are coupled to and disposed distally relative to the expandable struts 1006. In certain embodiments, the positioning elements 1004 are disposed outwardly from the expandable cage 1002, or radially outwardly from the expandable struts 1006, relative to a longitudinal axis 1011 defined by the ablation shaft. In some embodiments, the positioning elements 1004 contact tissue 1012 (FIG. 10B) at a target location of a patient and thereby properly position the ablation mechanism 1000 at the target location of the patient. In certain embodiments, one or more of the positioning elements 1004 includes a curved shape. In some embodiments, one or more of the positioning elements 1004 more specifically includes a curved distal end 1014 that defines a soft landing zone configured to atraumatically contact tissue at the target location of the patient.

In certain embodiments, the expandable cage 1002 includes two, three, four, five, six, seven, eight, nine, ten, or more positioning elements 1004. In some embodiments, the ablation mechanism 1000 includes the same number of expandable struts 1006 and positioning elements 1004, more specifically each expandable strut 1006 couples to a single positioning element 1004. In some embodiments, the ablation mechanism 1000 includes fewer positioning elements 1004 than expandable struts 1006, more specifically one or more expandable struts 1006 do not couple to a positioning element 1004.

In certain embodiments, the positioning elements 1004 are constructed of a flexible material. In some embodiments, the positioning elements 1004 are constructed of one or more materials that facilitate self-expansion, such as nitinol, or one or more other materials, such as stainless steel, titanium, platinum-iridium, cobalt-chromium, or flexible plastics. In certain embodiments, one or more of the positioning elements 1004 are each integrally formed with one of the expandable struts 1006 and constructed of the same material(s) as the expandable cage 1002. In some embodiments, one or more of the positioning elements 1004 are constructed of or include a radiopaque material.

In some embodiments, one or more of the expandable struts 1006 contact tissue at a target location within a patient and act as electrodes to deliver ablation energy to the tissue. In certain embodiments, one or more portions of the ablation mechanism 1000 may carry an insulator (not shown; such as a heat shrink tube, a polytetrafluoroethylene (PTFE) coating, an expanded polytetrafluoroethylene (ePTFE) coating, a polyimide coating, or the like) to inhibit delivery of ablation energy to the blood of the patient. In some embodiments, the insulator covers proximal portions of one or more of the expandable struts 1006 and/or the positioning elements 1004. In certain embodiments, the expandable cage 1002 and/or the positioning elements 1004 may include anchor structures that facilitate coupling to the insulator. In alternative embodiments, the expandable cage 1002 carries an electrode structure, such as a thin film electrode, including one or more electrodes (not shown) for delivering ablation energy to the tissue of the patient. In certain embodiments, one or more lead wires (not shown) couple the expandable cage 1002 or the electrode structure to an energy source. In some embodiments, the lead wires may extend through the crimping shaft or outside of the crimping shaft.

In certain embodiments, one or more expandable struts 1006 are offset from one or more other expandable struts 1006 relative to the longitudinal axis 1011, one or more connector struts 1008 are offset from one or more other connector struts 1008 relative to the longitudinal axis 1011, and/or one or more positioning elements 1004 are offset from one or more other positioning elements 1004 relative to the longitudinal axis 1011. In some embodiments, the offset distance is in a range of 0.04 inches to 0.20 inches. In certain embodiments and as illustrated in FIG. 10A, the distal ends 1014 of one or more positioning elements 1004 define a first angle 1016 relative to the longitudinal axis 1011, the distal ends 1014 of one or more other positioning elements 1004 define a second angle 1018 relative to the longitudinal axis 1011, and the first angle 1016 is different than the second angle 1018. In some embodiments, the first angle 1016 is in a range of 45 degrees to 90 degrees. In some embodiments, the second angle 1018 is in a range of 90 degrees to 135 degrees. In certain embodiments and instances, and as shown specifically in FIG. 10B, such longitudinal and/or angular offsets facilitate increased contact and improved seating of the ablation mechanism 1000 against the tissue 1012 of a patient.

Figure 11A:
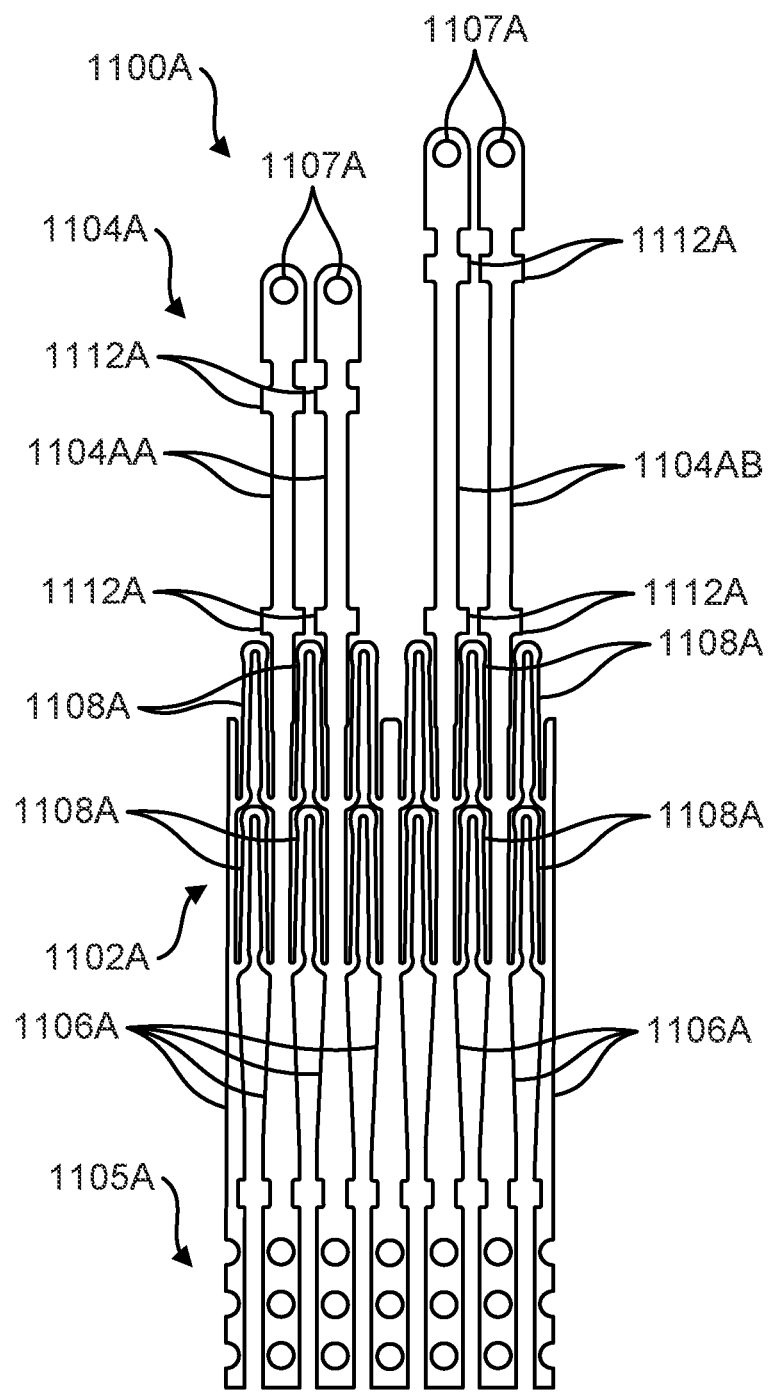
FIGS. 11A-11B are schematic diagrams of side views of examples of ablation mechanism patterns, in accordance with embodiments of the present disclosure.
Figure 11B:
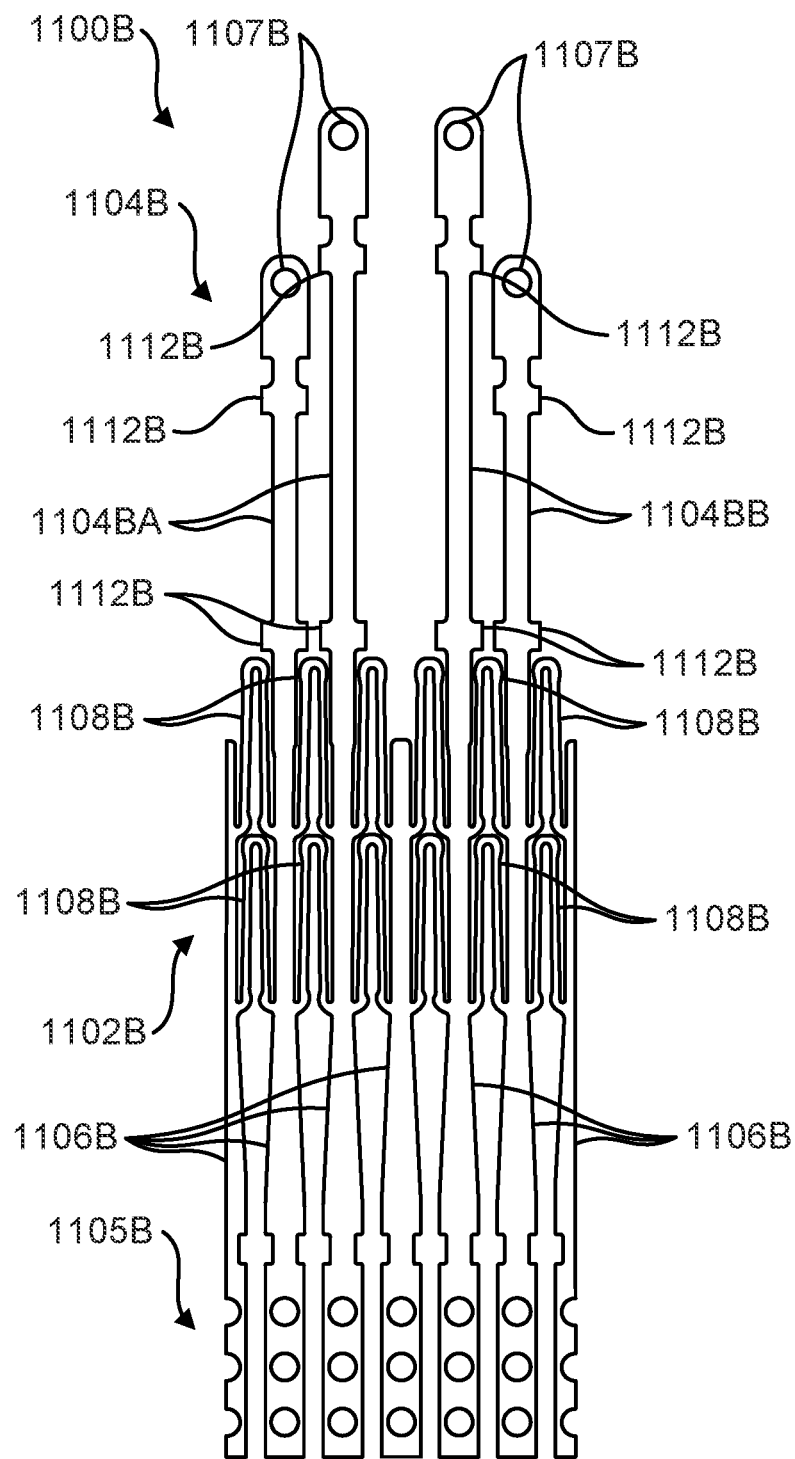

FIGS. 11A and 11B are schematic diagrams of side views of examples of ablation mechanism patterns 1100A and 1100B including expandable cages 1102A and 1102B, respectively, and positioning elements 1104A and 1104B, respectively, in accordance with embodiments of the present disclosure, which may be used to program a laser to cut tubes (not shown), such as metal tubes, into an appropriate shape. In certain embodiments, the tubes are constructed of one or more materials that facilitate self-expansion, such as nitinol, or one or more other materials, such as stainless steel, titanium, platinum-iridium, or cobalt-chromium. In certain embodiments, the ablation mechanism patterns 1100A and 1100B include proximal collars 1105A and 1105B, respectively, for coupling to ablation shafts.

According to certain embodiments, the expandable cages 1102A and 1102B include pluralities of expandable struts 1106A and 1106B, respectively. In certain embodiments and as illustrated, the expandable cages 1102A and 1102B includes six expandable struts 1106A and 1106B, respectively, one of each of the struts 1106A and 1106B being divided into two halves during manufacturing. In other embodiments, the expandable cages 1102A and 1102B include different numbers of expandable struts 1106A and 1106B, respectively, such as two, three, four, five, seven, eight, nine, ten, or more expandable struts 1106A and 1106B.

In some embodiments, the expandable struts 1106A and 1106B are collapsed radially inwardly, or toward each other, when the tubes formed using the ablation mechanisms 1100A and 1100B, respectively, are disposed in crimping shafts (that is, in first states; not specifically illustrated). In certain embodiments, the struts 1106A and 1106B expand radially outwardly, or away from each other, when the ablation mechanisms 1100A and 1100B, respectively, are disposed outside of the crimping shaft (that is, in second states, not specifically illustrated). In certain embodiments and as illustrated, the struts 1106A and 1106B are self-expanding. In certain embodiments, the self-expansion of the struts 1106A and 1106B may be controlled by a constrainer, such as a plurality of sutures (for example, thin strands) coupled to the struts 1106A and 1106B. Such a constrainer may be reconfigured from a constraining state to a release state to permit the struts 1106A and 1106B to expand, and the constrainer may be reconfigured from the release state to the constraining state to collapse the struts 1106A and 1106B. In some embodiments, the constrainer may be coupled to distal ends of the struts. In certain embodiments, the struts 1106A and 1106B are expanded by an actuator, such as an inflatable balloon (not shown). In certain embodiments, actuators may be disposed in cavities of the cages 1102A and 1102B formed between the struts 1106A and 1106B, respectively. In certain embodiments, one or more additional components, such as control wires coupled to the actuators, may be disposed in the cavities of the cages 1102A and 1102B.

In certain embodiments and as illustrated, the expandable cages 1102A and 1102B include a plurality of connector struts 1108A and 1108B, respectively. In some embodiments, each connector strut 1108A and 1108B is disposed between and couples adjacent expandable struts 1106A and 1106B, respectively. In certain embodiments, the connector struts 1108A and 1108B are integrally formed with the expandable struts 1106A and 1106B, respectively.

In some embodiments, the ablation mechanism patterns 1100A and 1100B further include the positioning elements 1104A and 1104B, respectively, which are coupled to and disposed distally relative to the expandable struts 1106A and 1106B, respectively. In certain embodiments, the positioning elements 1104A and 1104B are disposed outwardly from the expandable cages 1102A and 1102B, respectively, or radially outwardly from the expandable struts 1106A and 1106B, respectively, relative to longitudinal axes defined by the ablation shafts, at second states (not specifically illustrated). In some embodiments, the positioning elements 1104A and 1104B contact tissue at a target location of a patient and thereby properly position the tubes formed using the ablation mechanisms 1100A and 1100B, respectively, at the target location of the patient.

In certain embodiments, the expandable cages 1102A and 1102B includes two, three, four, five, six, seven, eight, nine, ten, or more positioning elements 1104A and 1104B, respectively. In some embodiments, the ablation mechanism patterns 1100A and 1100B include the same number of expandable struts 1106A and 1106B, respectively, and positioning elements 1104A and 1104B, respectively, more specifically each expandable strut 1106A and 1106B couples to a single positioning element 1104A and 1104B, respectively. In some embodiments, the ablation mechanism patterns 1100A and 1100B include fewer positioning elements 1104A and 1104B, respectively, than expandable struts 1106A and 1106B, respectively, more specifically one or more expandable struts 1106A and 1106B do not couple to positioning elements 1104A and 1104B, respectively.

In some embodiments, one or more of the positioning elements 1104A and 1104B are constructed of or include a radiopaque material. In certain embodiments, the positioning elements 1104A and 1104B carry one or more radiopaque markers (not shown) to facilitate visualization of the positioning elements 1104A and 1104B under fluoroscopy. In some embodiments, the one or more radiopaque markers are constructed of platinum, platinum-iridium, gold, tantalum, palladium, or the like. In certain embodiments, the one or more radiopaque markers can ball-shaped, puck-shaped, wires, ribbons, or the like. In some embodiments, the one or more radiopaque markers are coupled to the positioning elements 1104A and 1104B via coining/press fitting, welding, adhesives, or the like. In certain embodiments, the one or more radiopaque markers are coupled to the positioning elements 1104A and 1104B by being covered by the insulator. In some embodiments, the positioning elements 1104A and 1104B include one or more apertures 1107A and 1107B, respectively, for receiving the radiopaque markers.

In certain embodiments, one or more of the positioning elements 1104A and 1104B have different lengths than one or more other positioning elements 1104A and 1104B (in both the flat initial configurations and subsequent curved configurations) to facilitate increased contact and improved seating of the tubes formed using the ablation mechanism patterns 1100A and 1100B against the tissue of a patient. For example and referring specifically to FIG. 11A, in some embodiments the ablation mechanism pattern 1100A includes a first group of adjacent positioning elements 1104AA having a first length and a second group of adjacent positioning elements 1104AB having a second length, and the second length is greater than the first length. As another example and referring specifically to FIG. 11B, in some embodiments the ablation mechanism pattern 1100B includes a first group of adjacent positioning elements 1104BA with different lengths and a second group of adjacent positioning elements 1104BB with different lengths. In certain embodiments, in each group of positioning elements 1104BA and 1104BB one or more positioning elements has a first length, one or more positioning elements has a second length, and the second length is greater than the first length.

In some embodiments, one or more of the expandable struts 1106A and 1106B contact tissue at a target location within a patient and act as electrodes to deliver ablation energy to the tissue. In certain embodiments, one or more portions of the tubes formed using the ablation mechanism patterns 1100A and 1100B may carry insulators (not shown; such as a heat shrink tube, a polytetrafluoroethylene (PTFE) coating, an expanded polytetrafluoroethylene (ePTFE) coating, a polyimide coating, or the like) to inhibit delivery of ablation energy to the blood of the patient. In some embodiments, the insulators cover proximal portions of one or more of the expandable struts 1106A and 1106B and/or the positioning elements 1104A and 1104B. In certain embodiments, the expandable cages 1102A and 1102B and/or the positioning elements 1104A and 1104B may include anchor structures that facilitate coupling to the insulator. In certain embodiments and as illustrated, one or more of the positioning elements 1104A and 1104B include protrusions 1112A and 1112B, respectively, to facilitate coupling to the insulators. In some embodiments, additional or alternative features couple the insulators to the tubes formed using the ablation mechanism patterns 1100A and 1100B, such as sutures and/or adhesives. In certain embodiments, the insulators may have thicknesses in a range of 0.0005 inches to 0.008 inches, more specifically about 0.004 inches. In alternative embodiments, the expandable cages 1102A and 1102B carry electrode structures, such as thin film electrodes, including one or more electrodes (not shown) for delivering ablation energy to the tissue of the patient. In certain embodiments, one or more lead wires (not shown) couple the expandable cages 1102A and 1102B or the electrode structure to an energy source. In some embodiments, the lead wires may extend through the crimping shaft or outside of the crimping shaft.

Figure 12A:
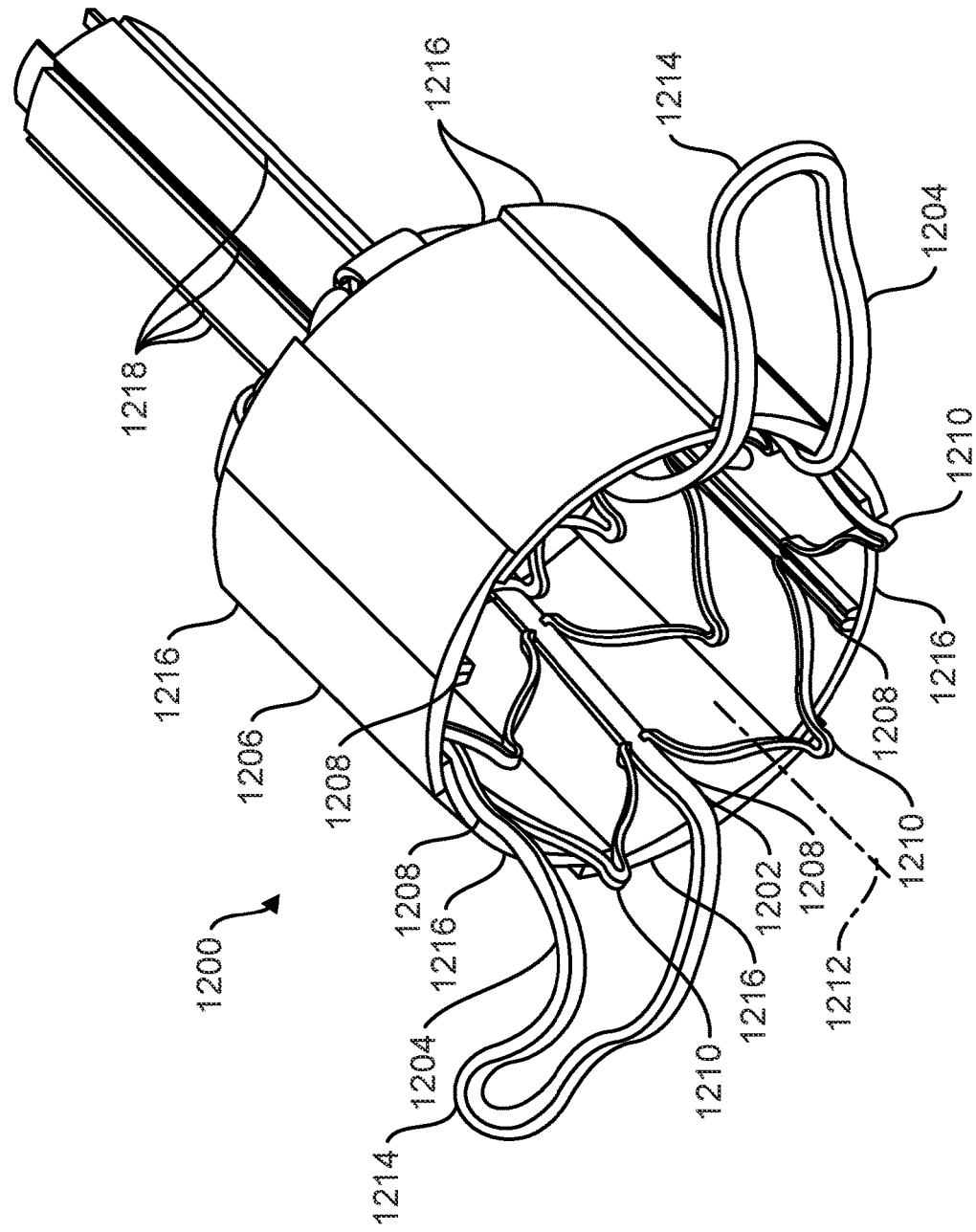
FIGS. 12A-12B are schematic diagrams of views of an example of an ablation mechanism, in accordance with embodiments of the present disclosure.
Figure 12B:
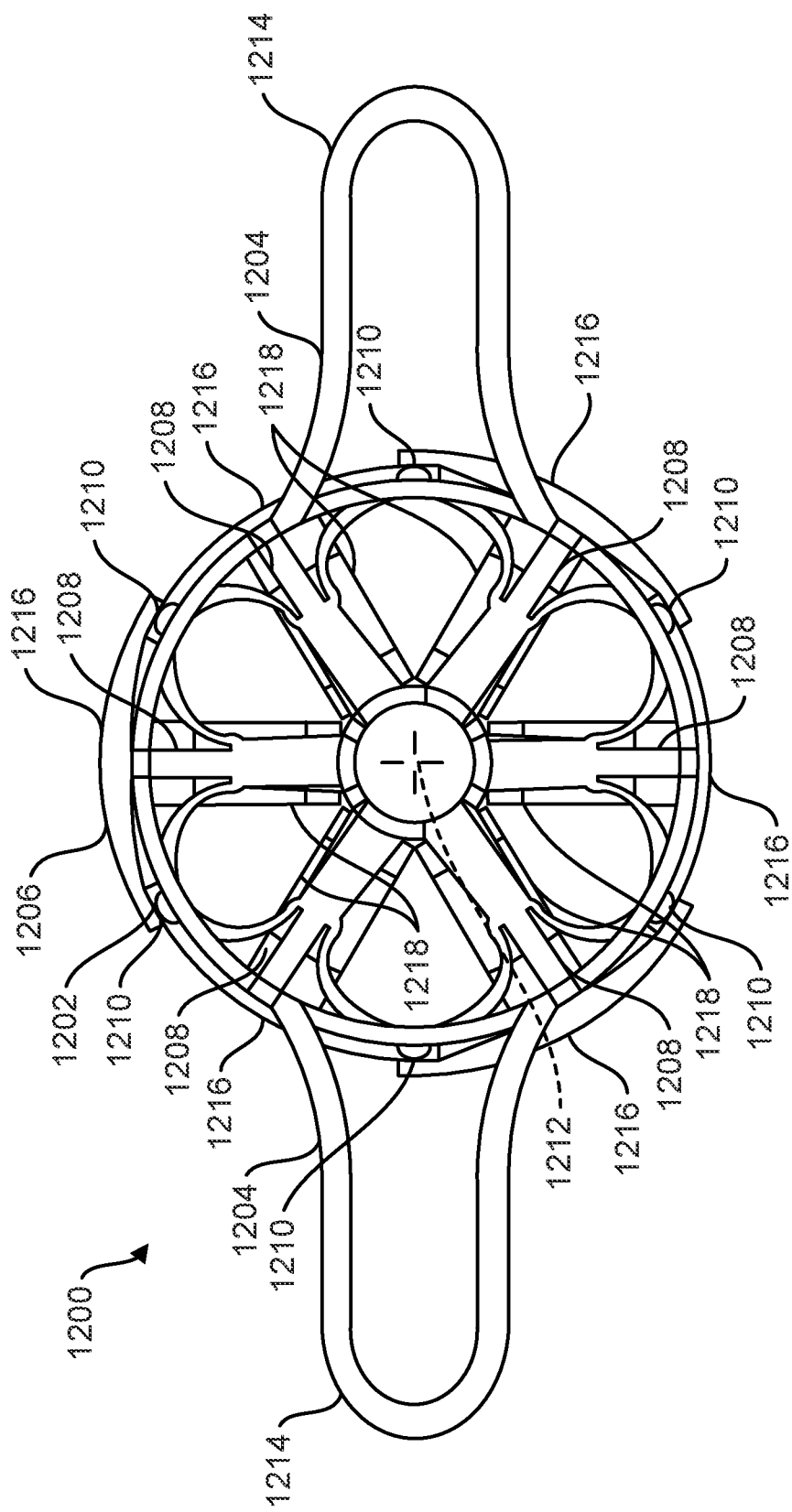

FIGS. 12A and 12B are schematic diagrams of side views of an example of an ablation mechanism 1200 including an expandable cage 1202, positioning elements 1204, and an expandable iris assembly 1206, in accordance with embodiments of the present disclosure. In certain embodiments, the expandable cage 1202 and the positioning elements 1204 are constructed of one or more materials that facilitate self-expansion, such as nitinol, or one or more other materials, such as stainless steel, titanium, platinum-iridium, or cobalt-chromium. In certain embodiments, the ablation mechanism 1200 includes a proximal collar (not shown) for coupling to an ablation shaft.

According to certain embodiments, the expandable cage 1202 includes a plurality of expandable struts 1208. In certain embodiments and as illustrated, the expandable cage 1202 includes six expandable struts 1208. In other embodiments, the expandable cage 1202 includes a different number of expandable struts 1208, such as two, three, four, five, seven, eight, nine, ten, or more expandable struts 1208.

In some embodiments, the expandable struts 1208 are collapsed radially inwardly, or toward each other, when the ablation mechanism 1200 is disposed in a crimping shaft (that is, in a first state; not specifically illustrated). In certain embodiments, the struts 1208 expand radially outwardly, or away from each other, when the ablation mechanism 1200 is disposed outside of the crimping shaft (that is, in a second state and as illustrated). In certain embodiments and as illustrated, the struts 1208 are self-expanding. In certain embodiments, the self-expansion of the struts 1208 may be controlled by a constrainer, such as a plurality of sutures (for example, thin strands) coupled to the struts 1208. Such a constrainer may be reconfigured from a constraining state to a release state to permit the struts 1208 to expand, and the constrainer may be reconfigured from the release state to the constraining state to collapse the struts 1208. In some embodiments, the constrainer may be coupled to distal ends of the struts 1208. In certain embodiments, the struts 1208 are expanded by an actuator, such as an inflatable balloon (not shown). In certain embodiments, an actuator may be disposed in a cavity of the cage 1202 formed between the struts 1208. In certain embodiments, one or more additional components, such as control wires coupled to the actuators, may be disposed in the cavity of the cage 1202.

In certain embodiments and as illustrated, the expandable cage 1202 includes a plurality of connector struts 1210. In some embodiments, each connector strut 1208 is disposed between and couples adjacent expandable struts 1208. In certain embodiments, the connector struts 1210 are integrally formed with the expandable struts 1208.

In some embodiments, the ablation mechanism 1200 further includes the positioning elements 1204, which are coupled to and disposed distally relative to the expandable struts 1208. In certain embodiments, the positioning elements 1204 are disposed outwardly from the expandable cage 1202, or radially outwardly from the expandable struts 1208, relative to a longitudinal axis 1212 defined by the ablation shaft. In some embodiments, the positioning elements 1204 contact tissue at a target location of a patient and thereby properly position the ablation mechanism 1200 at the target location of the patient.

In certain embodiments, the ablation mechanism 1200 includes two, three, four, five, six, seven, eight, nine, ten, or more positioning elements 1204. In some embodiments and as illustrated, the ablation mechanism 1200 includes one or more positioning elements 1204 that each couple to two expandable struts 1208 and form a portion of a loop therebetween. In certain embodiments, one or more of the positioning elements 1204 includes a curved shape. In some embodiments, one or more of the positioning elements 1204 more specifically includes a curved distal end 1214 that defines a soft landing zone configured to atraumatically contact tissue at the target location of the patient. In some embodiments, the ablation mechanism 1200 includes a different number and/or arrangement of positioning elements 1204.

In certain embodiments, the expandable iris assembly 1206 is disposed radially outwardly from the plurality of expandable struts 1208 relative to the longitudinal axis 1212. In some embodiments, the iris assembly 1206 includes a plurality of relatively movable iris elements 1216 disposed radially outwardly from the expandable struts 1208 and the connector struts 1210. In certain embodiments, the iris elements 1216 are collapsed radially inwardly, or toward each other, when the ablation mechanism 1200 is disposed in the crimping shaft (that is, in the first state; not specifically illustrated). In some embodiments, the iris elements 1216 move relative to each other, more specifically slide past each other, and extend radially outwardly when the ablation mechanism 1200 is disposed outside of the crimping shaft (that is, when moving the second state, as illustrated).

In certain embodiments and as illustrated, the expandable iris assembly 1206 includes six iris elements 1216. In some embodiments, the expandable iris assembly 1206 includes a different number of iris elements 1216, such as two, three, four, five, seven, eight, nine, ten, or more iris elements 1216. In certain embodiments, the iris elements 1216 are constructed of one or more of various materials, such as nitinol, stainless steel, titanium, platinum-iridium, cobalt-chromium, plastics, or the like.

In some embodiments, the iris assembly 1206 carries an electrode structure (not shown), such as a thin film electrode, including one or more electrodes, for delivering ablation energy to the tissue of the patient. In some embodiments, one or more of the iris elements 1216 carries an electrode structure on its outer surface. In certain embodiments, one or more conductors 1218 couple the electrode structure(s) to an energy source. In some embodiments, the conductors 1218 may extend through the crimping shaft or outside of the crimping shaft. In certain embodiments, the iris assembly 1206 and the electrode structure advantageously define a relatively large shunting area.

Figure 13A:
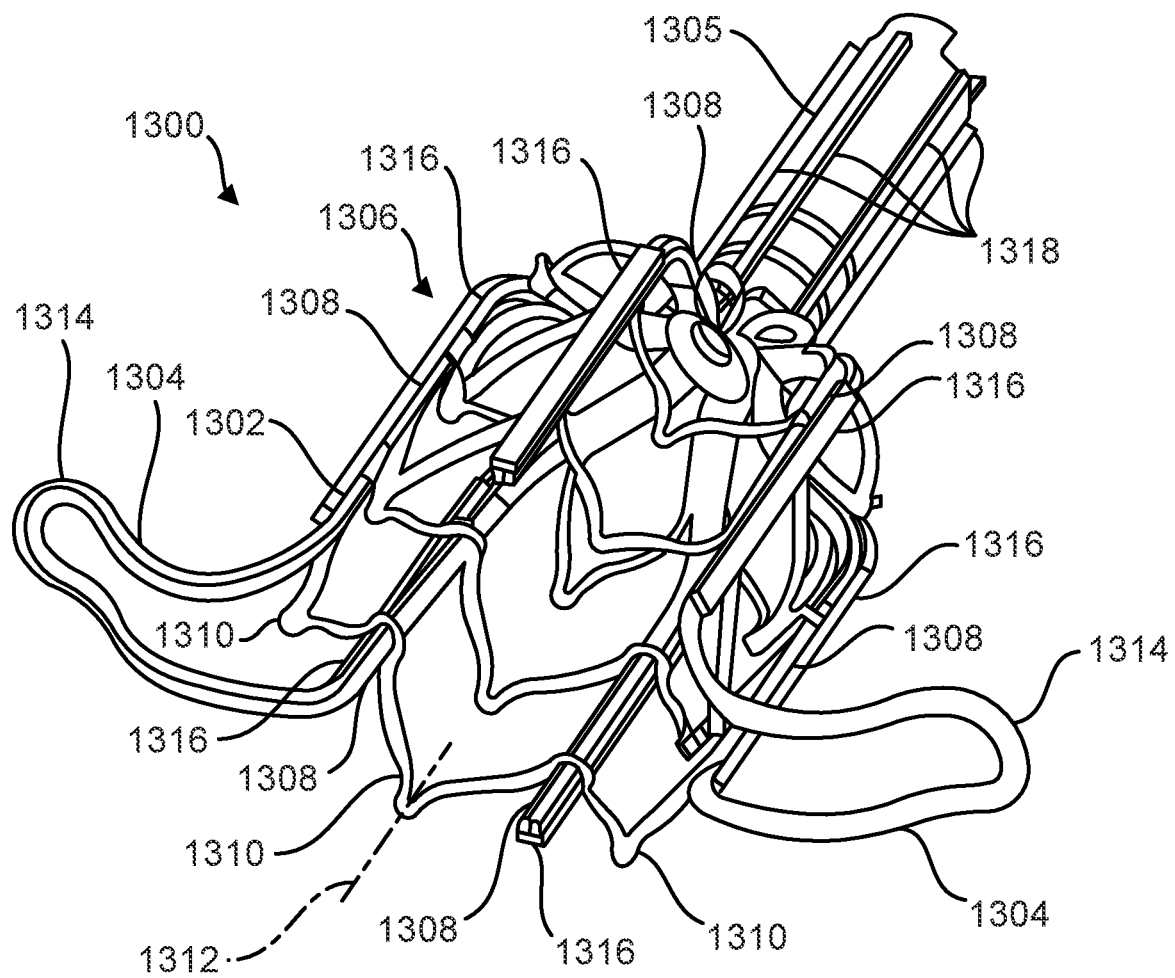
FIGS. 13A-13B are schematic diagrams of views of an example of an ablation mechanism, in accordance with embodiments of the present disclosure.
Figure 13B:
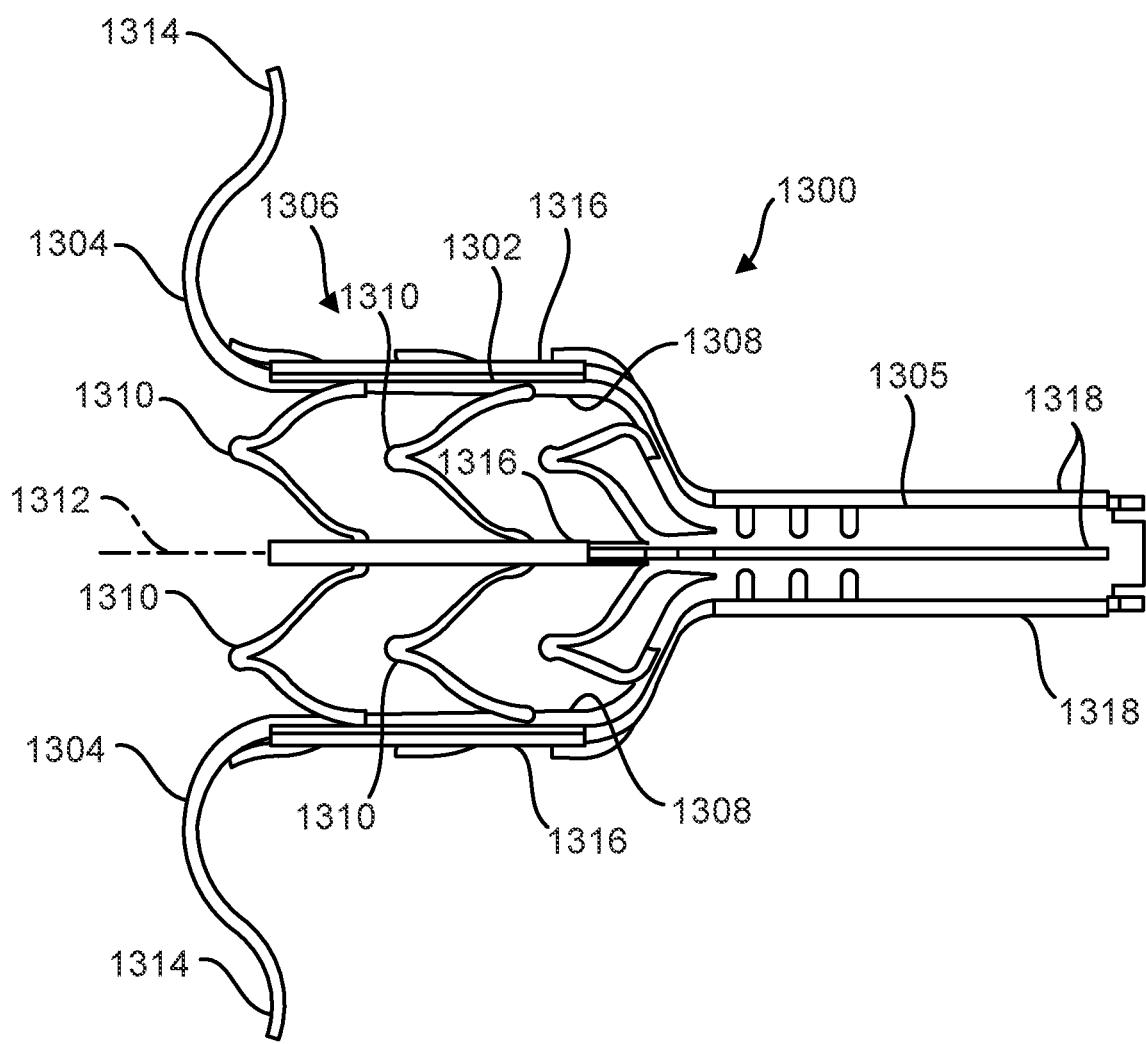

FIGS. 13A and 13B are schematic diagrams of side views of an example of an ablation mechanism 1300 including an expandable cage 1302, positioning elements 1304, and an electrode array 1306 for delivering ablation energy to tissue of a patient, in accordance with embodiments of the present disclosure. In certain embodiments, the expandable cage 1302 and the positioning elements 1304 are constructed of one or more materials that facilitate self-expansion, such as nitinol, or one or more other materials, such as stainless steel, titanium, platinum-iridium, or cobalt-chromium. In certain embodiments, the ablation mechanism 1300 includes a proximal collar 1305 for coupling to an ablation shaft.

According to certain embodiments, the expandable cage 1302 includes a plurality of expandable struts 1308. In certain embodiments and as illustrated, the expandable cage 1302 includes six expandable struts 1308. In other embodiments, the expandable cage 1302 includes a different number of expandable struts 1308, such as two, three, four, five, seven, eight, nine, ten, or more expandable struts 1308.

In some embodiments, the expandable struts 1308 are collapsed radially inwardly, or toward each other, when the ablation mechanism 1300 is disposed in a crimping shaft (that is, in a first state; not specifically illustrated). In certain embodiments, the struts 1308 expand radially outwardly, or away from each other, when the ablation mechanism 1300 is disposed outside of the crimping shaft (that is, in a second state and as illustrated). In certain embodiments and as illustrated, the struts 1308 are self-expanding. In certain embodiments, the self-expansion of the struts 1308 may be controlled by a constrainer, such as a plurality of sutures (for example, thin strands) coupled to the struts 1308. Such a constrainer may be reconfigured from a constraining state to a release state to permit the struts 1308 to expand, and the constrainer may be reconfigured from the release state to the constraining state to collapse the struts 1308. In some embodiments, the constrainer may be coupled to distal ends of the struts 1308. In certain embodiments, the struts 1308 are expanded by an actuator, such as an inflatable balloon (not shown). In certain embodiments, an actuator may be disposed in a cavity of the cage 1302 formed between the struts 1308. In certain embodiments, one or more additional components, such as control wires coupled to the actuators, may be disposed in the cavity of the cage 1302.

In certain embodiments and as illustrated, the expandable cage 1302 includes a plurality of connector struts 1310. In some embodiments, each connector strut 1308 is disposed between and couples adjacent expandable struts 1308. In certain embodiments, the connector struts 1310 are integrally formed with the expandable struts 1308.

In some embodiments, the ablation mechanism 1300 further includes the positioning elements 1304, which are coupled to and disposed distally relative to the expandable struts 1308. In certain embodiments, the positioning elements 1304 are disposed outwardly from the expandable cage 1302, or radially outwardly from the expandable struts 1308, relative to a longitudinal axis 1312 defined by the ablation shaft. In some embodiments, the positioning elements 1304 contact tissue at a target location of a patient and thereby properly position the ablation mechanism 1300 at the target location of the patient.

In certain embodiments, the ablation mechanism 1300 includes two, three, four, five, six, seven, eight, nine, ten, or more positioning elements 1304. In some embodiments and as illustrated, the ablation mechanism 1300 includes one or more positioning elements 1304 that each couple to two expandable struts 1308 and form a portion of a loop therebetween. In certain embodiments, one or more of the positioning elements 1304 includes a curved shape. In some embodiments, one or more of the positioning elements 1304 more specifically includes a curved distal end 1314 that defines a soft landing zone configured to atraumatically contact tissue at the target location of the patient. In some embodiments, the ablation mechanism 1300 includes a different number and/or arrangement of positioning elements 1304.

In certain embodiments, the electrode array 1306 is disposed radially outwardly from the plurality of expandable struts 1308 relative to the longitudinal axis 1312. In some embodiments, the electrode array 1306 includes a plurality of electrodes 1316 disposed radially outwardly from the expandable struts 1308. In some embodiments, the electrodes 1316 are electrode ribbons. In certain embodiments, the electrodes 1316 move together with the expandable struts 1308. In some embodiments, the electrodes 1316 may be coupled to the expandable struts 1308 in various manners, such as via lamination, epoxies, adhesives, or the like. In some embodiments, the electrodes 1316 are collapsed radially inwardly, or toward each other, when the ablation mechanism 1300 is disposed in the crimping shaft (that is, in the first state; not specifically illustrated). In some embodiments, the electrodes 1316 extend radially outwardly when the ablation mechanism 1300 is disposed outside of the crimping shaft (that is, in the second state, as illustrated).

In certain embodiments and as illustrated, the electrode array 1306 includes six electrodes 1316. In some embodiments, the electrode array 1306 includes a different number of electrodes 1316, such as two, three, four, five, seven, eight, nine, ten, or more electrodes 1316. In certain embodiments and as illustrated, each expandable strut 1308 couples to a single electrode 1316. In some embodiments, one or more of the expandable struts 1308 do not couple to an electrode 1316. In certain embodiments, one or more conductors 1318 couple the electrodes 1316 to an energy source. In some embodiments, the conductors 1318 may extend through the crimping shaft or outside of the crimping shaft. In certain embodiments, the electrode array 1306 advantageously provides relatively high energy efficiency and relatively low power consumption.

Figure 14A:
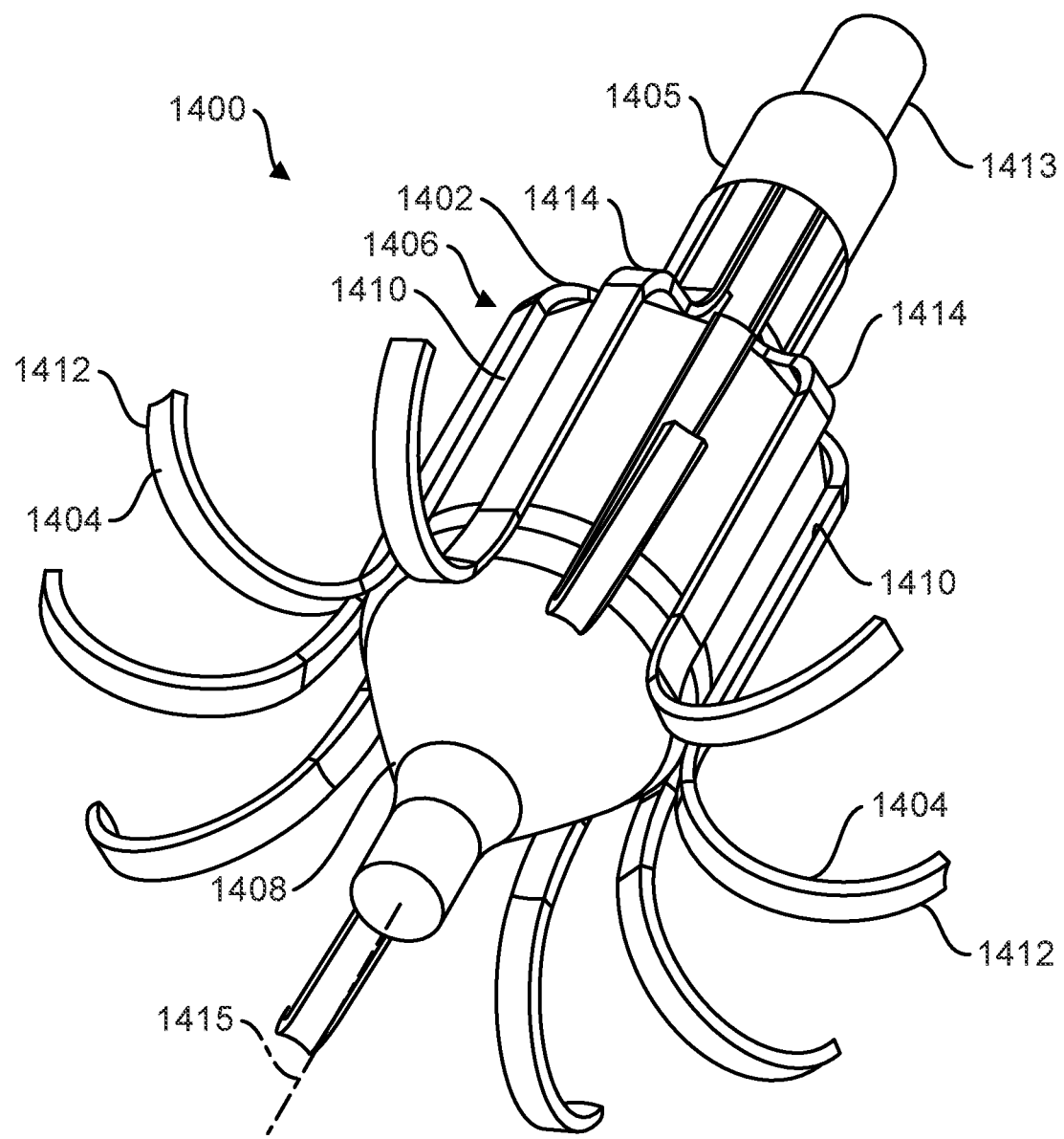
FIGS. 14A-14B are schematic diagrams of views of an example of an ablation mechanism and an actuator for expanding the ablation mechanism, in accordance with embodiments of the present disclosure.
Figure 14B:
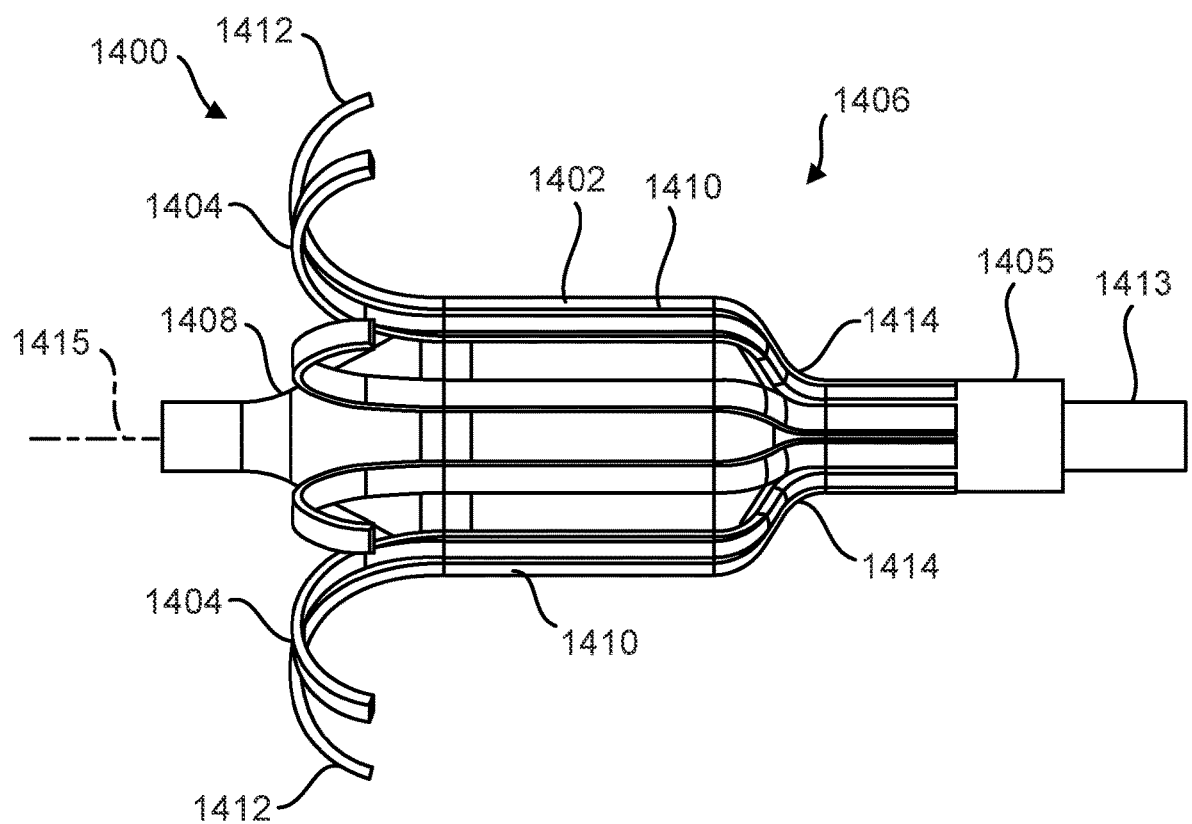

FIGS. 14A and 14B are schematic diagrams of side views of an example of an ablation mechanism 1400 including an expandable cage 1402, positioning elements 1404, and an electrode array 1406, and an actuator 1408 for expanding the ablation mechanism 1400, in accordance with embodiments of the present disclosure. In certain embodiments, the expandable cage 1402 is constructed of one or more of various materials, such as nitinol, stainless steel, titanium, platinum-iridium, or cobalt-chromium. In certain embodiments, the ablation mechanism 1400 includes a proximal collar 1405 for coupling to an ablation shaft.

According to certain embodiments, the expandable cage 1402 includes a plurality of expandable struts 1410. In certain embodiments and as illustrated, the expandable cage 1402 includes ten expandable struts 1410. In other embodiments, the expandable cage 1402 includes a different number of expandable struts 1410, such as two, three, four, five, six, seven, eight, nine, eleven, or more expandable struts 1410.

In some embodiments, the expandable struts 1410 are collapsed radially inwardly, or toward each other, when the ablation mechanism 1400 is disposed in a crimping shaft (that is, in a first state; not specifically illustrated). In certain embodiments, the struts 1410 expand radially outwardly, or away from each other, when the ablation mechanism 1400 is disposed outside of the crimping shaft (that is, in a second state and as illustrated). In certain embodiments, the struts 1410 are expanded by the actuator 1408, which may be an inflatable balloon. In certain embodiments, the actuator 1408 is disposed in a cavity of the cage 1402 formed between the struts 1410. In certain embodiments, one or more additional components of the actuator 1408, such as an inflation fluid delivery conduit 1413, may be disposed in the proximal collar 1405.

In some embodiments, the ablation mechanism 1400 further includes the positioning elements 1404, which are coupled to and disposed distally relative to the expandable struts 1410. In certain embodiments, the positioning elements 1404 are disposed outwardly from the expandable cage 1402, or radially outwardly from the expandable struts 1410, relative to a longitudinal axis 1415 defined by the ablation shaft. In some embodiments, the positioning elements 1404 contact tissue at a target location of a patient and thereby properly position the ablation mechanism 1400 at the target location of the patient.

In certain embodiments, the ablation mechanism 1400 includes two, three, four, five, six, seven, eight, nine, ten, or more positioning elements 1404. In some embodiments and as illustrated, each expandable strut 1410 couples to a single positioning elements 1404. In certain embodiments, one or more of the positioning elements 1404 includes a curved shape. In some embodiments, one or more of the positioning elements 1404 more specifically includes a curved distal end 1412 that defines a soft landing zone configured to atraumatically contact tissue at the target location of the patient. In some embodiments, the ablation mechanism 1400 includes a different number and/or arrangement of positioning elements 1404.

In certain embodiments, the positioning elements 1404 are constructed of a flexible material. In some embodiments, the positioning elements 1404 are constructed of a different material than the expandable cage 1402. In some embodiments, the positioning elements 1404 are constructed of one or more materials that facilitate self-expansion, such as nitinol, or one or more other materials, such as stainless steel, titanium, platinum-iridium, cobalt-chromium, or flexible plastics. In certain embodiments, one or more of the positioning elements 1404 are integrally formed with the expandable struts 1410 and constructed of the same material(s) as the expandable cage 1402. In some embodiments, one or more of the positioning elements 1404 are constructed of or include a radiopaque material.

In certain embodiments, the electrode array 1406 is disposed radially outwardly from the plurality of expandable struts 1410 relative to the longitudinal axis 1415. In some embodiments, the electrode array 1406 includes a plurality of electrodes 1414 disposed radially outwardly from the expandable struts 1410. In some embodiments, the electrodes 1414 are flexible electrode ribbons. In certain embodiments, the electrodes 1414 move together with the expandable struts 1410. In some embodiments, the electrodes 1414 may be coupled to the expandable struts 1410 in various manners, such as via lamination, epoxies, adhesives, or the like. In some embodiments, the electrodes 1414 are collapsed radially inwardly, or toward each other, when the ablation mechanism 1400 is disposed in the crimping shaft (that is, in the first state; not specifically illustrated). In some embodiments, the electrodes 1414 extend radially outwardly when the ablation mechanism 1400 is disposed outside of the crimping shaft (that is, in the second state, as illustrated).

In certain embodiments and as illustrated, the electrode array 1406 includes ten electrodes 1414. In some embodiments, the electrode array 1406 includes a different number of electrodes 1414, such as two, three, four, five, six, seven, eight, nine, eleven, or more electrodes 1414. In certain embodiments and as illustrated, each expandable strut 1410 couples to a single electrode 1414. In some embodiments, one or more of the expandable struts 1410 do not couple to an electrode 1414. In certain embodiments, one or more conductors (not shown) couple the electrodes 1414 to an energy source. In some embodiments, the conductors may extend through the crimping shaft or outside of the crimping shaft. In certain embodiments, the actuator 1408 provides relatively high radial support for the electrode array 1406.

Figure 15A:
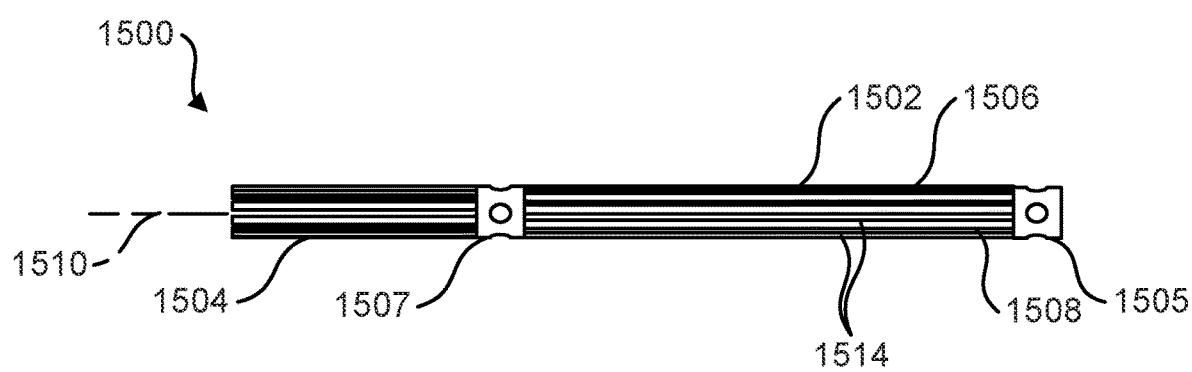
FIGS. 15A-15C are schematic diagrams of side views of an example of an ablation mechanism, according to certain embodiments of the present disclosure.
Figure 15B:
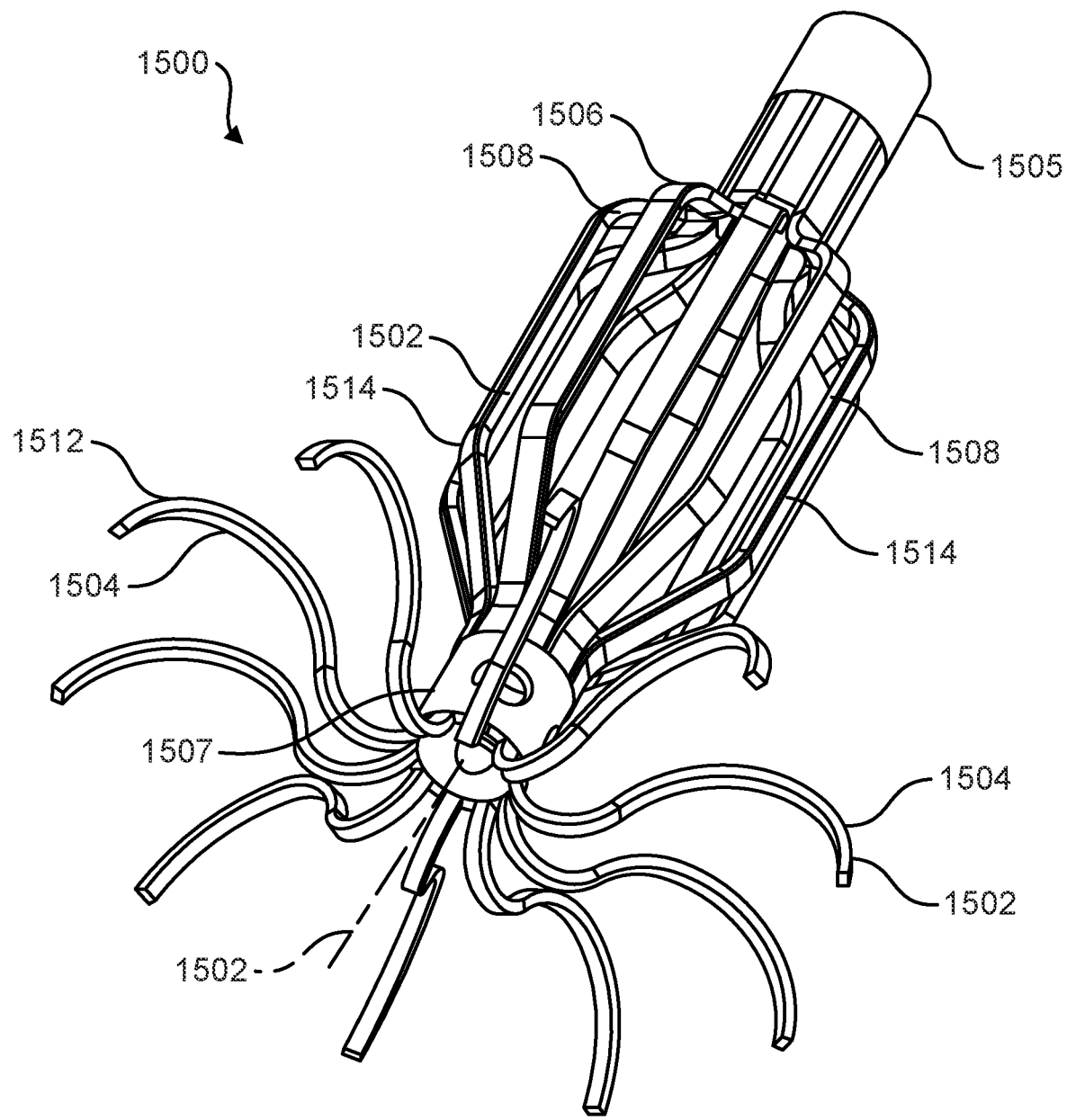

FIGS. 15A and 15B are schematic diagrams of side views of an example of an ablation mechanism 1500 including an expandable cage 1502, positioning elements 1504, and an electrode array 1506, in accordance with embodiments of the present disclosure. In certain embodiments, the ablation mechanism 1500 includes a proximal collar 1505 for coupling to an ablation shaft. In certain embodiments, the ablation mechanism 1500 includes a distal collar 1507 for coupling the expandable cage 1502 and the positioning elements 1504. In some embodiments, the expandable cage 1502, the positioning elements 1504, the proximal collar 1505, and the distal collar 1507 are integrally constructed from a laser-cut hypotube. In certain embodiments, the expandable cage 1502, the positioning elements 1504, the proximal collar 1505, and the distal collar 1507 are constructed of one or more materials that facilitate self-expansion, such as nitinol, or one or more other materials, such as stainless steel, titanium, platinum-iridium, or cobalt-chromium.

According to certain embodiments, the expandable cage 1502 includes a plurality of expandable struts 1508. In certain embodiments and as illustrated, the expandable cage 1502 includes ten expandable struts 1508. In other embodiments, the expandable cage 1502 includes a different number of expandable struts 1508, such as two, three, four, five, six, seven, eight, nine, eleven, or more expandable struts 1508.

Figure 15C:
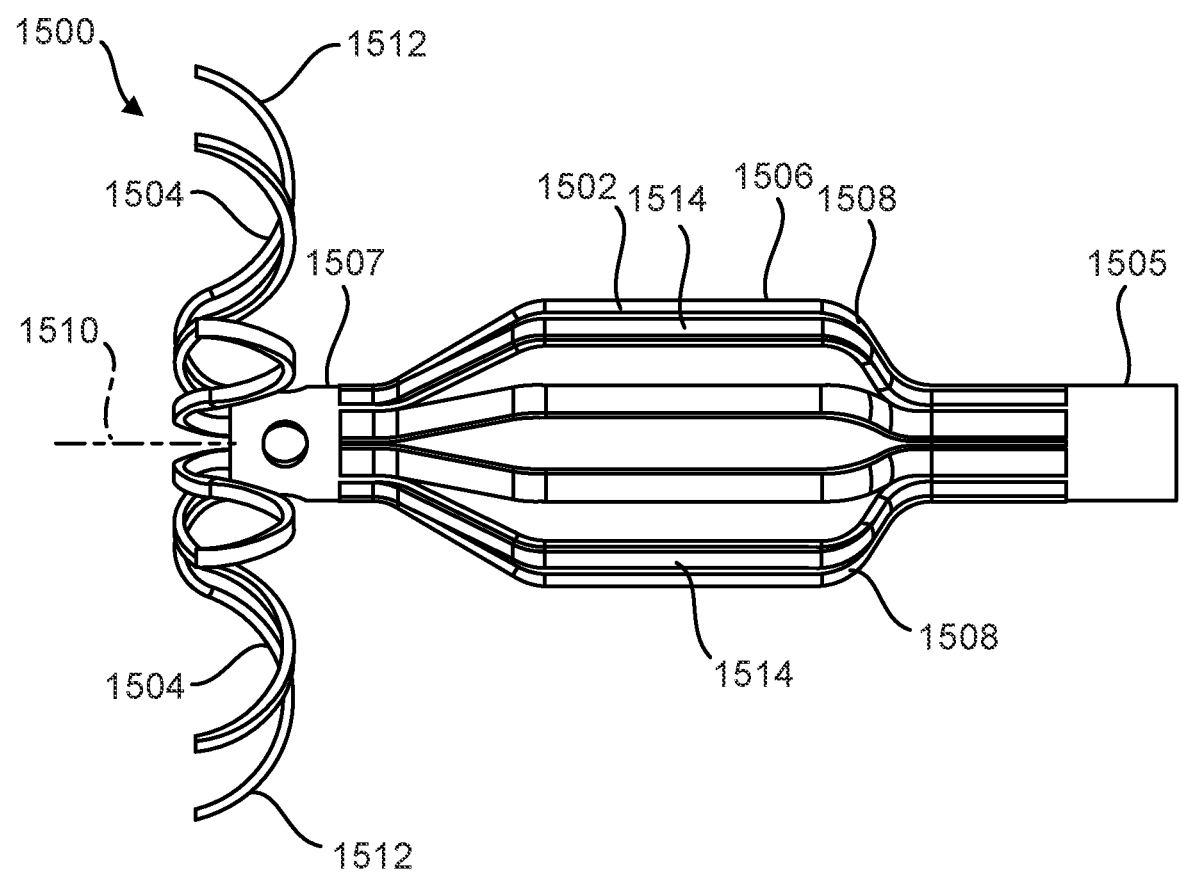

In some embodiments, the expandable struts 1508 are collapsed radially inwardly, or toward each other, when the ablation mechanism 1500 is disposed in a crimping shaft (that is, in a first state and as illustrated in FIG. 15A). In certain embodiments, the struts 1508 expand radially outwardly, or away from each other, when the ablation mechanism 1500 is disposed outside of the crimping shaft (that is, in a second state and as illustrated in FIGS. 15B and 15C).

In certain embodiments and as illustrated, the struts 1508 are self-expanding. In certain embodiments, the self-expansion of the struts 1508 may be controlled by a constrainer, such as a plurality of sutures (for example, thin strands) coupled to the struts 1508. Such a constrainer may be reconfigured from a constraining state to a release state to permit the struts 1508 to expand, and the constrainer may be reconfigured from the release state to the constraining state to collapse the struts 1508. In certain embodiments, the struts 1508 are expanded by an actuator, such as an inflatable balloon (not shown). In certain embodiments, an actuator may be disposed in a cavity of the cage 1502 formed between the struts 1508. In certain embodiments, one or more additional components, such as control wires coupled to the actuators, may be disposed in the cavity of the cage 1502.

In some embodiments, the ablation mechanism 1500 further includes the positioning elements 1504, which are coupled to and disposed distally relative to the distal collar 1507. In certain embodiments, the positioning elements 1504 are disposed outwardly from the expandable cage 1502, or radially outwardly from the expandable struts 1508, relative to a longitudinal axis 1510 defined by the ablation shaft. In some embodiments, the positioning elements 1504 contact tissue at a target location of a patient and thereby properly position the ablation mechanism 1500 at the target location of the patient.

In certain embodiments, the ablation mechanism 1500 includes ten positioning elements 1504. In other embodiments, the positioning elements 1504 includes a different number of positioning elements 1504, such as two, three, four, five, six, seven, eight, nine, eleven, or more positioning elements 1504. In certain embodiments, one or more of the positioning elements 1504 includes a curved shape. In some embodiments, one or more of the positioning elements 1504 more specifically includes a curved distal end 1512 that defines a soft landing zone configured to atraumatically contact tissue at the target location of the patient. In some embodiments, the ablation mechanism 1500 includes a different number and/or arrangement of positioning elements 1504.

In certain embodiments, the electrode array 1506 is disposed radially outwardly from the plurality of expandable struts 1508 relative to the longitudinal axis 1510. In some embodiments, the electrode array 1506 includes a plurality of electrodes 1514 disposed radially outwardly from the expandable struts 1508. In some embodiments, the electrodes 1514 are flexible electrode ribbons. In certain embodiments, the electrodes 1514 move together with the expandable struts 1508. In some embodiments, the electrodes 1514 may be coupled to the expandable struts 1508 in various manners, such as via lamination, epoxies, adhesives, or the like. In some embodiments, the electrodes 1514 are collapsed radially inwardly, or toward each other, when the ablation mechanism 1500 is disposed in the crimping shaft (that is, in the first state and as shown in FIG. 15A). In some embodiments, the electrodes 1514 extend radially outwardly when the ablation mechanism 1500 is disposed outside of the crimping shaft (that is, in the second state and as illustrated in FIGS. 15B and 15C).

In certain embodiments and as illustrated, the electrode array 1506 includes ten electrodes 1514. In some embodiments, the electrode array 1506 includes a different number of electrodes 1514, such as two, three, four, five, six, seven, eight, nine, eleven, or more electrodes 1514. In certain embodiments and as illustrated, each expandable strut 1508 couples to a single electrode 1514. In some embodiments, one or more of the expandable struts 1508 do not couple to an electrode 1514. In certain embodiments, one or more conductors (not shown) couple the electrodes 1514 to an energy source. In some embodiments, the conductors may extend through the crimping shaft or outside of the crimping shaft.

Figure 16:
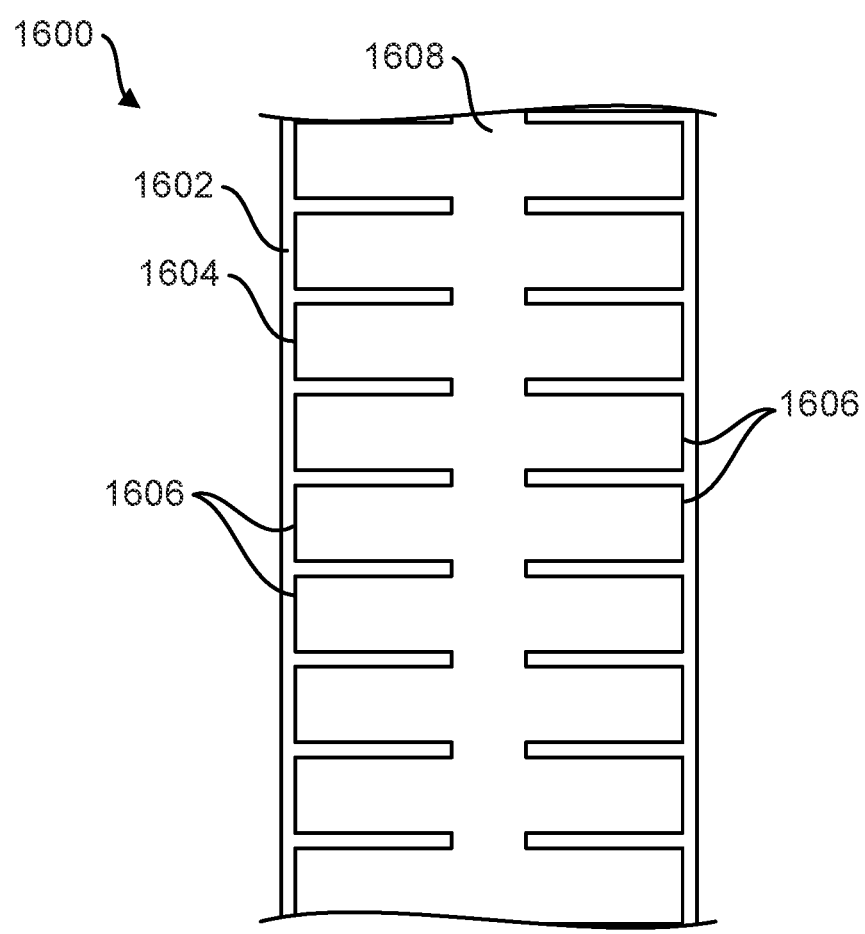
FIG. 16 is a schematic diagram of a side views of an example of an electrode, according to certain embodiments of the present disclosure.

FIG. 16 is a schematic diagram of a side view of an example of an electrode 1600 of an ablation assembly, in accordance with embodiments of the present disclosure. In some embodiments, the electrode is configured to receive energy from an energy source and deliver ablation energy to tissue at a target location in a patient. In certain embodiments, the electrode 1600 is a thin film electrode. In some embodiments, the electrode 1600 includes a thin film substrate or base 1602 that carries one or more conductors 1604. In certain embodiments, the base 1602 is made of a flexible/foldable material (such as an insulating polymer, more specifically a polyimide) and is movable from a first state or compressed state to a second state or expanded state and vice versa. In some embodiments, the conductor 1604 is made of one or more conductive metals, such as gold, platinum-iridium, copper, or the like. According to some embodiments, the base 1602 carries a single conductor 1604. In certain embodiments, the conductor 1604 includes a plurality of fingers 1606 that extend in opposite directions from a central portion 1608.

Figure 17A:
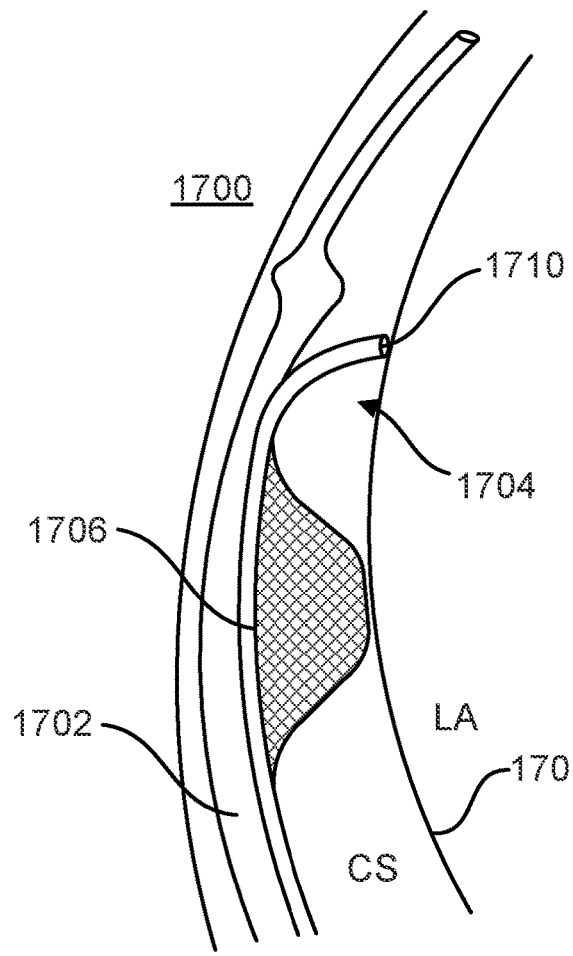
FIGS. 17A-17B are schematic diagrams of side views of an example of a shunting catheter, according to certain embodiments of the present disclosure.
Figure 17B:
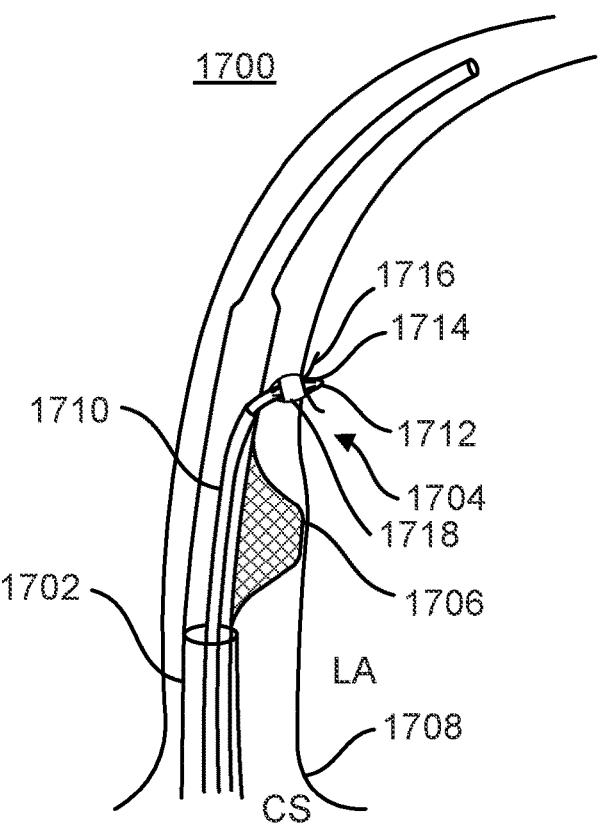

FIGS. 17A-B are schematic diagrams of side views of an example of a shunting catheter 1700, according to certain embodiments of the present disclosure. FIGS. 17A-B are merely examples. One of the ordinary skilled in the art would recognize many variations, alternatives, and modifications. In some embodiments and as shown, the shunting catheter 1700 includes a catheter shaft 1702 and an ablation assembly 1704.

In some embodiments, the ablation assembly 1704 is disposed within the catheter shaft 1702 at a first state (for example, during deployment, during deployment to position the ablation assembly 1704). In some embodiments, the ablation assembly 1704 is extended from the catheter shaft 1702 at a second state (for example, during shunting).

According to certain embodiments, the shunting catheter 1700 includes an apposition element 1706 configured to be disposed within the catheter shaft 1702 at a first state (for example, during deployment), and protrudes from the catheter shaft 1702 at a second state (for example, during shunting). According to some embodiments, for example during the tracking of the shunting catheter 1700 to a target location in a patient's CS, the ablation assembly 1704 may be translated out of the catheter shaft 1702 to puncture a target location on a wall 1708 (for example, a vessel wall between a patient's CS and LA). In embodiments, the apposition element 1706 is made of a flexible material and configured to appose a vessel wall 1708 (for example, a vessel wall between a patient's CS and LA) during shunting. In some embodiments, the apposition element 1706 provides stability to the shunting catheter 1700 during deployment and/or shunting.

In some embodiments, the ablation assembly 1704 includes a crimping shaft 1710 having a predetermined curve, a puncture element 1712, and an ablation mechanism 1714. In some embodiments, the ablation assembly 1704 may have a telescoping feature (for example, the puncture element 1712 and the ablation mechanism 1714 are retractable into the crimping shaft 1710) to allow for the blunt end of the crimping shaft 1710 to contact the wall 1708 before the puncture element 1712 is translated forward to make contact with the wall 1708. In certain embodiments, the telescoping feature of the ablation assembly 1704 allows for a safe delivery of the puncture element 1712 to the target location.

In some embodiments, for example as shown in FIG. 17A, the ablation assembly 1704 has a first deployment state where the crimping shaft 1710 and the ablation assembly 1704 are extended from the catheter shaft 1702, and the puncture element 1712 and the ablation mechanism 1714 are retracted and crimped inside the crimping shaft 1710. In certain embodiments and as shown, the distal end of the crimping shaft 1710 provides a blunt surface during the first deployment state, such that if adjustment of position is needed, the wall surrounding the target location would only make contact with a blunt surface.

In some embodiments, the ablation assembly 1704 has a second deployment state where the ablation mechanism 1714 and the puncture element 1712 are partially extended from the crimping shaft 1710. In certain embodiments, at the second deployment state a plurality of positioning elements 1716 of the ablation mechanism 1714 and the puncture element 1712 are extended from the crimping shaft 1710, and a plurality of expandable struts 1718 of the ablation mechanism 1714 are retracted in the lumen of the crimping shaft 1710. In certain embodiments, the puncture element 1712 punctures an opening in the wall 1708 in the patient upon moving from the first deployment state to the second deployment state. In some embodiments, the ablation assembly 1704 has a third deployment state where the ablation mechanism 1714 and the puncture element 1712 are further extended from the crimping shaft 1710. In some embodiments, at the third deployment state the plurality of positioning elements 1716 and the plurality of expandable struts 1718 of the ablation mechanism 1714 and the puncture element 1712 are extended from the crimping shaft 1710. In certain embodiments, the ablation assembly 1704 is expanded in the third deployment state and thereby enlarges the opening in the wall 1708 in the patient. In certain embodiments, the ablation assembly 1704 ablates tissue at the opening in the wall 1708 in the patient by delivering ablation energy (such as radiofrequency (RF) energy, phased RF energy, cryogenic energy, thermal energy, pulse energy, laser energy, microwave energy, ultrasound energy, and/or the like) to the tissue.

FIGS. 18A-18D are schematic diagrams of side views of an example of a shunting catheter 1800, according to certain embodiments of the present disclosure. FIGS. 18A-18D are merely examples. One of the ordinary skilled in the art would recognize many variations, alternatives, and modifications. In certain embodiments and as shown, the shunting catheter 1800 includes a catheter shaft 1802 and an ablation assembly 1804.

In some embodiments, the ablation assembly 1804 is disposed within the catheter shaft 1802 at a first state (for example, during deployment, during deployment to position the ablation assembly 1804). In some embodiments, the ablation assembly 1804 is extended from the catheter shaft 1802 at a second state (for example, during shunting). In certain embodiments, the ablation assembly 1804 is extended from an end of the catheter shaft 1802 at the second state.

Figure 18A:
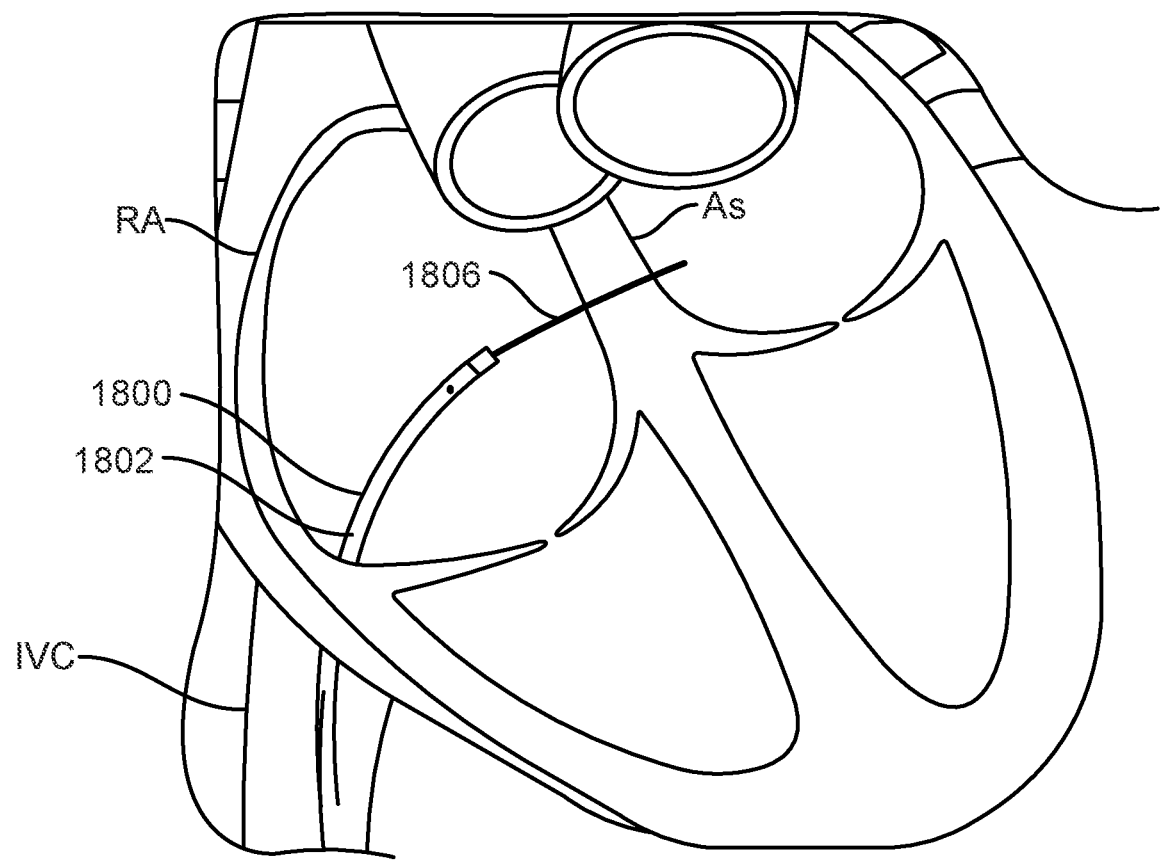
FIGS. 18A-18D are schematic diagrams of side views of another example of a shunting catheter, according to certain embodiments of the present disclosure.
Figure 18B:
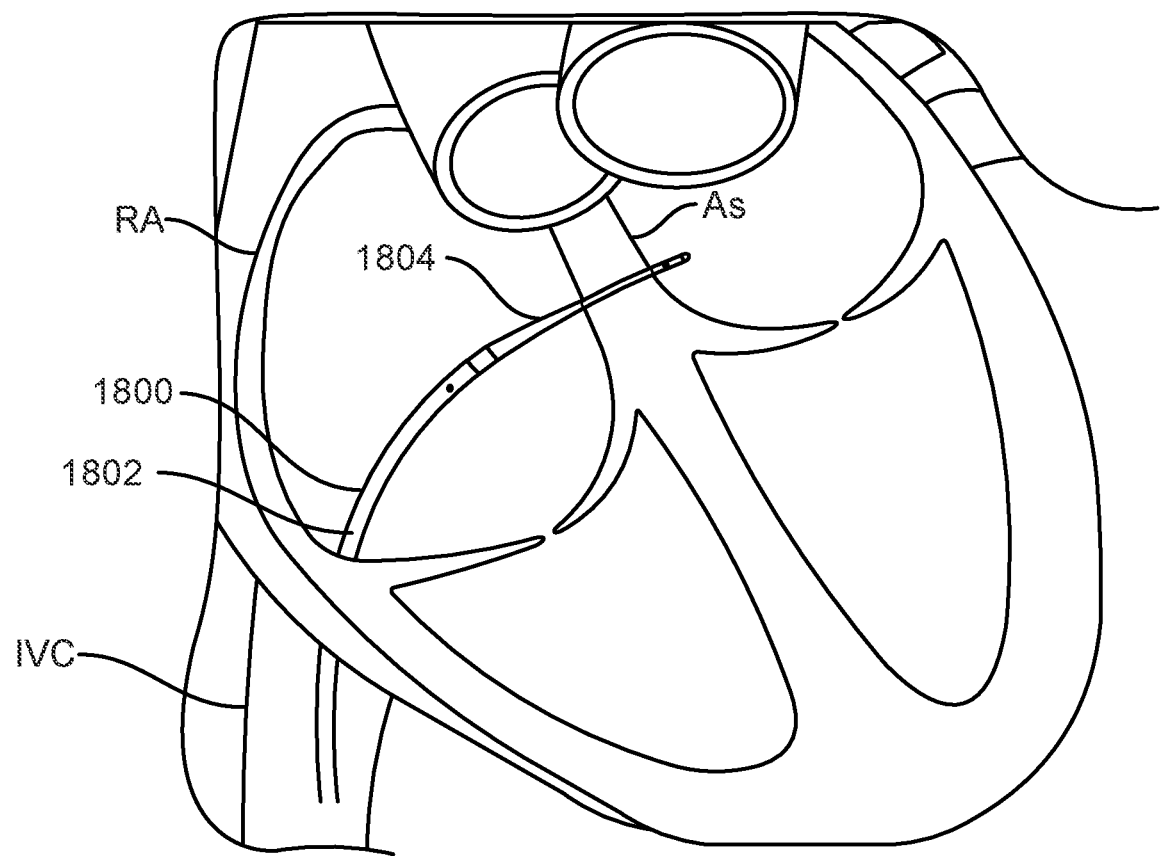
Figure 18C:
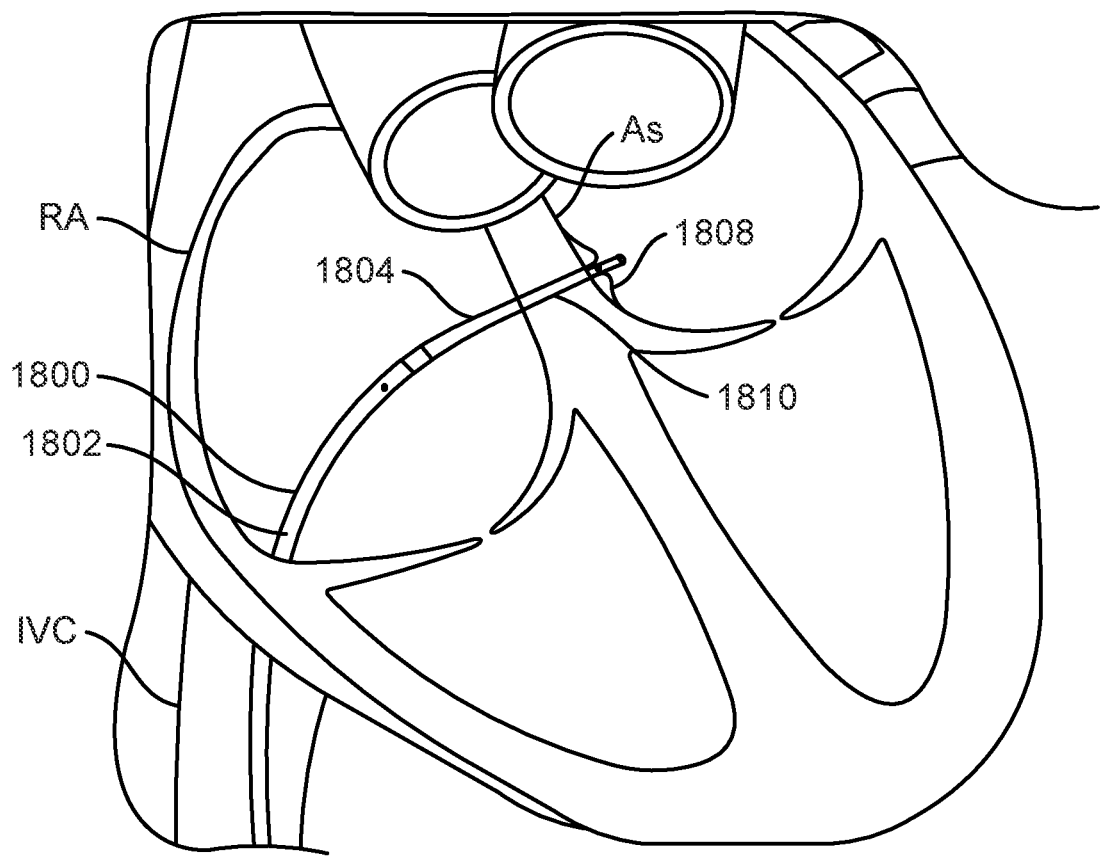
Figure 18D:
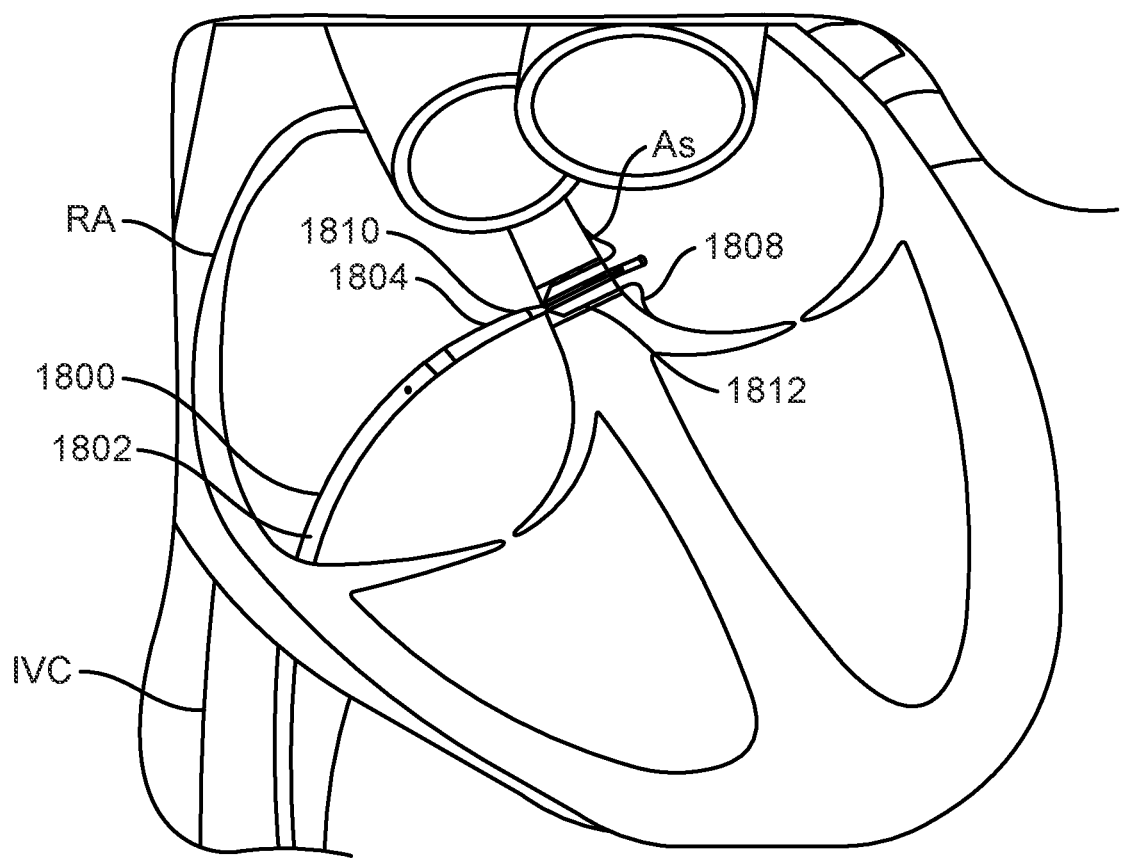

According to certain embodiments and as shown in FIG. 18A, a guidewire 1806 is advanced through the vasculature (for example, the IVC and the RA) and punctures an opening in the tissue at a target location in a patient (for example, the patient's AS). According to some embodiments and as shown in FIG. 18B, for example after using the guidewire 1806 to advance the shunting catheter 1800 to the target location in a patient's AS, the ablation assembly 1804 has a first deployment state in which the ablation assembly 1804 is translated out of the catheter shaft 1802 and enters the opening formed at the target location. In certain embodiments and as shown in FIG. 18C, the ablation assembly 1804 has a second deployment state in which the ablation assembly 1804 is partially expanded, more specifically a plurality of positioning elements 1808 of the ablation assembly 1804 are extended from a crimping shaft 1810, and a plurality of expandable struts 1812 (FIG. 18D) of the ablation assembly 1804 are retracted in the crimping shaft 1810. In some embodiments and as shown in FIG. 18D, the ablation assembly 1804 has a third deployment state in which the ablation assembly 1804 is further expanded, more specifically the plurality of expandable struts 1812 of the ablation assembly 1804 are extended from the crimping shaft 1810. In some embodiments, in the third deployment state the expandable struts 1812 are expanded and thereby enlarge the opening in the target location of the patient. In certain embodiments, the ablation assembly 1804 ablates tissue at the opening in the target location of the patient by delivering ablation energy (such as radiofrequency (RF) energy, phased RF energy, cryogenic energy, thermal energy, pulse energy, laser energy, microwave energy, ultrasound energy, and/or the like) to the tissue.

Figure 19:
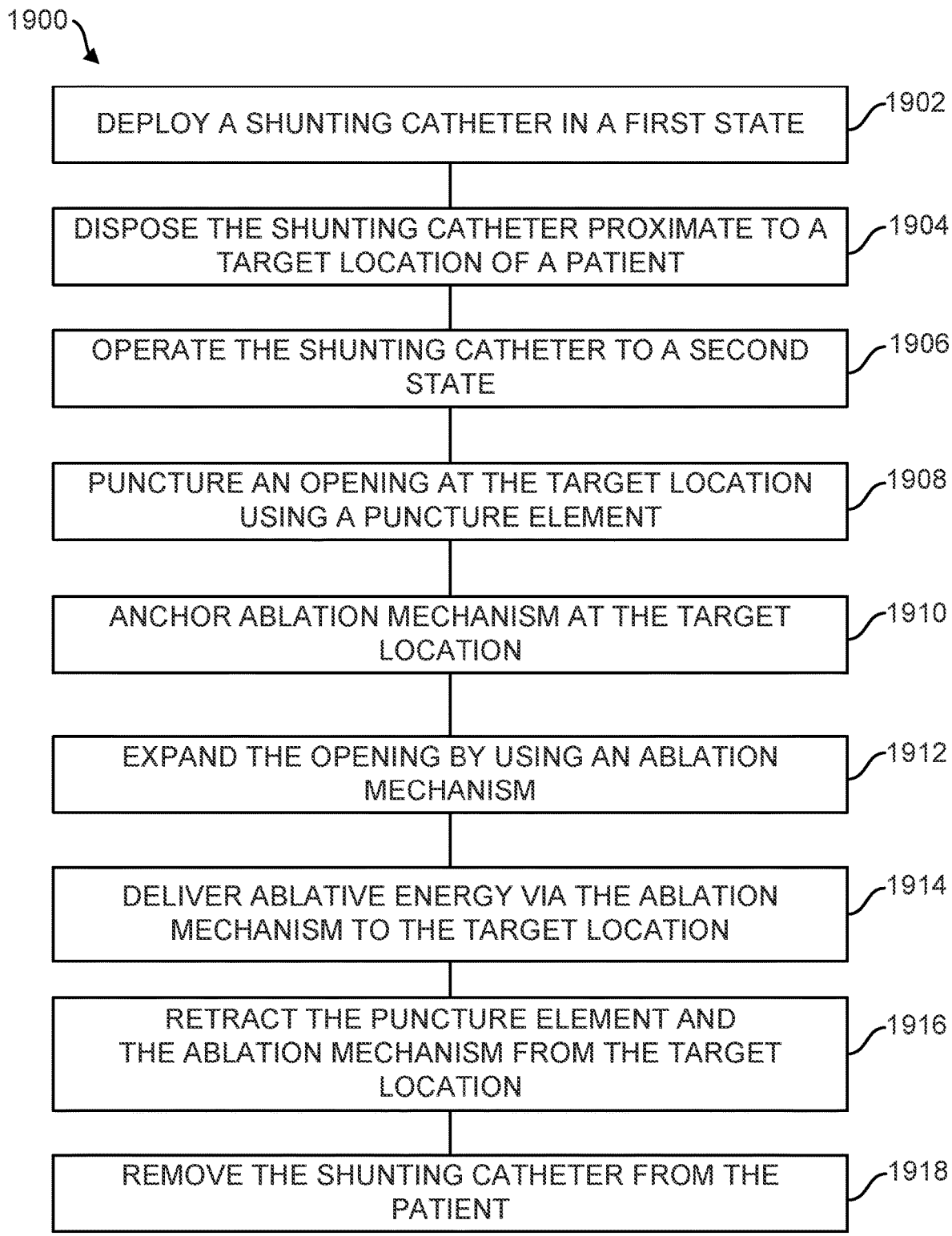
FIG. 19 is a flow diagram illustrating an example method of creating a shunt in a patient, in accordance with embodiments of the present disclosure.

FIG. 19 is a flow diagram illustrating an example method 1900 of creating a shunt in a patient, in accordance with embodiments of the present disclosure. Aspects of embodiments of the method may be performed, for example, by a shunting catheter system or a controller (for example, the system 104 in FIG. 1, the controller 112 in FIG. 1). One or more steps of method are optional and/or can be modified by one or more steps of other embodiments described herein. Additionally, one or more steps of other embodiments described herein may be added to the method. In some embodiments, the shunt may be formed in a coronary sinus of a patient. In certain embodiments, the shunt includes an opening between a patient's coronary sinus and left atrium.

At step 1902, the method 1900 includes deploying a shunting catheter in a first state, the shunting catheter including a catheter shaft including a shaft lumen and an ablation shaft disposed in the shaft lumen at the first state. In some embodiments, an ablation mechanism is disposed on the ablation shaft, and the ablation mechanism includes a plurality of expandable struts and a plurality of positioning elements. In some embodiments, the ablation mechanism is configured to receive energy (for example, electrical energy) from an energy source. In certain embodiments, deploying the shunting catheter includes inserting the shunting catheter through a superior vena cava of a patient into a coronary sinus of the patient. In certain embodiments, deploying the shunting catheter includes inserting the shunting catheter through an inferior vena cava of a patient into a coronary sinus of the patient.

At step 1904, the method 1900 includes disposing the shunting catheter proximate to a target location of a patient. At step 1906, the method 1900 includes operating the shunting catheter to a second state (more specifically, for example, a first deployment state), wherein the ablation shaft is extended from the catheter shaft. In certain embodiments, the ablation mechanism is disposed in the ablation shaft at the first deployment state. In some embodiments, the ablation shaft is extended from a side opening of the catheter shaft. In certain embodiments, the ablation shaft is extended from an end of the catheter shaft. In some embodiments, operating the shunting catheter to the second state further includes retracting a crimping shaft from a puncture element of the shunting catheter. In certain embodiments, in the second state a plurality of positioning elements and a plurality of expandable struts of the ablation mechanism are retracted in the crimping shaft. In some embodiments, the shunting catheter includes an apposition element disposed proximate to the ablation mechanism, and the apposition element is protruded from the catheter shaft at the second state.

At step 1908, the method 1900 includes puncturing, using the puncture element of the shunting catheter, an opening at the target location. In some embodiments, the target location is at a coronary sinus of a patient. In some embodiments, the puncture element physically contacts tissue to puncture an opening at the target location in the patient. Additionally or alternatively, the puncture element receives energy (for example, electrical energy) and delivers ablation energy (such as radiofrequency (RF) energy, phased RF energy, cryogenic energy, thermal energy, pulse energy, laser energy, ultrasound energy, microwave energy, and/or the like) to tissue to puncture an opening at the target location in the patient. In some instances, the method 1900 may include stabilizing the ablation mechanism in the second state, and before puncturing the opening at the target location.

At step 1910, the method 1900 includes anchoring the ablation mechanism at the target location in the second state (more specifically, for example, in a second deployment state). In certain embodiments, such anchoring includes contacting the positioning elements of the ablation mechanism, which are extended from the crimping shaft in the second deployment state, against tissue at the target location of the patient. In certain embodiments, such anchoring includes contacting curved distal ends of the positioning elements, which define soft landing zones, against tissue at the target location of the patient. In some embodiments, contacting the positioning elements against tissue at the target location of the patient includes permitting the positioning elements to self-expand in the second deployment state. In some embodiments, in the second deployment state the expandable struts are retracted in the crimping shaft.

At step 1912, the method 1900 includes expanding the opening in the tissue using the ablation mechanism in the second state (more specifically, for example, in a third deployment state). In certain embodiments, the expandable struts are extended from the crimping shaft in the third deployment state. In some embodiments, expanding the opening includes permitting the expandable struts to self-expand in the third deployment state. In some embodiments, expanding the opening includes expanding the expandable struts by operating an actuator, for example inflating a balloon carried within the ablation mechanism.

At step 1914, the method 1900 includes delivering ablation energy (such as radiofrequency (RF) energy, phased RF energy, cryogenic energy, thermal energy, pulse energy, laser energy, ultrasound energy, microwave energy, and/or the like) via the ablation mechanism to tissue at the target location. In some embodiments, the ablation mechanism delivers the ablation energy while expanded in the second state, more specifically the third deployment state. In some embodiments, delivering the ablation energy to the tissue at the target location solidifies the opening at the target location.

At step 1916, the method 1900 includes retracting the puncture element and the ablation mechanism from the tissue at the target location in the patient. In certain embodiments, retracting the puncture element and the ablation mechanism includes moving the puncture element and the ablation mechanism into the crimping shaft. In certain embodiments, retracting the puncture element and the ablation mechanism includes compressing the ablation mechanism in the crimping shaft.

At step 1918, the method 1900 includes removing the shunting catheter from the patient. In some embodiments, the method 1900 may include removing the shunting catheter, which includes removing the catheter shaft, the puncture element, and the ablation mechanism. In certain embodiments, the method 1900 does not leave any implant device at the target location. In some embodiments, the formed shunt is an opening between a coronary sinus and a left atrium of a patient. In certain embodiments, the shunting catheter is removed from the coronary sinus of the patient. In certain embodiments, the formed shunt is an opening that does not include an implant (for example, a frame or structure to support an opening). In some embodiments, the shunt includes an opening between the coronary sinus and the left atrium of a patient, where the shunt does not include an implant.

According to some embodiments, the method 1900 includes generating a shunt using a puncture element and an ablation mechanism of a shunting catheter. In certain embodiments, the shunt includes an expanded opening between the coronary sinus and left atrium of a patient. In some embodiments, the shunt does not include any implant.

Figure 20:
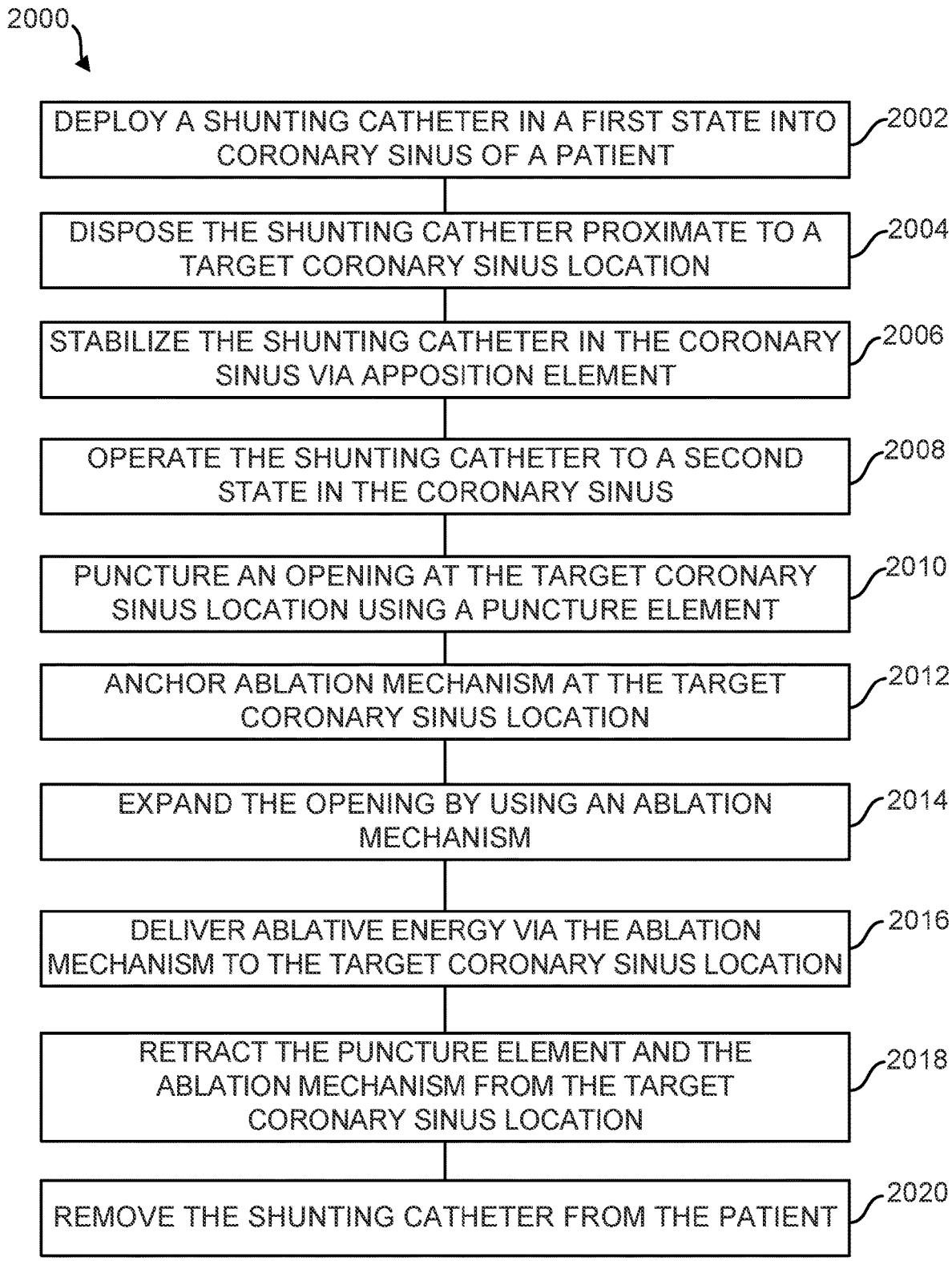
FIG. 20 is a flow diagram illustrating another example method of creating a shunt in a patient, in accordance with embodiments of the present disclosure.

FIG. 20 is a flow diagram illustrating an example method 2000 of creating a shunt in a patient, in accordance with embodiments of the present disclosure. Aspects of embodiments of the method may be performed, for example, by a shunting catheter system or a controller (for example, the system 104 in FIG. 1, the controller 112 in FIG. 1). One or more steps of method are optional and/or can be modified by one or more steps of other embodiments described herein. Additionally, one or more steps of other embodiments described herein may be added to the method.

At step 2002, the method 2000 includes deploying a shunting catheter in a first state into a coronary sinus of a patient, the shunting catheter including a catheter shaft including a shaft lumen and an ablation shaft disposed in the shaft lumen at the first state. In some embodiments, an ablation mechanism is disposed on the ablation shaft, and the ablation mechanism includes a plurality of expandable struts and a plurality of positioning elements. In some embodiments, the ablation mechanism is configured to receive energy (for example, electrical energy) from an energy source. In certain embodiments, deploying the shunting catheter includes inserting the shunting catheter through a superior vena cava of a patient into the coronary sinus of the patient. In certain embodiments, deploying the shunting catheter includes inserting the shunting catheter through an inferior vena cava of a patient into the coronary sinus of the patient.

At step 2004, the method 2000 includes disposing the shunting catheter proximate to a target coronary sinus location of a patient. At step 2006, the method 2000 includes stabilizing the ablation mechanism in the coronary sinus by using an apposition element of the shunting catheter.

At step 2008, the method 2000 includes operating the shunting catheter to a second state (more specifically, for example, a first deployment state), wherein the ablation shaft is extended from the catheter shaft. In certain embodiments, the ablation mechanism is disposed in the ablation shaft at the first deployment state. In some embodiments, the ablation shaft is extended from a side opening of the catheter shaft. In certain embodiments, the ablation shaft is extended from an end of the catheter shaft. In some embodiments, operating the shunting catheter to the second state further includes retracting a crimping shaft from a puncture element of the shunting catheter. In certain embodiments, in the second state a plurality of positioning elements and a plurality of expandable struts of the ablation mechanism are retracted in the crimping shaft.

At step 2010, the method 2000 includes puncturing, using the puncture element of the shunting catheter, an opening at the target coronary sinus location. In some embodiments, the puncture element physically contacts coronary sinus tissue to puncture an opening at the target coronary sinus location in the patient. Additionally or alternatively, the puncture element receives energy (for example, electrical energy) and delivers ablation energy (such as radiofrequency (RF) energy, phased RF energy, cryogenic energy, thermal energy, pulse energy, laser energy, ultrasound energy, microwave energy, and/or the like) to tissue to puncture an opening at the target coronary sinus location in the patient.

At step 2012, the method 2000 includes anchoring the ablation mechanism at the target coronary sinus location in the second state (more specifically, for example, in a second deployment state). In certain embodiments, such anchoring includes contacting the positioning elements of the ablation mechanism, which are extended from the crimping shaft in the second deployment state, against tissue at the target coronary sinus location of the patient. In certain embodiments, such anchoring includes contacting curved distal ends of the positioning elements, which define soft landing zones, against tissue at the target coronary sinus location of the patient. In some embodiments, contacting the positioning elements against tissue at the target coronary sinus location of the patient includes permitting the positioning elements to self-expand in the second deployment state. In some embodiments, in the second deployment state the expandable struts are retracted in the crimping shaft.

At step 2014, the method 2000 includes expanding the opening in the tissue using the ablation mechanism in the second state (more specifically, for example, in a third deployment state). In certain embodiments, the expandable struts are extended from the crimping shaft in the third deployment state. In some embodiments, expanding the opening includes permitting the expandable struts to self-expand in the third deployment state. In some embodiments, expanding the opening includes expanding the expandable struts by operating an actuator, for example inflating a balloon carried within the ablation mechanism.

At step 2016, the method 2000 includes delivering ablation energy (such as radiofrequency (RF) energy, phased RF energy, cryogenic energy, thermal energy, pulse energy, laser energy, ultrasound energy, microwave energy, and/or the like) via the ablation mechanism to tissue at the target coronary sinus location. In some embodiments, the ablation mechanism delivers the ablation energy while expanded in the second state, more specifically the third deployment state. In some embodiments, delivering the ablation energy to the tissue at the target coronary sinus location solidifies the opening at the target coronary sinus location.

At step 2018, the method 2000 includes retracting the puncture element and the ablation mechanism from the tissue at the target coronary sinus location in the patient. In certain embodiments, retracting the puncture element and the ablation mechanism includes moving the puncture element and the ablation mechanism into the crimping shaft. In certain embodiments, retracting the puncture element and the ablation mechanism includes compressing the ablation mechanism in the crimping shaft.

At step 2020, the method 2000 includes removing the shunting catheter from the patient. In some embodiments, the method 2000 may include removing the shunting catheter, which includes removing the catheter shaft, the puncture element, and the ablation mechanism. In certain embodiments, the method 2000 does not leave any implant device at the target coronary sinus location. In some embodiments, the formed shunt is an opening between the coronary sinus and the left atrium of a patient. In certain embodiments, the shunting catheter is removed from the coronary sinus of the patient. In certain embodiments, the formed shunt is an opening that does not include an implant (for example, a frame or structure to support an opening). In some embodiments, the shunt includes an opening between the coronary sinus and the left atrium of a patient, where the shunt does not include an implant.

According to some embodiments, the method 2000 includes generating a shunt using a puncture element and an ablation mechanism of a shunting catheter. In certain embodiments, the shunt includes an expanded opening between the coronary sinus and left atrium of a patient. In some embodiments, the shunt does not include any implant.

Figure 21:
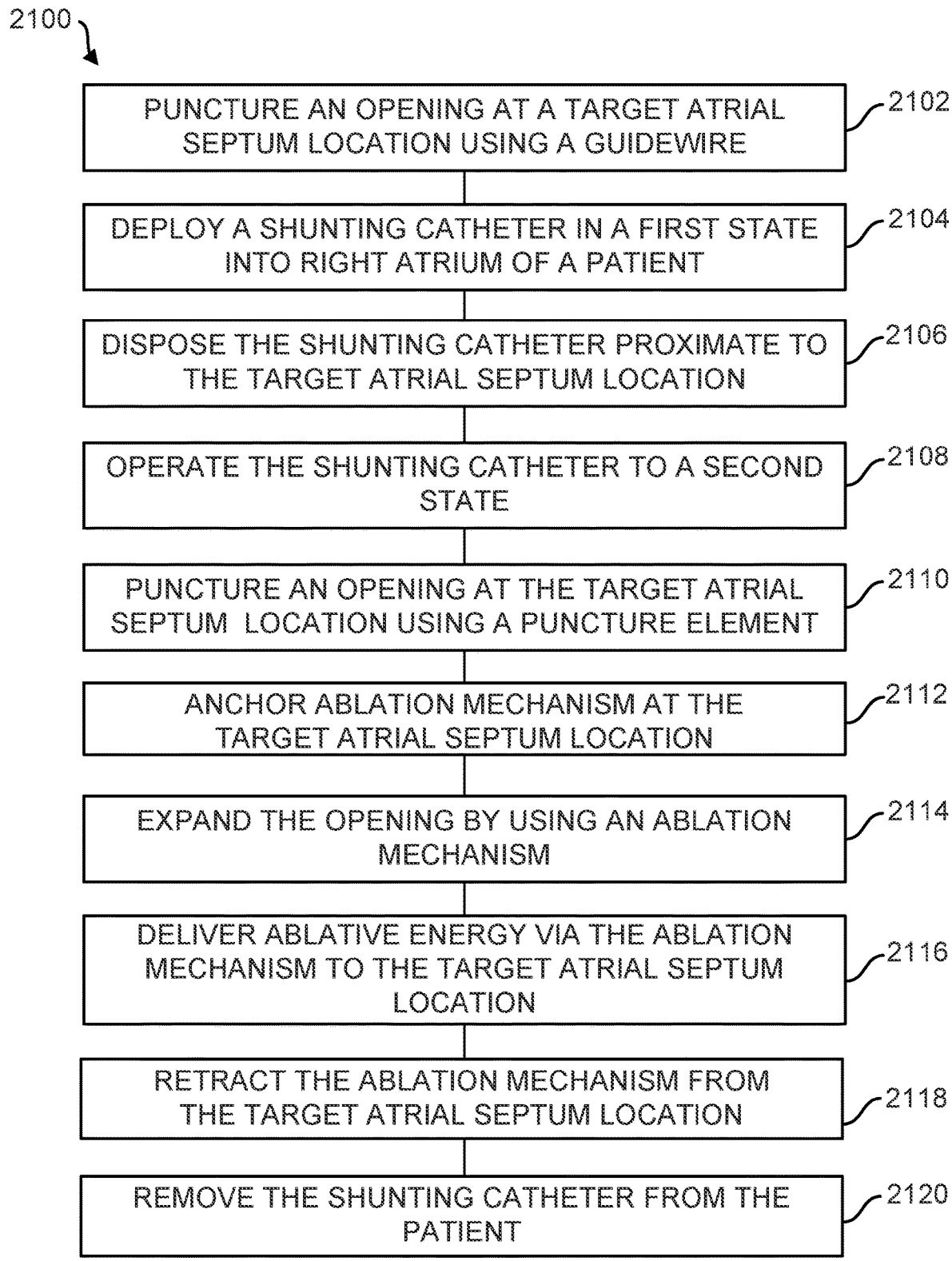
FIG. 21 is a flow diagram illustrating yet another example method of creating a shunt in a patient, in accordance with embodiments of the present disclosure.

FIG. 21 is a flow diagram illustrating an example method 2100 of creating a shunt in a patient, in accordance with embodiments of the present disclosure. Aspects of embodiments of the method may be performed, for example, by a shunting catheter system or a controller (for example, the system 104 in FIG. 1, the controller 112 in FIG. 1). One or more steps of method are optional and/or can be modified by one or more steps of other embodiments described herein. Additionally, one or more steps of other embodiments described herein may be added to the method.

At step 2102, the method 2100 includes puncturing, using a guidewire, an opening at a target atrial septum location in a patient. In some embodiments, the guidewire is inserted through an inferior vena cava of the patient into the RA of the patient to puncture the opening at the target atrial septum location. In some embodiments, the guidewire is inserted through a superior vena cava of the patient into the RA of the patient to puncture the opening at the target atrial septum location.

At step 2104, the method 2100 includes deploying a shunting catheter in a first state into a right atrium (RA) of a patient, the shunting catheter including a catheter shaft including a shaft lumen and an ablation shaft disposed in the shaft lumen at the first state. In certain embodiments, an ablation mechanism is disposed on the ablation shaft, and the ablation mechanism includes a plurality of positioning elements and a plurality of expandable struts. In some embodiments, the ablation mechanism is configured to receive energy from an energy source. In certain embodiments, the shunting catheter tracks along the guidewire to deploy into the RA of the patient. In certain embodiments, deploying the shunting catheter includes inserting the shunting catheter through the inferior vena cava of the patient into the RA of the patient. In certain embodiments, deploying the shunting catheter includes inserting the shunting catheter through the superior vena cava of the patient into the RA of the patient.

At step 2106, the method 2100 includes disposing the shunting catheter proximate to the target atrial septum location of the patient. In some embodiments, the shunting catheter is disposed proximate to the target atrial septum location by advancing the shunting catheter along the guidewire.

At step 2108, the method 2100 includes operating the shunting catheter to a second state (more specifically, for example, a first deployment state), wherein the ablation shaft is extended from the catheter shaft. In certain embodiments, the ablation mechanism is disposed in the ablation shaft at the first deployment state. In some embodiments, the ablation shaft is extended from a side opening of the catheter shaft. In certain embodiments, the ablation shaft is extended from an end of the catheter shaft. In some embodiments, operating the shunting catheter to the second state further includes retracting a crimping shaft from a puncture element of the shunting catheter. In certain embodiments, in the first deployment state a plurality of positioning elements and a plurality of expandable struts of the ablation mechanism are retracted in the crimping shaft.

At step 2110, the method 2100 includes puncturing, using the puncture element of the shunting catheter, an opening at the target atrial septum location. In some embodiments, the puncture element physically contacts atrial septum tissue to puncture an opening at the target atrial septum location in the patient. Additionally or alternatively, the puncture element receives energy (for example, electrical energy) and delivers ablation energy (such as radiofrequency (RF) energy, phased RF energy, cryogenic energy, thermal energy, pulse energy, laser energy, ultrasound energy, microwave energy, and/or the like) to tissue to puncture an opening at the target atrial septum location in the patient.

At step 2112, the method 2100 includes anchoring the ablation mechanism at the target atrial septum location in the second state (more specifically, for example, in a second deployment state). In certain embodiments, such anchoring includes contacting the positioning elements of the ablation mechanism, which are extended from the crimping shaft in the second deployment state, against tissue at the target atrial septum location of the patient. In certain embodiments, such anchoring includes contacting curved distal ends of the positioning elements, which define soft landing zones, against tissue at the target atrial septum location of the patient. In some embodiments, contacting the positioning elements against tissue at the target atrial septum location of the patient includes permitting the positioning elements to self-expand in the second deployment state. In some embodiments, in the second deployment state the expandable struts are retracted in the crimping shaft.

At step 2114, the method 2100 includes expanding the opening in the tissue using the ablation mechanism in the second state (more specifically, for example, in a third deployment state). In certain embodiments, the expandable struts are extended from the crimping shaft in the third deployment state. In some embodiments, expanding the opening includes permitting the expandable struts to self-expand in the third deployment state. In some embodiments, expanding the opening includes expanding the expandable struts by operating an actuator, for example inflating a balloon carried within the ablation mechanism.

At step 2116, the method 2100 includes delivering ablation energy (such as radiofrequency (RF) energy, phased RF energy, cryogenic energy, thermal energy, pulse energy, laser energy, ultrasound energy, microwave energy, and/or the like) via the ablation mechanism to tissue at the target atrial septum location. In some embodiments, the ablation mechanism delivers the ablation energy while expanded in the second state, more specifically the third deployment state. In some embodiments, delivering the ablation energy to the tissue at the target atrial septum location solidifies the opening at the target atrial septum location.

At step 2118, the method 2100 includes retracting the puncture element and the ablation mechanism from the tissue at the target atrial septum location in the patient. In certain embodiments, retracting the puncture element and the ablation mechanism includes moving the puncture element and the ablation mechanism into the crimping shaft. In certain embodiments, retracting the puncture element and the ablation mechanism includes compressing the ablation mechanism in the crimping shaft.

At step 2120, the method 2100 includes removing the shunting catheter from the patient. In some embodiments, the method 2100 may include removing the shunting catheter, which includes removing the catheter shaft, the puncture element, and the ablation mechanism. In certain embodiments, the method 2100 does not leave any implant device at the target atrial septum location. In some embodiments, the formed shunt is an opening in the atrial septum of the patient. In certain embodiments, the shunting catheter is removed from the RA of the patient. In certain embodiments, the formed shunt is an opening that does not include an implant (for example, a frame or structure to support an opening). In some embodiments, the shunt includes an opening in the atrial septum of a patient, where the shunt does not include an implant.

According to some embodiments, the method 2100 includes generating a shunt using a puncture element and an ablation mechanism of a shunting catheter. In certain embodiments, the shunt includes an expanded opening in the atrial septum of a patient. In some embodiments, the shunt does not include any implant. In certain embodiments, the method 2100 does not include using a shunting catheter; more specifically, the ablation catheter may be advanced directly over the guidewire to the target atrial septum location.

According to some embodiments, a shunting catheter includes: a catheter shaft including a shaft lumen; an ablation shaft disposed in the shaft lumen at a first state and extended from the catheter shaft at a second state; and an ablation mechanism disposed on the ablation shaft and expandable at the second state, the ablation mechanism including: a plurality of expandable struts; and a plurality of positioning elements coupled to the plurality of expandable struts and disposed radially outwardly from the plurality of expandable struts at the second state; wherein the ablation mechanism is configured to receive energy from an energy source and deliver ablation energy to a target location of a patient.

According to some embodiments, further including a crimping shaft including a lumen, wherein the second state of the shunting catheter includes a first deployment state, a second deployment state, and a third deployment state, in the first deployment state the plurality of positioning elements and the plurality of expandable struts are retracted in the lumen of the crimping shaft, in the second deployment state the plurality of positioning elements extend outwardly from the lumen of the crimping shaft and the plurality of expandable struts are retracted in the lumen of the crimping shaft, and in the third deployment state the plurality of positioning elements and the plurality of expandable struts extend outwardly from the lumen of the crimping shaft.

According to certain embodiments, a portion of the ablation mechanism includes an insulator configured to inhibit transmission of the ablation energy therethrough.

According to some embodiments, the insulator covers at least one of the plurality of expandable struts.

According to certain embodiments, the insulator covers at least one of the plurality of positioning elements.

According to some embodiments, the insulator includes a heat shrink tube, a polytetrafluoroethylene (PTFE) tube, an expanded polytetrafluoroethylene (ePTFE) tube, or a polyimide tube.

According to certain embodiments, at least one of the positioning elements of the plurality of positioning elements includes a curved distal end defining a soft landing zone configured to contact tissue at the target location of the patient.

According to certain embodiments, the plurality of positioning elements includes a first positioning element and a second positioning element, the second positioning element being longitudinally offset from the first positioning element.

According to some embodiments, the ablation mechanism further includes a plurality of connector struts, each connector strut of the plurality of connector struts disposed between and coupling adjacent expandable struts of the plurality of expandable struts.

According to certain embodiments, the ablation mechanism further includes a plurality of iris elements disposed radially outwardly from the plurality of expandable struts, the plurality of iris elements together defining an expandable iris assembly.

According to some embodiments, the ablation mechanism further includes at least one electrode disposed on the expandable iris assembly and configured to deliver the ablation energy to the target location of the patient.

According to certain embodiments, the plurality of expandable struts are configured to act as electrodes and deliver the ablation energy to the target location of the patient.

According to some embodiments, the ablation mechanism further includes at least one electrode disposed on at least one of the plurality of expandable struts and configured to deliver the ablation energy to the target location of the patient.

According to certain embodiments, the plurality of expandable struts are self-expandable at the second state.

According to some embodiments, further including an actuator being actuatable to expand the ablation mechanism.

According to certain embodiments, the actuator includes an inflatable balloon.

According to some embodiments, further including a temperature sensor coupled to the ablation mechanism.

According to certain embodiments, the plurality of expandable struts includes at least one selected from a group consisting of nitinol, stainless steel, titanium, platinum-iridium, and cobalt-chromium.

According to some embodiments, the catheter shaft defines a first axis, the ablation shaft defines a second axis at the second state, and the second axis and the first axis form an angle greater than zero degrees.

According to certain embodiments, the plurality of positioning elements include a flexible material.

According to some embodiments, the plurality of positioning elements are integrally formed with the plurality of expandable struts.

According to certain embodiments, the plurality of positioning elements includes at least one radiopaque marker.

According to some embodiments, a shunting catheter system includes: a shunting catheter, including: a catheter shaft including a shaft lumen; an ablation shaft disposed in the shaft lumen at a first state and extended from the catheter shaft at a second state; and an ablation mechanism disposed on the ablation shaft, the ablation mechanism including: a plurality of expandable struts defining an expandable cage; a plurality of positioning elements coupled to the plurality of expandable struts and disposed outwardly from the expandable cage at the second state; an energy source connected to the shunting catheter; and a controller connected to the energy source and including a processor; wherein the processor is configured to control the energy source to deliver ablation energy to a target location of a patient via the ablation mechanism.

According to certain embodiments, further including a crimping shaft including a lumen, wherein the second state of the shunting catheter includes a first deployment state, a second deployment state, and a third deployment state, in the first deployment state the plurality of positioning elements and the plurality of expandable struts are retracted in the lumen of the crimping shaft, in the second deployment state the plurality of positioning elements extend outwardly from the lumen of the crimping shaft and the plurality of expandable struts are retracted in the lumen of the crimping shaft, and in the third deployment state the plurality of positioning elements and the plurality of expandable struts extend outwardly from the lumen of the crimping shaft.

According to some embodiments, a portion of the ablation mechanism includes an insulator configured to inhibit transmission of the ablation energy therethrough.

According to certain embodiments, the insulator covers at least one of the plurality of expandable struts.

According to some embodiments, the insulator covers at least one of the plurality of positioning elements.

According to certain embodiments, the insulator includes a heat shrink tube, a polytetrafluoroethylene (PTFE) tube, an expanded polytetrafluoroethylene (ePTFE) tube, or a polyimide tube.

According to some embodiments, at least one of the positioning elements of the plurality of positioning elements includes a curved distal end defining a soft landing zone configured to contact tissue at the target location of the patient.

According to certain embodiments, the plurality of positioning elements includes a first positioning element and a second positioning element, the second positioning element being longitudinally offset from the first positioning element.

According to some embodiments, the ablation mechanism further includes a plurality of connector struts, each connector strut of the plurality of connector struts disposed between and coupling adjacent expandable struts of the plurality of expandable struts.

According to certain embodiments, the ablation mechanism further includes a plurality of iris elements disposed radially outwardly from the plurality of expandable struts, the plurality of iris elements together defining an expandable iris assembly.

According to some embodiments, the ablation mechanism further includes at least one electrode disposed on the expandable iris assembly and configured to deliver the ablation energy to the target location of the patient.

According to certain embodiments, the plurality of expandable struts act as electrodes and are configured to deliver the ablation energy to the target location of the patient.

According to some embodiments, the ablation mechanism further includes at least one electrode connected to the expandable cage and configured to deliver the ablation energy to the target location of the patient.

According to certain embodiments, the ablation energy includes at least one of radiofrequency (RF) energy, phased RF energy, cryogenic energy, thermal energy, pulse energy, laser energy, ultrasound energy, microwave energy.

According to certain embodiments, the plurality of expandable struts are self-expandable at the second state.

According to some embodiments, the shunting catheter further includes an actuator being actuatable to expand the expandable cage.

According to certain embodiments, the actuator includes an inflatable balloon.

According to some embodiments, the plurality of positioning elements include a flexible material.

According to certain embodiments, the plurality of positioning elements are integrally formed with the expandable cage.

According to some embodiments, a method for creating a shunt includes: deploying a shunting catheter in a first state, the shunting catheter including: a catheter shaft including a shaft lumen; an ablation shaft disposed in the shaft lumen at a first state; and an ablation mechanism disposed on the ablation shaft and including a plurality of expandable struts and a plurality of positioning elements; disposing the shunting catheter proximate to a target location of a patient; operating the shunting catheter to a second state, wherein the ablation shaft and the ablation mechanism extend from the catheter shaft; contacting at least one of the plurality of positioning elements against tissue at the target location of the patient; expanding an opening at the target location of the patient by expanding the plurality of expandable struts; and delivering ablation energy via the ablation mechanism to the target location of the patient.

According to certain embodiments, the shunting catheter further includes a crimping shaft including a lumen, and operating the shunting catheter to the second state includes operating the shunting catheter to a first deployment state, then a second deployment state, and then a third deployment state, in the first deployment state the plurality of positioning elements and the plurality of expandable struts are retracted in the lumen of the crimping shaft, in the second deployment state the plurality of positioning elements extend outwardly from the lumen of the crimping shaft and the plurality of expandable struts are retracted in the lumen of the crimping shaft, and in the third deployment state the plurality of positioning elements and the plurality of expandable struts extend outwardly from the lumen of the crimping shaft.

According to some embodiments, the at least one of the positioning elements includes a curved distal end defining a soft landing zone, and contacting the at least one of the positioning elements against the tissue at the target location of the patient includes contacting the soft landing zone against the tissue at the target location of the patient.

According to certain embodiments, contacting the at least one of the positioning elements against tissue at the target location of the patient includes permitting the at least one of the plurality of positioning elements to self-expand.

According to some embodiments, permitting the at least one of the positioning elements to self-expand includes retracting a crimping shaft from the at least one of the plurality of positioning elements.

According to certain embodiments, expanding the plurality of expandable struts includes permitting the plurality of expandable struts to self-expand.

According to some embodiments, permitting the plurality of expandable struts to self-expand includes retracting a crimping shaft from the plurality of expandable struts.

According to certain embodiments, contacting the at least one of the positioning elements against tissue at the target location of the patient precedes expanding the opening at the target location of the patient by expanding the plurality of expandable struts.

According to some embodiments, a portion of the ablation mechanism includes an insulator configured to inhibit transmission of the ablation energy therethrough.

According to certain embodiments, the insulator covers at least one of the plurality of expandable struts.

According to some embodiments, the insulator covers at least one of the plurality of positioning elements.

According to certain embodiments, the insulator includes a heat shrink tube, a polytetrafluoroethylene (PTFE) tube, an expanded polytetrafluoroethylene (ePTFE) tube, or a polyimide tube.

According to some embodiments, the plurality of positioning elements includes a first positioning element and a second positioning element, the second positioning element being longitudinally offset from the first positioning element.

According to certain embodiments, the ablation mechanism further includes a plurality of connector struts, each connector strut of the plurality of connector struts disposed between and coupling adjacent expandable struts of the plurality of expandable struts.

According to some embodiments, the ablation mechanism further includes a plurality of iris elements disposed radially outwardly from the plurality of expandable struts, the plurality of iris elements together defining an expandable iris assembly, and expanding the opening at the target location of the patient further includes expanding the expandable iris assembly.

According to certain embodiments, the ablation mechanism further includes at least one electrode disposed on the expandable iris assembly, and delivering ablation energy via the ablation mechanism to the target location includes delivering ablation energy via the at least one electrode.

According to some embodiments, delivering the ablation energy includes delivering the ablation energy via the plurality of expandable struts to the target location of the patient.

According to certain embodiments, the ablation mechanism further includes at least one electrode connected to the plurality of expandable struts, and wherein delivering the ablation energy includes delivering the ablation energy via the at least one electrode to the target location of the patient.

According to some embodiments, the shunting catheter further includes an actuator, and wherein expanding the plurality of expandable struts includes actuating the actuator to expand the plurality of expandable struts.

According to certain embodiments, expanding the plurality of expandable struts includes inflating a balloon to expand the plurality of expandable struts.

According to some embodiments, the target location is at a coronary sinus of the patient.

According to certain embodiments, the target location is at an atrial septum of the patient.

Various modifications and additions can be made to the exemplary embodiments discussed without departing from the scope of the present disclosure. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A shunting catheter, comprising:
a catheter shaft including a shaft lumen;
an ablation shaft disposed in the shaft lumen at a first state and extended from the catheter shaft at a second state;
an ablation mechanism disposed on the ablation shaft and expandable at the second state, the ablation mechanism comprising:
a plurality of expandable struts;
a plurality of positioning elements coupled to the plurality of expandable struts and disposed radially outwardly from the plurality of expandable struts at the second state; and
a crimping shaft comprising a lumen;
wherein the ablation mechanism is configured to receive energy from an energy source and deliver ablation energy to a target location of a patient, and
wherein the second state of the shunting catheter comprises a first deployment state, a second deployment state, and a third deployment state, in the first deployment state the plurality of positioning elements and the plurality of expandable struts are retracted in the lumen of the crimping shaft, in the second deployment state the plurality of positioning elements extend outwardly from the lumen of the crimping shaft and the plurality of expandable struts are retracted in the lumen of the crimping shaft, and in the third deployment state the plurality of positioning elements and the plurality of expandable struts extend outwardly from the lumen of the crimping shaft.

2. The shunting catheter of claim 1, wherein a portion of the ablation mechanism comprises an insulator configured to inhibit transmission of the ablation energy therethrough.

3. The shunting catheter of claim 2, wherein the insulator covers at least one of the plurality of expandable struts.

4. The shunting catheter of claim 2, wherein the insulator covers at least one of the plurality of positioning elements.

5. The shunting catheter of claim 2, wherein the insulator comprises a heat shrink tube, a polytetrafluoroethylene (PTFE) tube, an expanded polytetrafluoroethylene (ePTFE) tube, or a polyimide tube.

6. The shunting catheter of claim 1, wherein at least one of the positioning elements of the plurality of positioning elements comprises a curved distal end defining a soft landing zone configured to contact tissue at the target location of the patient.

7. The shunting catheter of claim 1, wherein the plurality of positioning elements comprises a first positioning element and a second positioning element, the second positioning element being longitudinally offset from the first positioning element.

8. The shunting catheter of claim 1, wherein the ablation mechanism further comprises a plurality of connector struts, each connector strut of the plurality of connector struts disposed between and coupling adjacent expandable struts of the plurality of expandable struts.

9. The shunting catheter of claim 1, wherein the ablation mechanism further comprises a plurality of iris elements disposed radially outwardly from the plurality of expandable struts, the plurality of iris elements together defining an expandable iris assembly.

10. The shunting catheter of claim 1, wherein the plurality of expandable struts are configured to act as electrodes and deliver the ablation energy to the target location of the patient.

11. The shunting catheter of claim 1, wherein the ablation mechanism further comprises at least one electrode disposed on at least one of the plurality of expandable struts and configured to deliver the ablation energy to the target location of the patient.

12. The shunting catheter of claim 1, wherein the plurality of expandable struts are self-expandable at the second state.

13. The shunting catheter of claim 1, further comprising a temperature sensor coupled to the ablation mechanism.

14. The shunting catheter of claim 1, wherein the catheter shaft defines a first axis, the ablation shaft defines a second axis at the second state, and the second axis and the first axis form an angle greater than zero degrees.

15. The shunting catheter of claim 1, wherein the plurality of positioning elements comprise a flexible material.

16. The shunting catheter of claim 1, wherein the plurality of positioning elements are integrally formed with the plurality of expandable struts.

17. A shunting catheter system, comprising:
a shunting catheter, comprising:
a catheter shaft including a shaft lumen;
an ablation shaft disposed in the shaft lumen at a first state and extended from the catheter shaft at a second state;
an ablation mechanism disposed on the ablation shaft, the ablation mechanism comprising:
a plurality of expandable struts defining an expandable cage;
a plurality of positioning elements coupled to the plurality of expandable struts and disposed outwardly from the expandable cage at the second state;
a plurality of connector struts, each connector strut of the plurality of connector struts disposed between and coupling adjacent expandable struts of the plurality of expandable struts;
an energy source connected to the shunting catheter; and
a controller connected to the energy source and comprising a processor;
wherein the processor is configured to control the energy source to deliver ablation energy to a target location of a patient via the ablation mechanism.

18. The shunting catheter system of claim 17, further comprising a crimping shaft comprising a lumen, wherein the second state of the shunting catheter comprises a first deployment state, a second deployment state, and a third deployment state, in the first deployment state the plurality of positioning elements and the plurality of expandable struts are retracted in the lumen of the crimping shaft, in the second deployment state the plurality of positioning elements extend outwardly from the lumen of the crimping shaft and the plurality of expandable struts are retracted in the lumen of the crimping shaft, and in the third deployment state the plurality of positioning elements and the plurality of expandable struts extend outwardly from the lumen of the crimping shaft.

19. The shunting catheter system of claim 17, wherein a portion of the ablation mechanism comprises an insulator configured to inhibit transmission of the ablation energy therethrough.

20. The shunting catheter system of claim 17, wherein the plurality of positioning elements comprises a first positioning element and a second positioning element, the second positioning element being longitudinally offset from the first positioning element.

21. The shunting catheter system of claim 17, wherein the plurality of expandable struts act as electrodes and are configured to deliver the ablation energy to the target location of the patient.

22. The shunting catheter system of claim 17, wherein the ablation mechanism further comprises at least one electrode connected to the expandable cage and configured to deliver the ablation energy to the target location of the patient.

23. The shunting catheter system of claim 17, wherein the plurality of expandable struts are self-expandable at the second state.

24. A method for creating a shunt, comprising:
deploying a shunting catheter in a first state, the shunting catheter comprising:
a catheter shaft including a shaft lumen;
an ablation shaft disposed in the shaft lumen at the first state;
an ablation mechanism disposed on the ablation shaft and comprising a plurality of expandable struts and a plurality of positioning elements;
disposing the shunting catheter proximate to a target location of a patient;
operating the shunting catheter to a second state, wherein the ablation shaft and the ablation mechanism extend from the catheter shaft;
contacting at least one of the plurality of positioning elements against tissue at the target location of the patient;
expanding an opening at the target location of the patient by expanding the plurality of expandable struts; and
delivering ablation energy via the ablation mechanism to the target location of the patient;
wherein contacting the at least one of the plurality of positioning elements against tissue at the target location of the patient comprises permitting the at least one of the plurality of positioning elements to self-expand;
wherein permitting the at least one of the plurality of positioning elements to self-expand comprises retracting a crimping shaft from the at least one of the plurality of positioning elements.

25. The method of claim 24, wherein the shunting catheter further comprises a crimping shaft comprising a lumen, and operating the shunting catheter to the second state comprises operating the shunting catheter to a first deployment state, then a second deployment state, and then a third deployment state, in the first deployment state the plurality of positioning elements and the plurality of expandable struts are retracted in the lumen of the crimping shaft, in the second deployment state the plurality of positioning elements extend outwardly from the lumen of the crimping shaft and the plurality of expandable struts are retracted in the lumen of the crimping shaft, and in the third deployment state the plurality of positioning elements and the plurality of expandable struts extend outwardly from the lumen of the crimping shaft.

26. The method of claim 24, wherein expanding the plurality of expandable struts comprises permitting the plurality of expandable struts to self-expand.

27. A shunting catheter, comprising:
a catheter shaft including a shaft lumen;
an ablation shaft disposed in the shaft lumen at a first state and extended from the catheter shaft at a second state;
an ablation mechanism disposed on the ablation shaft and expandable at the second state, the ablation mechanism comprising:
a plurality of expandable struts; and
a plurality of positioning elements coupled to the plurality of expandable struts and disposed radially outwardly from the plurality of expandable struts at the second state, the plurality of positioning elements comprising a first positioning element and a second positioning element, the second positioning element being longitudinally offset from the first positioning element;

wherein the ablation mechanism is configured to receive energy from an energy source and deliver ablation energy to a target location of a patient.

28. The shunting catheter of claim 27, wherein the ablation mechanism further comprises a plurality of connector struts, each connector strut of the plurality of connector struts disposed between and coupling adjacent expandable struts of the plurality of expandable struts.

29. The shunting catheter of claim 27, wherein the catheter shaft defines a first axis, the ablation shaft defines a second axis at the second state, and the second axis and the first axis form an angle greater than zero degrees.

30. The shunting catheter of claim 27, wherein at least one of the positioning elements of the plurality of positioning elements comprises a curved distal end defining a soft landing zone configured to contact tissue at the target location of the patient.

\* \* \* \* \*